US009757420B2

(12) United States Patent
Gregory et al.

(10) Patent No.: US 9,757,420 B2
(45) Date of Patent: Sep. 12, 2017

(54) GENE EDITING FOR HIV GENE THERAPY

(71) Applicant: Sangamo BioSciences, Inc., Richmond, CA (US)

(72) Inventors: Philip D. Gregory, Richmond, CA (US); Jianbin Wang, Richmond, CA (US); Paula M. Cannon, Los Angeles, CA (US)

(73) Assignees: Sangamo Therapeutics, Inc., Richmond, CA (US); University of Southern California, Los Angeles, CA (US)

( * ) Notice: Subject to any disclaimer, the term of this patent is extended or adjusted under 35 U.S.C. 154(b) by 0 days.

(21) Appl. No.: 14/807,595

(22) Filed: Jul. 23, 2015

(65) Prior Publication Data

US 2016/0022737 A1    Jan. 28, 2016

Related U.S. Application Data

(60) Provisional application No. 62/029,037, filed on Jul. 25, 2014, provisional application No. 62/036,511, filed on Aug. 12, 2014, provisional application No. 62/042,059, filed on Aug. 26, 2014, provisional application No. 62/172,574, filed on Jun. 8, 2015.

(51) Int. Cl.
| | |
|---|---|
| *C12N 5/10* | (2006.01) |
| *A61K 48/00* | (2006.01) |
| *C12N 15/00* | (2006.01) |
| *C12N 15/09* | (2006.01) |
| *A61K 35/28* | (2015.01) |
| *C12N 15/85* | (2006.01) |
| *C12N 15/90* | (2006.01) |

(52) U.S. Cl.
CPC .............. *A61K 35/28* (2013.01); *C12N 15/85* (2013.01); *C12N 15/907* (2013.01); *A61K 48/00* (2013.01); *C12N 2740/16011* (2013.01)

(58) Field of Classification Search
None
See application file for complete search history.

(56) References Cited

U.S. PATENT DOCUMENTS

| | | |
|---|---|---|
| 5,789,538 A | 8/1998 | Rebar et al. |
| 5,925,523 A | 7/1999 | Dove et al. |
| 6,007,988 A | 12/1999 | Choo |
| 6,013,453 A | 1/2000 | Choo |
| 6,140,081 A | 10/2000 | Barbas, III |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,689,558 B2 | 2/2004 | Case |
| 6,794,136 B1 | 9/2004 | Eisenberg et al. |
| 6,824,978 B1 | 11/2004 | Cox, III et al. |
| 6,903,185 B2 | 6/2005 | Kim et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,074,596 B2 | 7/2006 | Darzynkiewicz et al. |
| 7,153,949 B2 | 12/2006 | Kim et al. |
| 7,163,824 B2 | 1/2007 | Cox, III et al. |
| 7,253,273 B2 | 8/2007 | Collingwood |
| 7,262,054 B2 | 8/2007 | Jamieson et al. |
| 7,361,635 B2 | 4/2008 | Miller et al. |
| 7,888,121 B2 | 2/2011 | Urnov et al. |
| 7,914,796 B2 | 3/2011 | Miller et al. |
| 7,951,925 B2 | 5/2011 | Ando et al. |
| 7,972,854 B2 | 7/2011 | Miller et al. |
| 8,084,593 B2 | 12/2011 | Luban et al. |
| 8,110,379 B2 | 2/2012 | DeKelver et al. |
| 8,153,773 B2 | 4/2012 | Jemielity et al. |
| 8,329,986 B2 | 12/2012 | Butler et al. |
| 8,409,861 B2 | 4/2013 | Guschin et al. |
| 8,524,221 B2 | 9/2013 | Ando et al. |
| 8,563,314 B2 | 10/2013 | Gregory et al. |
| 8,586,526 B2 | 11/2013 | Gregory et al. |
| 8,623,618 B2 | 1/2014 | Doyon et al. |
| 8,623,815 B2 | 1/2014 | Berthoux et al. |

(Continued)

FOREIGN PATENT DOCUMENTS

| | | |
|---|---|---|
| GB | 2338237 A | 12/1999 |
| WO | WO 95/19431 A1 | 7/1995 |

(Continued)

OTHER PUBLICATIONS

US 8,563,598, 10/2013, Sieber et al. (withdrawn)
Shun et al., LEDGF/p75 functions downstream from preintegration complex formation to effect gene-specific HIV-1 integration. Genes & Develop., 2007, 21:1767-1778.*
Scherer et al., Ex vivo gene therapy for HIV-1 treatment. Human Molecular Genetics, 2011, vol. 20, Review Issue 1 R100-R107.*
Adolph, et al., "Retroviral Restriction Factor APOBEC3G Delays the Initiation of DNA Synthesis by HIV-1 Reverse Transcriptase," *PLoS One* 8:1-11 (2013).
Beerli, et al., "Engineering Polydactyl Zinc-Finger Transcription Factors," *Nature Biotechnol.* 20:135-141(2002).
Boch, et al., "Breaking the Code of DNA Binding Specificity of TAL-Type III Effectors," *Science* 326:1509-1512 (2009).

(Continued)

*Primary Examiner* — Kevin Hill
*Assistant Examiner* — Arthur S Leonard
(74) *Attorney, Agent, or Firm* — Pasternak Patent Law; Susan Abrahamson

(57) ABSTRACT

The present disclosure is in the field of genome engineering, particularly targeted integration of anti-HIV transgenes into the genome of a cell for the treatment and/or prevention of HIV.

14 Claims, 25 Drawing Sheets

(56) References Cited

U.S. PATENT DOCUMENTS

| | | | |
|---|---|---|---|
| 8,697,359 B1 | 4/2014 | Zhang | |
| 8,703,489 B2 | 4/2014 | Wang | |
| 8,748,372 B2 | 6/2014 | Luban et al. | |
| 8,945,868 B2 | 2/2015 | Collingwood | |
| 8,956,828 B2 | 2/2015 | Bonini et al. | |
| 9,005,973 B2 | 4/2015 | Cost et al. | |
| 9,045,763 B2 | 6/2015 | DeKelver et al. | |
| 2003/0232410 A1 | 12/2003 | Liljedahl et al. | |
| 2005/0026157 A1 | 2/2005 | Baltimore et al. | |
| 2005/0064474 A1 | 3/2005 | Urnov et al. | |
| 2005/0208489 A1 | 9/2005 | Carroll et al. | |
| 2005/0267061 A1 | 12/2005 | Martin | |
| 2006/0063231 A1 | 3/2006 | Li et al. | |
| 2006/0188987 A1 | 8/2006 | Guschin et al. | |
| 2007/0134796 A1* | 6/2007 | Holmes | A61K 48/0008 435/455 |
| 2007/0141679 A1 | 6/2007 | Sodroski et al. | |
| 2007/0218528 A1 | 9/2007 | Miller | |
| 2008/0131962 A1 | 6/2008 | Miller | |
| 2008/0159996 A1 | 7/2008 | Ando et al. | |
| 2009/0029468 A1 | 1/2009 | Barbas et al. | |
| 2009/0054985 A1 | 2/2009 | Anderson | |
| 2009/0305346 A1 | 12/2009 | Miller | |
| 2010/0047805 A1 | 2/2010 | Wang | |
| 2010/0218264 A1 | 8/2010 | Cui et al. | |
| 2011/0201055 A1 | 8/2011 | Doyon et al. | |
| 2011/0207221 A1 | 8/2011 | Cost et al. | |
| 2011/0265198 A1 | 10/2011 | Gregory et al. | |
| 2012/0017290 A1 | 1/2012 | Cui et al. | |
| 2012/0093787 A1 | 4/2012 | Holmes et al. | |
| 2012/0201794 A1* | 8/2012 | Chen | A01K 67/0271 424/93.21 |
| 2013/0122591 A1 | 5/2013 | Cost et al. | |
| 2013/0137104 A1 | 5/2013 | Cost et al. | |
| 2013/0171732 A1 | 7/2013 | Holmes et al. | |
| 2013/0177960 A1 | 7/2013 | Rebar | |
| 2013/0177983 A1 | 7/2013 | Rebar | |
| 2014/0335063 A1 | 11/2014 | Cannon et al. | |
| 2015/0056705 A1 | 2/2015 | Conway et al. | |
| 2015/0110762 A1 | 4/2015 | Holmes et al. | |
| 2015/0174169 A1 | 6/2015 | Genovese et al. | |
| 2016/0024474 A1 | 1/2016 | Conway et al. | |

FOREIGN PATENT DOCUMENTS

| | | |
|---|---|---|
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/16536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 2010/079430 A1 | 7/2010 |

OTHER PUBLICATIONS

Bonas, et al., "Genetic and Structural Characterization of the Avirulence Gene AVRBS3 From Xanthomonas Campestris PV. Vesicatoria,"*Mol. Gen. Genet.* 218:127-136 (1989).

Brass, et al., "Identification of Host Proteins Required for HIV Infection Through a Functional Genomic Screen," *Science* 319(5865):921-926 (2008).

Butler, et al., "Development of a Vascular Niche Platform for Expansion of Repopulating Human Cord Blood Stem and Progenitor Cells," *Blood* 120(6):1344-1347 (2012).

Ceredig, "When One Cell Is Enough," *Stem Cell Res. Ther.* 3(1):1-2 (2012).

Chaurasia, et al., "Epigenetic Reprogramming Induces the Expansion of Cord Blood Stem Cells," *The Journal of Clinical Investigation* 124(6):2378-2395 (2014).

Choo, et al., "Advances in Zinc Finger Engineering," *Curr. Opin. Struct. Biol.* 10:411-416 (2000).

Christian, et al., "Targeting DNA Double-Strand Breaks With TAL Effector Nucleases," *Genetics* epub 10.1534/genetics.110.120717 (2010).

Cong, et al., "Multiplex Genome Engineering Using CRISPR/CAS Systems," Sciencexpress 1/10.1126/science 1231143 (2013).

De Lima, et al., "Transplantation of Ex Vivo Expanded Cord Blood Cells Using the Copper Chelator Tetraethylenepentamine: A Phase I/II Clinical Trial," *Bone Marrow Transplantation* 41:771-778 (2008).

Deng, et al., "Identification of a Major Co-Receptor for Primary Isolates of HIV-1," *Nature* 381(6584):661-666 (1996).

Fares, et al., "798- UM171 Is a Novel and Potent Agonist of Human Hematopoietic Stem Cell Renewal," $55^{th}$ ASH Abstract Tuesday, Dec. 10, 2013: 8:45 AM.

Feng, et al., "HIV-1 Entry Cofactor: Functional CDNA Cloning of a Seven-Transmembrane, G Protein-Coupled Receptor," *Science* 272:872-877 (1996).

Gabriel, et al., "An Unbiased Genome-Wide Analysis of Zinc-Finger Nuclease Specificity," *Nat. Biotech.* 29:816-823 (2011).

Genovese, et al., "Targeted Genome Editing in Human Repopulating Haematopoietic Stem Cells," *Nature* 510(7504):235-240 (2014).

Guo, et al., "Directed Evolution of an Enhanced and Highly Efficient FOKI Cleavage Domain for Zinc Finger Nucleases," *J. Mol. Biol.* 400(1):96-107 (2010).

Guo, et al., "Inhibition of TRNA3 Lys-Primed Reverse Transcription by Human APOBEC3G During Human Immunodeficiency Virus Type 1 Replication," *Journal of Virology* 80(23):11710-11722 (2006).

Gupta, et al., "Mutation of a Single Residue Renders Human Tetherin Resistant to HIV-1 VPU-mediated Depletion," *PLoS Pathog.* 5(5):e1000443 (2009).

Haft, et al., "A Guild of 45 CRISPR-Associated (CAS) Protein Families and Multiple CRISPR/CAS Subtypes Exist in Prokaryotic Genomes," *PLoS Comput. Biol.* 1(6):474-483 (2005).

Ho, et al., "Pathogenic Infection of Macaca Nemestrina With a CCR5-Tropic Subtype-C Simian-Human Immunodeficiency Virus," *Retrovirology* 6:65 (2009).

Hoban, et al., Correction of the Sickle Cell Disease Mutation in Human Hematopoietic Stem/Progenitor Cells, *Blood* 125:2597-2604 (2015).

Holt, et al., "Human Hematopoietic Stem/Progenitor Cells Modified by Zinc-Finger Nucleases Targeted to CCR5 Control HIV-1 In Vivo," *Nat. Biotech.* 28(8):839-847(2010).

Horwitz, et al., "Umbilical Cord Blood Expansion With Nicotinamide Provides Long-Term Multilineage Engraftment," *The Journal of Clinical Investigation* 124(7):3121-3128 (2014).

Isalan, et al., "A Rapid, Generally Applicable Method to Engineer Zinc Fingers Illustrated by Targeting the HIV-1 Promoter," *Nat. Biotechnol.* 19:656-660 (2001).

Jansen, et al., "Identification of Genes That Are Associated With DNA Repeats in Prokaryotes," *Molecular Microbiology* 43(6):1565-1575 (2002).

Jinek, et al., "RNA-Programmed Genome Editing in Human Cells," *Elife* 2:e00471 (2013).

Kay, et al., "A Bacterial Effector Acts As a Plant Transcription Factor and Induces a Cell Size Regulator," *Science* 318:648-651 (2007).

Kobayashi, et al., "Identification of Amino Acids in the Human Tetherin Transmembrane Domain Responsible for HIV-1 VPU Interaction and Susceptibility," *J. Virol.* 85(2):932-945 (2011).

Kormann, et al., "Expression of Therapeutic Proteins After Delivery of Chemically Modified MRNA in Mice," *Nature Biotechnology* 29(2):154-157 (2011).

Langmead & Salzberg, "Fast Gapped-Read Alignment With Bowtie 2," *Nat. Meth.* 9:357-359 (2012).

(56) References Cited

OTHER PUBLICATIONS

Li, et al., "Removal of Arginine 332 Allows Human Trims to Bind Human Immunodeficiency Virus Capsids and to Restrict Infection," *J. Virol.* 80(14):6738 (2006).

Li, et al., "Genomic Editing of the HIV-1 Coreceptor CCR5 in Adult Hematopoietic Stem and Progenitor Cells Using Zinc Finger Nucleases," *Mol. Ther.* 21:1259-1269 (2013).

Lombardo, et al., "Gene Editing in Human Stem Cells Using Zinc Finger Nucleases and Integrase-Defective Lentiviral Vector Delivery," *Nat. Biotech.* 25:1298-1306 (2007).

Lombardo, et al., "Site-Specific Integration and Tailoring of Cassette Design for Sustainable Gene Transfer," *Nat. Meth.* 8:861-869 (2011).

Maertens, et al., "LEDGF/P75 is Essential for Nuclear and Chromosomal Targeting of HIV-1 Integrase in Human Cells," *J. Biol. Chem.* 278(35):33528-33539 (2003).

Makarova, et al., "A DNA Repair System Specific for Thermophilic Archaea and Bacteria Predicted by Genomic Context Analysis," *Nucleic Acids Res.* 30:482-496 (2002).

Makarova, et al., "A Putative RNA-Interference-Based Immune System in Prokaryotes: Computational Analysis of the Predicted Enzymatic Machinery, Functional Analogies With Eukaryotic RNAI, and Hypothetical Mechanisms of Action," *Biol. Direct* 1:7 (2006).

Moscou, et al., "A Simple Cipher Governs DNA Recognition by TAL Effectors," *Science* 326:1501 (2009).

Neagu, et al., "Potent Inhibition of HIV-1 by TRIM5-Cyclophilin Fusion Proteins Engineered From Human Components," *J. Clin. Invest.* 119:3035-3047 (2009).

Pabo, et al., "Design and Selection of Novel CYS2HIS2 Zinc Finger Proteins," *Ann. Rev. Biochem.* 70:313-340(2001).

Pabst, et al., "Identification of Small Molecules That Support Human Leukemia Stem Cell Activity Ex Vivo," *Nat. Meth.* 11:436-442 (2014).

Pham, et al., "Generation of Human TRIM5A Mutants With High HIV-1 Restriction Activity," *Gene Therapy* 19(7):859-871 (2006).

Podsakoff, et al., "Selective Survival of Peripheral Blood Lymphocytes in Children With HIV-1 Following Delivery of an Anti-HIV Gene to Bone Marrow CD34(+) Cells," *Mol. Ther.* 12(1):77-86 (2005).

Price, et al., "CPSF6 Defines a Conserved Capsid Interface That Modulates HIV-1 Replication," *PLoS Pathogens* 8(8):e1002896 (2012).

Ran, et al., "In Vivo Genome Editing Using *Staphylococcus aureus* CAS9," *Nature* 520:186-194 (2015).

Reitsma, et al., "Method for Purification of Human Hematopoietic Stem Cells by Flow Cytometry," *Hematopoietic Stem Cell Protocols* 63:59-77 (2002).

Schaller, et al., "HIV-1 Capsid-Cyclophilin Interactions Determine Nuclear Import Pathway, Integration Targeting and Replication Efficiency," *PLoS Pathog.* 7(12):e1002439 (2011).

Schrofelbauer, et al., A Single Amino Acid of APOBEC3G Controls Its Species-Specific Interaction With Virion Infectivity Factor (VIF), *PNAS USA* 101(11):3927-3932 (2004).

Segal, et al., "Custom DNA-Binding Proteins Come of Age: Polydactyl Zinc-Finger Proteins," *Curr. Opin. Biotechnol.* 12:632-637 (2001).

Sheng, et al., "Structure-Based Cleavage Mechanism of Thermus Thermophilus Argonaute DNA Guide Strand-Mediated DNA Target Cleavage," *Proc. Natl. Acad. Sci. USA* 111(2):652-657 (2013) doi: 10.1073/pnas.1321032111.

Swarts, et al., "DNA-Guided DNA Interference by a Prokaryotic Argonaute," *Nature* 507(7491):258-261 (2014).

Takahashi, et al., "CD133 Is a Positive Marker for a Distinct Class of Primitive Human Cord Blood-Derived CD34-Negative Hematopoietic Stem Cells," *Leukemia* 28:1308-1315 (2014).

Tebas, et al., "Gene Editing of CCR5 in Autologous CD4 T Cells of Persons Infected with HIV," *New Eng. J. Med.* 370(10):901-910 (2014).

Towers and Norsadeghi, "Interactions Between HIV-1 and the Cell-Autonomous Innate Immune System," *Cell Host Microbe* 16(1):10-18 (2014).

Trobridge, et al., "Protection of Stem Cell-Derived Lymphocytes in a Primate Aids Gene Therapy Model After in Vivo Selection," *PLoS One* 4(11): e7693 (2009).

Wang, et al., "Targeted Gene Addition to a Predetermined Site in the Human Genome Using a ZFN-Based Nicking Enzyme," *Genome Research* 22:1316-1326 (2012).

Wilen, et al., "Engineering HIV-Resistant Human CD4+ T Cells With CXCR4-Specific Zinc-Finger Nucleases," *PLOS Pathogens* 7(4):1-15 (2011).

Xiao, et al., "Production of High-Titer Recombinant Adeno-Associated Virus Vectors in the Absence of Helper Adenovirus," *J. Virol.* 72:2224-2232 (1998).

Xu, et al., "A Single Amino Acid Substitution in Human APOBEC3G Antiretroviral Enzyme Confers Resistance to HIV-1 Virion Infectivity Factor-Induced Depletion," *PNAS USA* 101(15):5652-5657(2004).

Younan, et al., "Positive Selection of MC46-Expressing CD41 T Cells and Maintenance of Virus Specific Immunity in a Primate Aids Model," *Blood* 122(2):179-187 (2013).

Yu, et al., "An Engineered VEGF-Activating Zinc Finger Protein Transcription Factor Improves Blood Flow and Limb Salvage in Advanced-Age Mice," *FASEB J.* 20:479-481 (2006).

\* cited by examiner

FIG. 5

APOBEC3G

D-128 (Exon 3)

Intron 2 | 3

Intron 2

Exon 3 - and site of D-128 (GAC)

Intron 3

```
GTACCACCCG GACTCCAATC ACTTTGCAGG CAGGAGCTAA GCCAGCTGGG AAAGCAAACC AGGCACTGAT
AAGTGAAGTG CCCGGCGGCG GGCTATCCGG TGTGTCCTTC TCTCCACAC TTTCCAAGTC CGTGCCCCTG
ACCTTCCTGC TGGACCGTCC TGGGATCGGA TCGTGGAGGG GGTTGCCTC TGCACAAAAG GCCTTGTGTT
TCCGTTTTTC TTTTCTTTTC TTTTCTTTTT AGACAGAGTT TCACTCTTGT TGCTCAGGCT
GGAGTGCAAT GACGCGATCT CGGCTCACAG CAACCTCTGC CTCCCGGGTT CAAGCGATGC TGTGCCTCA
GACTGCGAAG TAGCTGCGAT TACAGGTGCC CCAGCCACAG CTTCTGACCT TTTTTTTTG TATTTTTAGT
ACAGATGGGG TTTCACCATA TTCACCAGGC TGGTCTGAA CTTCTGACCT CAGGTGATCC ACCTGCCTCG
GCCTCCCAAA GTGTTGGGAT TACAGGTGTG AGCCACGGC CCGGCCTAAT TTTAATATTT AATTAATCCA
ATGTGGCTAA CATATTACTT CAACATTAAT TAACATAAAA TTCTTGACAA GATAATGAAG TTTCTTTTC
TTGTCACACC GAGTCTTTGA AATGAGCTGC GTGGGTCACG TACAGTGGGT GGCTCGCACC TCTAATCCA
GCACTTTGGG AGGCCAAGGC CTCTACTAAA AATACAAAAA CCTGAAGTCA GATATTCAAA ACCGGCCTAG GCAACATGGT
GAAATCCCAT CCGAGGGCTG AGCCAGGAGA TCGTGGAGGG GGTTGCCTC AGGTTGTA CACCCTGTAAT
CCCAGCTACT CGGGAGGCTG CCTGGGCAAC AAGAGGCGAA CTCCATTCCA AAAAAATAA AGAAATGAG
ATTGCATCCT TGCATTCCAG ATCAGGAGGA CAGGCTCTTA TCCATTCAAGT CTGCAGGCAG CCCTTGCCA
TGGTGTATT TTCAGGTGCC CCCGACATGG ACAGTAGGGG TCCCAGGATGT CTGGCTGGG GGAACAAGGC
TGTCACCCCC GGGCAGCAGG GGCCAGGCC ACAGTAGGGG GCTGGGAAAA CTTCAAGCGT GATGGCCTGG AGAATGGATG
AGACCCTAGA GGGCAGGCCT CTAGACGAGG CATGCAGCGAGC TGGATAGGGG GCCATTACCA CGTGTCTTTGG
CTAGAATTCA CACACAGGCC GATGCTTCAA TCCCCTGTCA GCGGGATCGC CTTGAATAAC CACACAGTG GCACCAGTGG GTATGGGCTC
TGCACCTTGT GATGCTTCAA CTGGGAAAG CATAGGAGC TCCAAGAGG CTTGAATAAC ACAGCAGTGG CACCAGTGG GTATGGCTC
GAGTTCTTGA CTCTGGAGG GAAGGTTGTT CGTGGACATGG GGCCAGAAGCT CAGTGGAGTA GTGGCCTGGG ATGCGAGTC
ACGTGGGGGT CGTTGACATGG GCCAGAAGCT CAGGAGAGG AAGCAGTTA GTCTGACATA CACACAGTG AGCTAGAGGG
ACTCCTGCTC GAAGAGACAC AAAGAGGGGC TGAAGTCGCC CTTGAATAAC ACAGCAGTGG CACCAGTGG AGTCGCAGTT
CAAGAGACAG CATAGCTGCT TGTAGGTGCC CCTCCTTAAG ACACAGGGGA TGGAGGAAAG GAGCTTCAAT TACTGAACAT
CCCACAGCCT CAGAACAAAC ACTCAAACCG CTGCCCCCCC CTGCCTCTCC CTGCCTCTCCC GCAAGATCT
GAGCTTTGA GCCAGACAAAC AACAGGGGA TGGAGGAAAG GAGCTTCAAT TACTGAACAT CCCCACAGGT GCAAGATCT
CCTGGACTCC TGTCCTGGCC CCCTGCTCTG TATTCCGAAC TTAAGTACCA CCCAGAGATG AGATTCTTCC
CTTGGACTGC CCCCTGCTCC CCCTGGCTCC CAAGTGTCATC GTGACCAGGA GTATGAGGTC ACCTGGTACA TATCCTGGAG
ACTGGTTCAG CAAGTGTCACA AAGTGTACAA CACGTTCCTG GCCGAGGACC CGAAGGTTAC CCTGACCATC
CCCCTGCACA GCCTCTACTA CTTCTGGGAC CCAGATTACC AGGAGGGCCT TCGCAGCCTG TGTCAGAAAA
TTTGTTGCCC GCCTGCCACC GCGTGCCAGG TGAAGATCA GGAAG TGGGGAGGTC TGGGGGTGTGG
GAGACGGGTC TTAAGTGTCT GTGATGGGTC CTTCCCCACAC ATACCTGTTG GTCTGCTCTG ATGCCTGCAA
GAGGCAAGTG TCCCAGGGGA GCCTGCTGGT TTGGGTCTTG CGCTGACTGT AACTAGTATC TAGAATATGT
CTGGGAGGGG AGGGTCCCGA GGGTCACAGA GAGAGACTGA CTGGGCTTGA CTGCCTCTC TCTTCTTTTT
CTTAG
```

Input HSC

| % CCR5 disruption | % HDR | % GFP FACS |
|---|---|---|
| 30.9 | 17.8 | 9.1 |

NSG mice

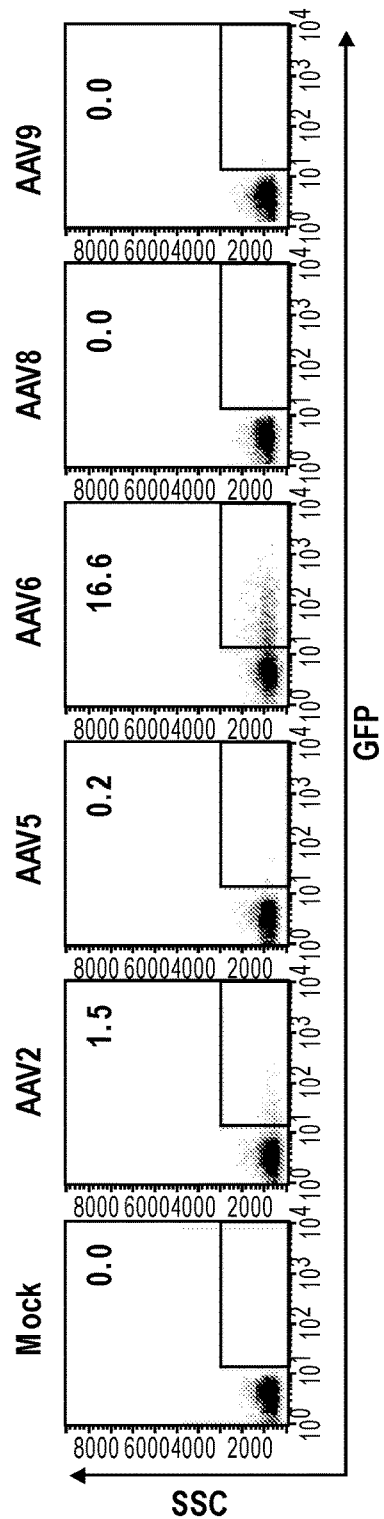
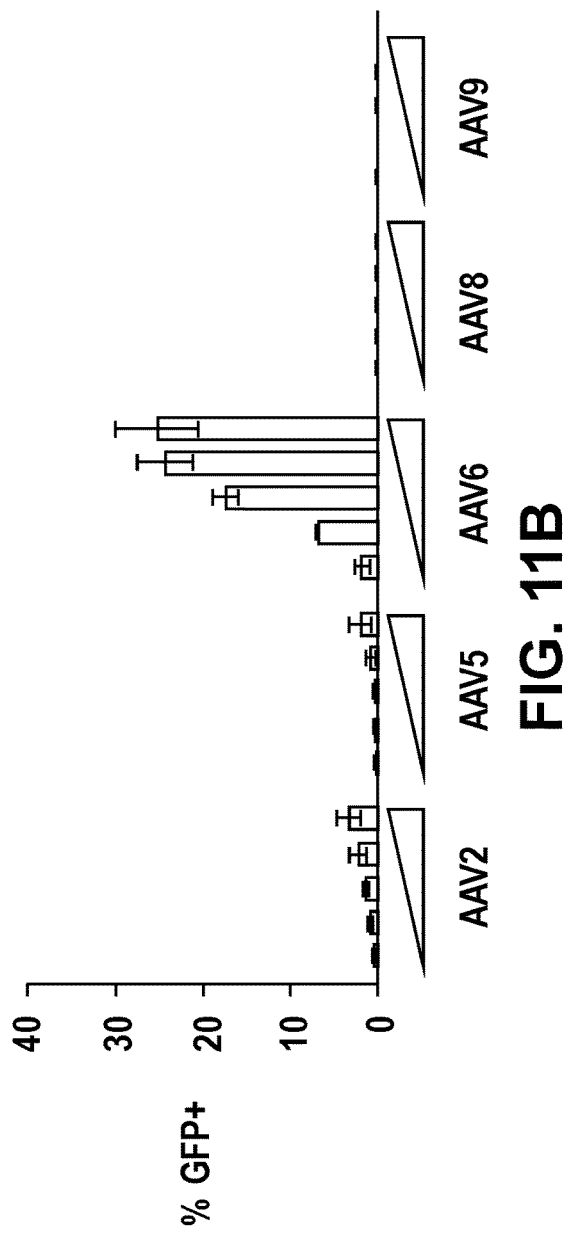
FIG. 11A
FIG. 11B

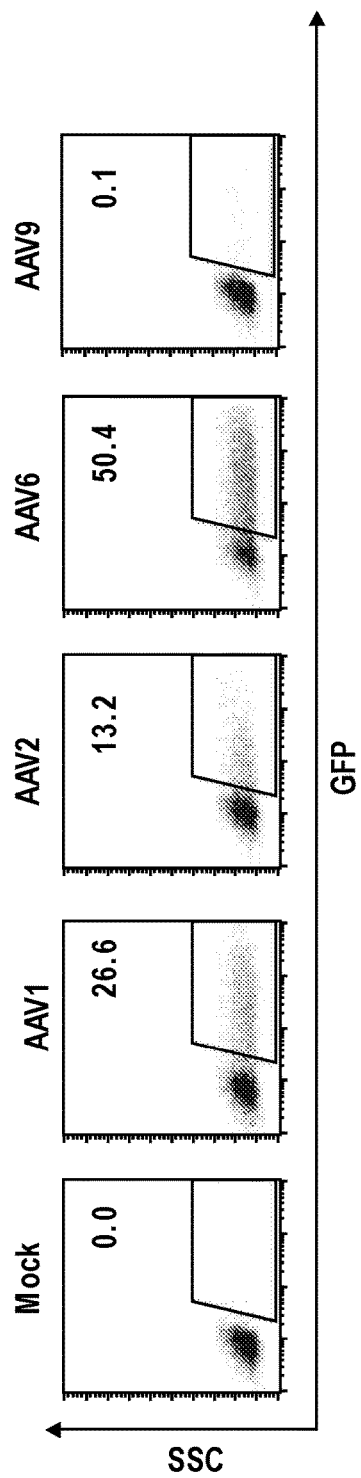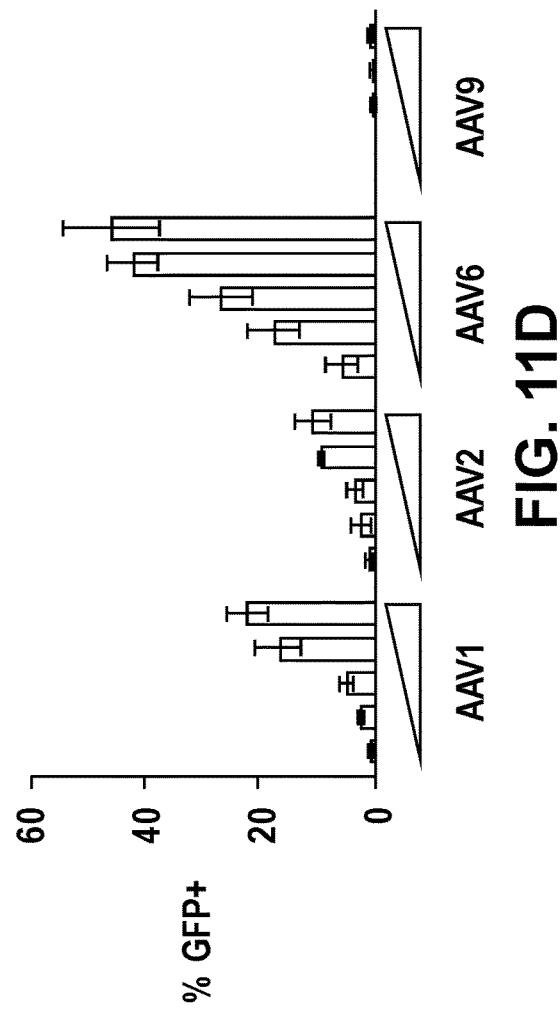
FIG. 11C
FIG. 11D

SEQUENCE LISTING

<160> NUMBER OF SEQ ID NOS: 27

<210> SEQ ID NO 1
<211> LENGTH: 28
<212> TYPE: PRT
<213> ORGANISM: Homo sapiens

<400> SEQUENCE: 1

Pro Lys Pro Gln Ile Ile Tyr Gly Ala Arg Gly Thr Arg Tyr Gln Thr
1               5                   10                  15

Phe Val Asn Phe Asn Tyr Cys Thr Gly Ile Leu Gly
            20                  25

<210> SEQ ID NO 2
<211> LENGTH: 30
<212> TYPE: PRT
<213> ORGANISM: Macaca mulatta

<400> SEQUENCE: 2

Arg Asn Pro Gln Ile Met Tyr Gln Ala Pro Gly Thr Leu Phe Thr Phe
1               5                   10                  15

Pro Ser Leu Thr Asn Phe Asn Tyr Cys Thr Gly Val Leu Gly
            20                  25                  30

<210> SEQ ID NO 3
<211> LENGTH: 28
<212> TYPE: PRT
<213> ORGANISM: Homo sapiens

<400> SEQUENCE: 3

Pro Lys Pro Gln Ile Ile Tyr Gly Ala Pro Gly Thr Arg Tyr Gln Thr
1               5                   10                  15

Phe Val Asn Phe Asn Tyr Cys Thr Gly Ile Leu Gly
            20                  25

<210> SEQ ID NO 4
<211> LENGTH: 28
<212> TYPE: PRT
<213> ORGANISM: Homo sapiens

<400> SEQUENCE: 4

Pro Lys Pro Gln Ile Ile Tyr Gly Ala Gly Gly Thr Gly Tyr Gln Thr
1               5                   10                  15

Phe Val Asn Phe Asn Tyr Cys Thr Gly Ile Leu Gly
            20                  25

<210> SEQ ID NO 5
<211> LENGTH: 28
<212> TYPE: PRT
<213> ORGANISM: Homo sapiens

<400> SEQUENCE: 5

Arg Asn Pro Gln Ile Met Tyr Gln Ala Pro Gly Thr Arg Tyr Gln Thr
1               5                   10                  15

Phe Val Asn Phe Asn Tyr Cys Thr Gly Ile Leu Gly
            20                  25

<210> SEQ ID NO 6
<211> LENGTH: 30
<212> TYPE: PRT
<213> ORGANISM: Homo sapiens

<400> SEQUENCE: 6

Pro Lys Pro Gln Ile Ile Tyr Gln Ala Pro Gly Thr Leu Phe Thr Phe
1               5                   10                  15

Pro Ser Leu Thr Asn Phe Asn Tyr Cys Thr Gly Ile Leu Gly
            20                  25                  30

<210> SEQ ID NO 7
<211> LENGTH: 408
<212> TYPE: DNA
<213> ORGANISM: Homo sapiens

<400> SEQUENCE: 7
agctgacaga tgtccgacgc tactggggta aggagaagtc acattatcat aagccaccct      60
gcggcttatc attattatta tctttatctt ttagaatttt atgttctcta ttaggctcat     120
gttttaagat ttatgattct ccttccaaga cacacataac ttaccccctcc ttataacttc    180 taaacaaggt tcctcccagt tttctctcaa gtctttatca agatttctct catatcacaa    240
ataaagttac attatatccc ttagctgacc tgttaatttt tctacagttg atgtgacagt    300
ggctccaaac aacatttcat gtgctgtcat ttctgaagat aagagacaag tgagctctcc    360
gaaaccacag ataatatatg gggcacgagg acaagatac cagacatt                   408

<210> SEQ ID NO 8
<211> LENGTH: 2385
<212> TYPE: DNA
<213> ORGANISM: Homo sapiens

<400> SEQUENCE: 8
gtaccacccg gactccaatc actttgcagg caggagctaa gccagctggg aaagcaaacc      60
acgcactgat aagtgaagtg cccggcggcg ggctatccag tgtgtccttc tctcccacac     120
tttccaagtc cgtggccctg accttcctgc tggaccgtcc tgggatcgga tcgtggaggg    180
ggtttgcctc tgcacaaaag gccttgtgtt tccgtttttc ttttctttc ttttttcttt     240 ttttttttg agacagagtt tcactcttgt tgctcaggct ggagtgcaat gacgcgatct     300
cggctcacag caacctctgc ctcctgggtt caagcgatgc tgtcgcctca gactcgcaag    360
tagctgcgat tacaggtgcc caccaccacg cccagctgat ttttttttg tattttagt      420 acagatgggg tttcaccata ttcaccaggc tggtctcgaa cttctgacct caggtgatcc    480
acctgcctcg gcctcccaaa gtgttgggat tacaggtgtg agccacagcg ccggcctaat    540
tttaatattt aattaatcca atgtggctaa catattactt caacattaat taacataaaa    600
ttcttgacaa gataatgaag tttctttttc ttgtcacacc gagtctttga atgagctgc     660 gtgggtcacg tacagtgggt ggctcgcacc tctaatccca gcactttggg aggccaaggc    720
gggcagatca cctgaagtta gatattcaaa ccggcctgg gcaacatggt gaaatcccat     780
ctctactaaa aatacaaaaa aaaaaaaaat tagccaggca tggtggcagt cacctgtaat    840
cccagctact cggaggctg aggcaggaga accgcttgat cccatgaggc agaggttgta    900
gtgagccaag attgcatcct tgcattccag cctgggcaac aagagcgaaa ctccatctca    960

```
aaaaaaaaaa aagaaatgag tggtgtattt ttcaggtgcc caggtctcta atcagagccc    1020
catttcaagt actcagtagt cccttggcca tgtcaccccc cccgacatgg acagtgcagg    1080
tccagtgggc tccccactga ctgcaggcag ggaacaaggc agaccctaga gggccaggcc    1140
acagtagggg ctgaggatgt ctggtgaatg gatgcctggg agaatggatg ctagaattca    1200
cacacgaggc catgaacagg gctgggaaaa cttccaaact cagggaagca cgtgtcttgg    1260
tgcaccttgt gatgcttcaa cagcaggact gagatgggga catttacaat gaacagaaat    1320
gtatgggctc gagttctgga ctctgggaag tccctgtca atgcaccagc aactttccag    1380
ggcctgcgag ctgcacagtc acgtgggggt gaaggttgtt gccagaagct caggggatgc    1440
tccagacaga gtggcctggg atgtcgagtc actgctgctc cgtgacatgg gggcaagagg    1500
aagcagttta gtctgacata ctgccccccc agctagaggg caagagacag aaagaggggc    1560
tgaagtcgcc cttgaataac cacagcagtg gcacccacaa aggtgcagtt cccacagcct    1620
catagctgct tgtaggtgcc acctcttaag gccattacca tagcaattaa tactgaacat    1680
gagctttgga gcagacaaac actcaaaccg aacaggggga tggaggaaag gagcttcaat    1740
ggcaagatct cctggactcc tgtcctggcc cctcctcccc ctgccccacc cctgctctcc    1800
tcctgctccc cctctcagag cttgcccctga ccctgctcct ctcccaggtg tattccgaac    1860
ttaagtacca cccagagatg agattcttcc actggttcag caagtggagg aagctgcatc    1920
gtgaccagga gtatgaggtc acctggtaca tatcctggag cccctgcaca aagtgtacaa    1980
gggatatggc cacgttcctg ccgaggacc cgaaggttac cctgaccatc tttgttgccc    2040
gcctctacta cttctgggac ccagattacc aggaggcgct tcgcagcctg tgtcagaaaa    2100
gagacggtcc gcgtgccacc atgaagatca tgaattatga cggtgagaag tgggaggttc    2160
aggggtgtgg gagagactgc ttaagtgtct gtgatgggtc cttcccacac atacctgtgg    2220
gtctgctctg atgcctgcaa aggccaagtg tcccagggga gcctgtgggg ttgggtctgg    2280
cgctgactgt aactagtatc tagaatatgt ctggaggggg agggtcccga ggtcacagaa    2340
gagaggccag ctgggcttga ctgcgttctc tcttcttttt cttag                   2385
```

<210> SEQ ID NO 9
<211> LENGTH: 1138
<212> TYPE: DNA
<213> ORGANISM: Homo sapiens

<400> SEQUENCE: 9

```
atggcatcta cttcgtatga ctattgcaga gtgcccatgg aagacgggga taagcgctgt     60
aagcttctgc tggggatagg aattctggtg ctcctgatca tcgtgattct gggggtgccc    120
ttgattatct tcaccatcaa ggccaacagc gaggcctgcc gggacggcct tcgggcagtg    180
atggagtgtc gcaatgtcac ccatctcctg caacaagagc tgaccgaggc ccagaagggc    240
tttcaggatg tggaggccca ggccgccacc tgcaaccaca ctgtggtaag ctcctcaact    300
cctttggatg gcctagtact aggcggtggg agggacaaga atctctcccc agaaatctga    360
cccagggtgg gtctccaggg agatgcaggg gaggtcctga aactgctcct gggccccac    420 atcaagggac ctaggttccc ctaccagggt ttgtgggccc ctaacccagt ccagggcact    480
ggtgtagggg cagggtgtta aaactctcca gatcccccaa atcggggacc tcagtatccc    540
cctgggactt aggtgaattt ataaattctt tccagggcac tggtgtcggg ggccttgaaa    600
ctcctcgtgg gcaccagtcc tggggagta gaaatcccta ttcagggttg aaggggggacc    660 tcaccagacc ctgaaaaagg gggcttttga aattttcact tcatccctaa gaaactgaaa    720
```

```
tattcacctg ggtcctgata tgggggatct tgaaactctc gctgggcatg tcacttgggc    780
ggggaaatcc cactgcattc tggatttggt agggccctct aacttttctt gggccattgc    840
tcaggcaatc tggaaatgtc cactaaactt tggttatcga tagcctccaa gtttccacgt    900
ggggtggcct caaaactccc attttgagga cccacatgct tatgggtggc cctgggagag    960
tgtgtggttg tggctgttct ttaaggttgg agaccatggt gcagagaggg ttggaagaaa   1020
acctgaaagg ggtttgcatt taagcccctc tgtcccagg acctagggag gaggcccagg    1080
tcccaggggc agcagccaaa ctccccaggc caaaccccca gattctaact cttcttag    1138
```

<210> SEQ ID NO 10
<211> LENGTH: 25
<212> TYPE: DNA
<213> ORGANISM: Homo sapiens

<400> SEQUENCE: 10

```
ctgacctctt ctcttcctcc cacag                                           25
```

<210> SEQ ID NO 11
<211> LENGTH: 13
<212> TYPE: DNA
<213> ORGANISM: Homo sapiens

<400> SEQUENCE: 11

```
tttctctcca cag                                                        13
```

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12

```
agtttgtctc gaggtgatga                                                 20
```

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13

```
agtggggcaa gctttactag gg                                              22
```

<210> SEQ ID NO 14
<211> LENGTH: 50
<212> TYPE: DNA
<213> ORGANISM: Homo sapiens

<400> SEQUENCE: 14

```
tctgggggtg cccttgatta tcttcaccat caaggccaac agcgaggcct                50
```

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tctgggggtg cccttgatta tcttcatcat caaggccaac agcgaggcct        50

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ctccttataa cttctaaaca                                          20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gaaaccacag ataatatatg                                          20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gactgcttaa gtgtctgtga                                          20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gtccttccca cacatacctg                                          20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tgtgggaact gcacctttgt                                          20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 21
cctttggatg gcctagtact                                                20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gaggtcctga aactgctcct                                                20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gctcctgggc ccccacatca                                                20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tcaaggccaa cagcgaggcc                                                20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tgattatctt caccatcaag                                                20

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ggggtgccct tgattatctt c                                              21

<210> SEQ ID NO 27
<211> LENGTH: 9
<212> TYPE: PRT
<213> ORGANISM: Unknown
```

```
<220> FEATURE:
<223> OTHER INFORMATION: Description of Unknown:
      "LAGLIDADG" family homing endonuclease peptide

<400> SEQUENCE: 27

Leu Ala Gly Leu Ile Asp Ala Asp Gly
1               5
```

GENE EDITING FOR HIV GENE THERAPY

CROSS-REFERENCE TO RELATED APPLICATIONS

The present application claims the benefit of U.S. Provisional Application No. 62/029,037 filed Jul. 25, 2014; U.S. Provisional Application No. 62/036,511 filed Aug. 12, 2014; U.S. Provisional Application No. 62/042,059 filed Aug. 26, 2014; and U.S. Provisional Application No. 62/172,574 file Jun. 8, 2015, the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Aug. 17, 2015, is named 8325-0126SL.txt and is 11,569 bytes in size.

TECHNICAL FIELD

The present disclosure is in the field of genome engineering, particularly targeted modification with anti-HIV donors.

BACKGROUND

Human immunodeficiency virus (HIV)-1 is the causative agent of acquired immunodeficiency syndrome (AIDS). HIV-1 entry into target cells is initiated by a high-affinity binding of HIV-1 envelope gp120 glycoprotein to the primary receptor CD4, and the subsequent interaction of CD4-bound gp120 with the appropriate chemokine receptor (co-receptor), either CXCR4 or CCR5. See, e.g., Feng et al. (1996) *Science* 272:872-877; Deng et al. (1996) *Nature* 381:661-666. Most HIV strains are dependent upon the CD4/CCR5 receptor/co-receptor combination to gain entry into a cell and are termed CCR5 (or R5) tropic. Some viral strains however are dependent on the CD4/CXCR4 receptor/co-receptor combination and are termed CXCR4 (or X4) tropic, while others can utilize both the CD4/CCR5 and CD4/CXCR4 combinations and are termed dual (or R5/X4) tropic.

Recombinant transcription factors comprising the DNA binding domains from zinc finger proteins ("ZFPs") or TAL-effector domains ("TALEs") and engineered nucleases including zinc finger nucleases ("ZFNs"), TALENs, CRISPR/Cas nuclease systems, and homing endonucleases that are all designed to specifically bind to target DNA sites have the ability to regulate gene expression of endogenous genes and are useful in genome engineering and gene therapy, including in the inactivation of HIV receptors such as CCR5 and CXCR4. See, e.g., U.S. Pat. Nos. 9,045,763; 9,005,973; 8,956,828; 8,945,868; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 201000218264; 20120017290; 20110265198; 20130137104; 20130122591; 20130177983 and 20130177960 and 20150056705, the disclosures of which are incorporated by reference in their entireties for all purposes. Further, targeted nucleases are being developed based on the Argonaute system (e.g., from *T. thermophilus*, known as 'TtAgo', see Swarts et at (2014) *Nature* 507 (7491): 258-261), which also may have the potential for uses in genome editing and gene therapy. Nuclease-mediated gene therapy can be used to genetically engineer a cell to have one or more inactivated genes and/or to cause that cell to express a product not previously being produced in that cell (e.g., via transgene insertion and/or via correction of an endogenous sequence), thereby improving both the safety and efficiency with which HSC can be engineered. In particular, the use of engineered nucleases such as zinc finger nucleases (ZFNs), TALENs, TtAgo and CRISPR/Cas9 systems, provide the capability of precisely engineering specific genes. The nucleases act by creating double-stranded breaks (DSB) at a targeted DNA sequence, whose subsequent repair is then exploited to achieve one of three outcomes—gene knockout, gene mutation, or the site-specific addition (i.e. insertion or integration) of new genetic material (transgenes or fragments thereof) at the locus. For example, if DSB repair occurs through the error-prone NHEJ pathway, the result can be small insertions and/or deletions of nucleotides at the break site that thereby disrupt an open-reading frame.

Examples of uses of transgene insertion include the insertion of one or more genes encoding one or more novel therapeutic proteins, insertion of a coding sequence encoding a protein that is lacking in the cell or in the individual, insertion of a wild-type gene in a cell containing a mutated gene sequence, and/or insertion of a sequence that encodes a structural nucleic acid such as miRNA or siRNA. Examples of useful applications of mutation or 'correction' of an endogenous gene sequence include alterations of disease-associated gene mutations, alterations in sequences encoding splice sites, alterations in regulatory sequences, alterations in sequences to cause a gain-of-function mutation, and/or alterations in sequences to cause a loss-of-function mutation, and targeted alterations of sequences encoding structural characteristics of a protein. Transgene construct(s) is(are) inserted by either homology directed repair (HDR) or by end capture during non-homologous end joining (NHEJ) driven processes. See, e.g., U.S. Pat. Nos. 9,045,763; 9,005,973; 7,888,121 and 8,703,489.

Clinical trials using these engineered transcription factors and nucleases have shown that these molecules are capable of treating various conditions, including cancers, HIV and/or blood disorders (such as hemoglobinopathies and/or hemophilias). See, e.g., Yu et al. (2006) *FASEB J.* 20:479-481; Tebas et at (2014) *New Eng J Med* 370(10):901. Thus, these approaches can be used for the treatment of diseases.

Currently, the availability of highly active antiretroviral therapy (HAART) has transformed HIV infection into a chronic condition. However the associated costs, potential side-effects, and practical challenges of adhering to life-long drug regimens mean that alternative drug-free strategies to control HIV are needed. These include approaches based on genetically modifying cells to be HIV-resistant, either by directly engineering the CD4 T cells that HIV infects, or by targeting precursor cells including hematopoietic stem and progenitor cells (HSC) that give rise to these cells in vivo. See, e.g., U.S. Pat. Nos. 7,951,925 and 8,524,221 which describe nuclease-mediated inactivation of CCR5 in HSC at levels that proved sufficient to fully suppress HIV-1 replication in a humanized mouse model. Targeted integration of anti-HIV fusion proteins is described in U.S. Patent Publication No. 20120093787 and 20130171732.

Nonetheless, there remains a need for additional strategies of providing genetically modified cells for use in treatment and/or prevention of HIV.

SUMMARY

The present invention describes compositions and methods for use in gene therapy and genome engineering. Specifically, disclosed herein are methods and compositions for anti-HIV therapies. Despite the availability of CCR5 disruption as an anti-HIV therapy, further compositions and methods are desirable inasmuch as (i) cells with only a single allele (CCR5) disrupted will not become fully resistant to HIV, and (ii) alternative approaches to CCR5-only disruption will be needed to inhibit dual or X4-tropic viruses. Accordingly, described herein are alternate and complementary approaches, including introduction of mutations and/or a "donor" (transgene) following DNA cleavage. For instance, the DNA break can be repaired instead using the cell's homology directed repair (HDR) pathways, where information is copied from a homologous 'donor sequence' that is also introduced into the cell. The repair template can be designed to achieve small mutations close to the break site, or to promote the highly regulated insertion of new genetic material at the DSB. To this end, also described herein are methods of enhancing HDR-mediated gene editing at levels, for example such that at least or over 50% of cells (including primitive stem cell populations), including any percent above such as 55%, 60%, 65%, 70%, 80%, 85%, 90%, 95%, 100% or any value therebetween (e.g., human HSCs) are modified. This unprecedented capability allows the expanded use of targeted nucleases beyond CCR5 gene knockout, and the development of novel approaches to HIV gene therapy based on either in situ editing of endogenous human genes (e.g., antiviral genes including restriction factors as defined below), or the precise knock-in of broad spectrum anti-HIV genes at the CCR5 locus, or the precise knock-out or modification of pro-HIV genes. Suitably "weaponized" cells (e.g., stem cells such as induced pluripotent stem cells or hematopoietic stem cells, or other cells such as T-cells) carrying precise genetic additions that offer the potential for cross-clade HIV resistance in the transplanted immune system provide the potential for an immunological "cure" for HIV, i.e. via the introduction of the engineered stem cells into an individual that would have the ability to mount and sustain an anti-HIV response. Use of the subject's own cells eliminates the requirement of HLA matching between donor and recipient for the transplant. In addition, such nuclease-modified cells retain their modification such that these nuclease-modified cells can also be obtained from primary subjects (e.g., subjects into which nuclease-modified cells are introduced) and administered in a secondary transplantation to a secondary subject.

In one aspect, described herein is a method of generating a cell that will not sustain HIV infection, the method comprising genetically modifying the cell such that: (i) an endogenous restriction factor (e.g., TRIM5a, APOBEC3G, or tetherin) is modified to increase its activity against HIV; (ii) an endogenous viral host factor (e.g., LEDGF/p75 (PSIP1), FPSF6, Nup358 and/or TNP03) is modified to decrease its activity in response to HIV infection; and/or (iii) an exogenous transgene encoding an Trim5α-Cyp fusion protein is inserted into an endogenous safe harbor locus (e.g., CCR5, AAVS1, or HPRT), such that the cell will not sustain HIV infection. In certain embodiments, the modification of the endogenous viral restriction factor comprises introduction of one or more point mutations in the endogenous gene sequence to alter the amino acid sequence of the encoded restriction factor or introduction of a sequence encoding a functional domain (e.g., a protein that recognizes an HIV capsid protein such as cyclophilin A (CypA) peptide) such that the sequence encoding the functional domain is operably linked to the endogenous sequence encoding the restriction factor. In certain embodiments, the amino acids modified are R332 and R335 in TRIM5a; or S128 in APOBEC3G; and/or L41 and T45 in tetherin. In other embodiments, the modification of an endogenous viral host factor comprises introduction of mutations knock out (inactivation of) the expression of the endogenous viral host factor. In any of the methods described herein, the modification is made using a nuclease (e.g., a ZFN, TALEN, CRIPSR/Cas system or TtAgo system). Also provided are methods of treating and/or preventing HIV infection in a subject by administering a cell generated as described herein to the subject, thereby treating and/or preventing HIV infection in the subject. Also provided are methods of providing genetically modified cells to a subject in need thereof, the method comprising: administering a cell produced by the method of claim 1 to a first subject; harvesting bone marrow from the first subject; administering the bone marrow to a second subject such that the genetically modified cells are engrafted in the subject in need thereof.

In another aspect, described herein are compositions comprising one or more of the nucleases (ZFNs, TALENs, TtAgo and/or CRISPR/Cas systems) described herein. In certain embodiments, the composition comprises one or more nucleases in combination with a pharmaceutically acceptable excipient. In some embodiments, the composition comprises two or more sets (pairs) of nucleases, each set with different specificities. In other aspects, the composition comprises different types of nucleases. In some embodiments, the composition comprises polynucleotides encoding nucleases, while in other embodiments, the composition comprises nuclease proteins. In still further embodiments, the composition comprises one or more donor molecules. In certain embodiments, the nuclease(s) target(s) a safe-harbor gene such as CCR5 and/or AAVS1. In other embodiments, the nuclease(s) target(s) an endogenous cellular restriction factor gene (e.g., TRIM5α, APOBEC3G, tetherin (also referred to as "BST-2") or the like). In certain embodiments, the nuclease(s) target(s) an intron of an endogenous gene (e.g., intron 6 or 7 of TRIM5α, intron 2 or 3 of APOBEC3G, or intron 1 of tetherin). In certain embodiments, the nuclease(s) target(s) an exon of an endogenous gene (e.g., exon8 of TRIM5α, exon 3 of APOBEC3G, or exon 1 of tetherin). In preferred embodiments, the nucleases target the TRIM5α gene sequences and result in modification of the sequence that encodes the amino acids R332 and R335. In further preferred embodiments, the nucleases target the APOBEC3G sequences and modify the sequence that encodes amino acid S128. In yet other preferred embodiments, the nucleases target the gene sequences in BST-2 that encode amino acids L41 and T45. In some embodiments, the nuclease(s) target(s) a gene whose product is known to support or enhance HIV infection. Non-limiting examples of these genes include LEDGF/p75 (PSIP1) which helps HIV to integrate at favorable/active regions of the chromatin (see Maertens et al. (2003) *J Biol Chem.* 278(35):33528-39) and CPSF6 (see Price et al. (2012) *PLoS Pathog.* 8(8)) Nup358 (see Schaller et al. (2011) *PLoS Pathog.* 7(12):e1002439) and TNP03 (see Brass et al. (2008) Science. 319(5865):921-6) all three of which are all involved in nuclear import of the virus. In some embodiments, the nuclease(s) target(s) genes whose products have the potential to inhibit HIV infection if mutated in sequence, for example APOBEC (A-H), SAMHD1, Viperin, SLFN11. In some embodiments the nuclease(s) target(s) the regulatory regions of genes whose products have the potential to inhibit HIV infection if expressed in an HIV target cell, for example CD4 T cells, macrophages or microglia, for example by modifying a control element (e.g., promoter) such that the gene is switched on or off to confer anti-HIV activity to a cell.

In another aspect, described herein is a polynucleotide encoding one or more nucleases (e.g., ZFNs, TALENs, TtAgo or CRISPR/Cas system) described herein. The polynucleotide may be, for example, mRNA or DNA. In some aspects, the mRNA may be chemically modified (See e.g. Kormann et al, (2011) *Nature Biotechnology* 29(2):154-157). In other aspects, the mRNA may comprise an ARCA cap (see U.S. Pat. Nos. 7,074,596 and 8,153,773). In further embodiments, the mRNA may comprise a mixture of unmodified and modified nucleotides (see U.S. Patent Publication 2012-0195936). In some embodiments, the mRNA is delivered to the cell via a lipid nanoparticle (LNP). In another aspect, described herein is a nuclease expression vector comprising a polynucleotide, encoding one or more ZFNs, TALENs, TtAgo or CRISPR/Cas systems described herein, operably linked to a promoter. In one embodiment, the expression vector is a viral vector, for example an AAV vector, lentiviral vector and/or adenoviral vector In another aspect, described herein are genetically modified cells generated by any of the methods described herein, including stem cells such as hematopoietic stem cells (HSCs) or iPSCs as well as cells descended from the genetically modified cells as described herein. Compositions comprising the cells as described herein (including cells descended from the genetically modified cells) are also provided. In certain embodiments, the host cell comprises one or more nucleases and/or nuclease expression vectors as described herein. The host cell may be stably transformed or transiently transfected or a combination thereof with one or more nuclease expression vectors. In certain embodiments, the cells are hematopoietic stem cells (HSCs), for example a human HSC. In other embodiments, the one or more nuclease expression vectors express one or more nucleases in the host cell. In another embodiment, the host cell may further comprise an exogenous polynucleotide donor sequence. In any of the embodiments, described herein, the host cell can comprise an embryo cell, for example a one or more mouse, rat, rabbit or other mammal cell embryo (e.g., a non-human primate). In some embodiments, the host cell comprises a tissue. Also described are cells or cell lines descended from the cells described herein, including pluripotent, totipotent, multipotent or differentiated cells comprising a modification (e.g., integrated donor sequence) as described herein. In certain embodiments, described herein are differentiated cells comprising a modification a modification (e.g., modified restriction factor gene, modified host factor gene and/or integrated donor sequence) in which differentiated cells are descended from a stem cell as described herein.

In any of the compositions and methods described herein, the donor sequence may encode a functional protein (e.g., fusion protein) and/or may include a repair template that is integrated at or near the site to cleavage to modify and/or repair an endogenous sequence (e.g., introduce one or more point mutations). In some embodiments, the donor sequence comprises a sequence encoding the entry inhibitor peptide C46, expressed as both cell surface—anchored and secreted molecules; a humanized TRIM-Cyp fusion protein (or a Cyp protein that is expressed as a fusion with an endogenous TRIM protein (see, e.g., U.S. Pat. Nos. 8,748,372 and 8,084,593), which serves as a potent intracellular restriction factor, and/or a dual-specificity soluble CD4/CCR5-mimetic peptide (e.g., eCD4-IgG) that inhibits a broad spectrum of HIV isolates. In certain embodiments, the anti-HIV transgene or a portion thereof is integrated into exon 8 of TRIM5α, for instance a Cyp gene is integrated into an endogenous TRIMα gene such that a TRIMα-Cyp fusion is produced from the endogenous gene (e.g., into exon 6, 7, or 8 or intron 7). In other embodiments, the donor comprises a sequence capable of in situ editing of human restriction factors to provide modified versions of these restriction factors which exhibit anti-HIV activity, (e.g., TRIM5α, APOBEC3G and/or BST-2), or impair HIV supportive genes (e.g., LEDGF/p75 (PSIP1), CPSF6, Nup358 and TNP03) in order to create anti-HIV capabilities in human HSPC and their progeny.

Furthermore, the donor sequence may be present in the nuclease delivery system (e.g., non-viral vector or viral vector), present in a separate delivery mechanism (e.g., nuclease delivered in mRNA form and donor delivered using viral vector such as AAV, IDLV or the like) or, alternatively, may be introduced into the cell using a separate and/or different nucleic acid delivery mechanism. Insertion of a donor nucleotide sequence into an endogenous locus (e.g., CCR5 or AAVS1) can result in the expression of the transgene under control of the endogenous genetic control elements. In some aspects, insertion of the transgene of interest results in expression of an intact exogenous protein sequence and lacks any endogenous-encoded amino acids. In other aspects, the expressed exogenous protein is a fusion protein and comprises amino acids encoded by the transgene and by the endogenous gene. In some instances, the endogenous sequences will be present on the amino (N)-terminal portion of the exogenous protein, while in others, the endogenous sequences will be present on the carboxy (C)-terminal portion of the exogenous protein. In other instances, endogenous sequences will be present on both the N- and C-terminal portions of the exogenous protein.

In some embodiments, the invention describes methods and compositions that can be used to express a transgene under the control of an endogenous promoter in vivo. In some aspects, the transgene may encode a therapeutic protein of interest and/or a template for modification of an endogenous gene. The transgene may encode a protein such that the methods of the invention can be used for protein replacement. In some aspects, the transgene encodes an anti-HIV protein that treats and/or prevents HIV infection.

In another aspect, a method of generating a cell as described herein is provided, the method comprising administering to the cell one or more polynucleotides encoding one or more nucleases (e.g., ZFNs, TALENs, TtAgo, CRISPR/Cas system) such that the nuclease mediates modification of the endogenous gene, for example in the presence of one or more donor sequence, such that the donor is integrated into the endogenous gene targeted by the nuclease. Integration of one or more donor molecule(s) occurs via homology-directed repair (HDR) or by non-homologous end joining (NHEJ) associated repair. In certain embodiments, one or more pairs of nucleases are employed, which nucleases may be encoded by the same or different nucleic acids. Any endogenous gene can be targeted for nuclease-mediated targeted integration of a donor, including but not limited to a safe-harbor gene such as CCR5, AAVS1, Rosa26, ALB and/or HPRT. In some embodiments, the donor comprises a splice acceptor site.

In yet another aspect, provided herein is a cell comprising a genetic modification as described herein. In certain embodiments, the genetic modification comprises modification of an endogenous restriction factor gene, modification of an endogenous viral host factor and/or integration of a transgene. The genetic modifications may be introduced using a nuclease. In certain embodiments, the cell is made by the methods described herein. In other embodiments, a transgene (Trim5α-Cyp fusion) is integrated into a safe-harbor locus, such as CCR5, AAVS1, ALB, Rosa26 and/or HPRT. In other embodiments, an endogenous locus encoding a restriction factor is modified (e.g., via point mutation(s) and/or integration of transgene), such that expression of the endogenous restriction factor is modified. In any of the cells described herein, an intronic region of a gene (e.g., intron 6 or 7 of TRIM5α, intron 2 or 3 of APOBEC3G or intron 1 of tetherin) may be modified. In some embodiments, the integrated donor sequence comprises cDNA sequences and/or an incomplete gene sequence (e.g., a "half gene" sequence) where a partial (incomplete) gene sequence is inserted into the insertion site such that the endogenous promoter and transcriptional start site drive expression of a complete gene. In certain embodiments, the cell comprises a descendant of a cell as described herein, for example, an HSC obtained from a primary subject (non-human mammal such as mouse or primate), which HSC was ZFN-modified prior to administration into the primary subject and/or an HSC obtained from a secondary subject (e.g., HSCs obtained from a subject which received HSCs from a primary subject). For example, in a gene with a mutation towards the 3' end of the gene, the portion of the gene with the mutation is replaced with a transgene that encodes a wild-type gene and, optionally, a poly A sequence such that transcription (from the endogenous promoter and start site) stops at the end of the inserted sequence and the mutated part of the gene is not transcribed. In some embodiments, the integrated donor sequence comprises a splice acceptor sequence such that following integration into an intron, the coding sequences of the donor will be linked to the coding sequences of the endogenous gene after transcription and mRNA processing. The cells comprising an integrated donor may express the transgene from an endogenous promoter (alone or as a fusion with an endogenously expressed sequence, for example a Cyp-encoding transgene that is expressed with endogenously expressed TRIM5α as a TRIM5α-Cyp fusion protein) or, alternatively, the transgene may include regulatory and control elements such as exogenous promoters that drive expression of the transgene. In certain embodiments, the cells do not include any viral vector sequences integrated into the genome. In certain embodiments, the cells do not include any exogenous sequences other than the anti-HIV transgene or active fragment thereof.

In some aspects, the invention includes methods and compositions for introducing specific known mutations into an endogenous gene. In some embodiments, the introduced mutation results in a loss-of-function of the targeted endogenous gene. In other embodiments, the introduced mutation results in a gain-of-function in the targeted endogenous gene. In some aspects, donor oligonucleotides are used to create the targeted mutation. The donor oligonucleotides may comprise the sequence of the intended mutation flanked by homology arms. In some aspects, the homology arms are 10-100 nucleotides, while in other aspects, the homology arms are 750 nucleotides or more. The endogenous gene is targeted with the nucleases of the invention at or near the specific location where the mutation(s) is(are) to be introduced, in either the exon and/or an intron. The creation of the DSB by the nucleases of the invention stimulates HDR such that the mutation is introduced into the endogenous gene.

In any of the methods and compositions described herein, the cells may be any eukaryotic cell, including but not limited to human or non-human stem cells, precursor cells or somatic cells such as T-cells. In certain embodiments, the cells are HSCs. Any of the cells described herein may be patient-derived, for example autologous CD34+ stem cells (e.g., mobilized in patients from the bone marrow into the peripheral blood via granulocyte colony-stimulating factor (GCSF) administration, or harvested directly from the patient's bone marrow). The CD34+ cells can be harvested, purified, cultured, and the nucleases and/or donor (e.g., an adenoviral vector donor) introduced into the cell by any suitable method.

In another aspect, the methods and compositions of the invention provide for the use of cells, cell lines and animals (e.g., transgenic animals) in the screening of drug libraries and/or other therapeutic compositions (i.e., antibodies, structural RNAs, etc.) for use in treatment or prevention of HIV, including generating a cell that does not sustain HIV infection. Such screens can begin at the cellular level with manipulated cell lines or primary cells, and can progress up to the level of treatment of a whole animal (e.g., human). Thus, in certain aspects, described herein is a method of treating and/or preventing HIV in a subject in need thereof, the method comprising administering one or more nucleases, polynucleotides and/or cells as described herein to the subject. In certain embodiments, a cell as described herein (e.g., a genetically modified cell) is administered to the subject. In any of the methods described herein, the cell may be a stem cell derived from the subject (patient-derived stem cell), or may be a stem cell derived from an autologous donor.

In any of the compositions and methods described herein, the nucleases are introduced in mRNA form and/or using one or more non-viral or viral vector(s). In certain embodiments, the nuclease(s) are introduced in mRNA form. In other embodiments, the transgene is introduced using a viral vector, for instance an adeno-associated vector (AAV) including AAV1, AAV3, AAV4, AAV5, AAV6, AAV8, AAV 8.2, AAV9, AAV rh10, AAV2/8, AAV2/5 and AAV2/6, or engineered AAV vectors (e.g. modified to alter tropism or immunoreactivity), or via a lentiviral or integration-defective lentiviral vector, and the nuclease(s) is(are) introduced in mRNA form. In preferred embodiments, the nuclease is introduced as mRNA and the donor is introduced via an AAV6-based vector. In any of the compositions and methods described herein, the percent of cells of a population (or alleles) comprising an inserted transgene is at least 50%. In some aspects, the percent of cells of a population (or alleles) comprising an inserted transgene is greater than 50%, including 55%, 60%, 65%, 70%, 75%, 80%, 85%, 90%, 95% or greater. In still further embodiments, the nuclease(s) and donors are both introduced using one or more viral or non-viral vectors. The nuclease and donor may be carried on the same vector, on different vectors of the same type or on different vectors of different types. In certain embodiments, the nuclease(s) is(are) introduced in mRNA form (e.g., via electroporation) and the donor is introduced using an AAV (e.g., AAV6), lentivirus or integration defective lentivirus. In certain embodiments the donor is introduced as single-stranded DNA and/or in minicircle form.

The donor may be delivered to any cell and integrated at any suitable gene. In certain embodiments, the endogenous gene is a gene encoding a factor (e.g., restriction factor) involved in HIV infection. In other embodiments, the nuclease targets a safe harbor gene such as HPRT, CCR5, AAVS1, Rosa26, ALB or the like.

Any cell can be modified using the compositions and methods of the invention, including but not limited to prokaryotic or eukaryotic cells such as bacterial, insect, yeast, fish, mammalian (including non-human mammals), and plant cells. In certain embodiments, the cell is an immune cell, for example a T-cell (e.g., CD4+, CD3+, CD8+, etc.), a dendritic cell, a B cell or the like. In other embodiments, the cell is a pluripotent, totipotent or multipotent stem cell, for example an induced pluripotent stem cell (iPSC), hematopoietic stem cells (HSC, e.g., CD34+), an embryonic stem cell or the like. In any of the methods or compositions described herein, the cell containing the donor can be a stem or progenitor cell. In some aspects, long term stem cells (LT-HSC) are preferentially modified. In some embodiments, primitive stem cells in the CD34+ pool are preferentially modified. In some aspects, these primitive stem cells are CD34+, CD133+, CD90-high. In some aspects, these primitive stem cells are also CD38- and CD49f-high. Specific stem cell types that may be used with the methods and compositions of the invention include embryonic stem cells (ESC), induced pluripotent stem cells (iPSC) and hematopoietic stem cells (e.g., CD34+ cells). The iPSCs can be derived from patient samples and from normal controls wherein the patient derived iPSC can be mutated to the normal or wild type gene sequence at the gene of interest, or normal cells can be altered to the known disease allele at the gene of interest. Similarly, the hematopoietic stem cells can be isolated from a patient or from a donor. These cells are then engineered as described herein, expanded and then reintroduced into the patient. In certain embodiments, the cell is a patient derived hematopoietic stem cell. In other embodiments, the cell is a COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NSO, SP2/0-Ag14, HeLa, HEK293 (e.g., HEK293-F, HEK293-H, HEK293-T), and perC6 cells.

In some embodiments, the methods and compositions of the invention provide materials useful for editing a cell in situ within a subject in need thereof. Non-limiting examples of these materials include virus and nanoparticles for delivery of the compositions (e.g., nucleases and/or donors) directly to a tissue. In some aspects, the tissue is a secretory tissue such a liver, while in other aspects, the tissue has specific function such as bone marrow or lung.

A kit, comprising the nucleic acids, proteins and/or cells of the invention, is also provided. The kit may comprise nucleic acids encoding the nucleases, (e.g. RNA molecules or ZFN, TALEN, TtAgo or CRISPR/Cas system encoding genes contained in a suitable expression vector), or aliquots of the nuclease proteins, donor molecules, suitable stemness modifiers, cells, instructions for performing the methods of the invention, and the like.

In another aspect, provided herein is a method of providing genetically modified cells to a first subject in need thereof, the method comprising genetically modifying stem cells using one or more nucleases; and administering the genetically modified stem cells to the subject such that the stem cells engraft in the first subject. In certain embodiments, the genetic modification comprises nuclease-mediated targeted integration of an exogenous sequence encoding a protein (e.g., anti-HIV protein as described herein); wherein the stem cells engraft in the first subject and produce the protein upon differentiation in the first subject. In certain embodiments, the stem cells are hematopoietic stem cells. In other embodiments, the sequence encoding the protein is carried on an AAV6 vector.

In still further aspects, methods of serial (secondary) transplantation are provided. In certain aspects, the method comprise harvesting bone marrow from a first subject who has previously been provided with genetically modified cells; and administering the bone marrow to a second subject such that the genetically modified cell is engrafted in the second subject. In certain embodiments, the genetically modified cell produces a protein in the second subject. In certain embodiments, the stem cells are hematopoietic stem cells (e.g., LT-HSCs).

These and other aspects will be readily apparent to the skilled artisan in light of disclosure as a whole.

BRIEF DESCRIPTION OF THE DRAWINGS

FIG. 5 includes a schematic depicting the introns and exons in the APOBEC3G gene and indicating the approximate location of residue D128: an example of a residue in exon 3 whose mutation to lysine renders the protein resistant to HIV-1 Vif-mediated degradation. Also shown is a partial sequence of genomic APOBEC3G (SEQ ID NO: 8) including introns 2 and 3 (shown in italics) which includes sequences that could be targeted by nucleases. The location of the codon for residue D-128 is indicated in exon 3 (bolded), in larger font. Illustrative examples of nucleotides in introns 2 and 3 that may be splicing regulatory sequences and are to be avoided as target sites for nucleases are underlined, and include the splice donor and acceptor sites (boxed).

FIG. 8A is an illustration of AAV6 donor viruses that were used for insertion of the transgene (GFP) into either the AAVS1 or CCR5 safe harbor loci by virtue of containing flanking sequences homologous to either of these loci. FIG. 8A also shows the percent of HSC (top right corner of each panel) that are GFP positive due to site-specific insertion of the GFP cassette at either the CCR5 or AAVS1 loci, as determined by FACS analysis, following co-administration of mRNAs encoding the indicated ZFNs targeting either CCR5 or AAVS1. When the CCR5-GFP AAV vector donor is used, 'matched' ZFNs are targeted to CCR5, while 'mismatched' ZFNs are targeted to AAVS1. For the AAVS1-GFP AAV vector, only the combination with matched AAVS1 targeted ZFNs are shown. FIG. 8B shows two gels verifying the targeted insertion of the GFP transgene into either the CCR5 (left side) or AAVS1 (right side) safe harbor loci only when matched ZFNs are also present, determined using qPCR to detect a specific band ("HDR") in HSC cultures 10 days following electroporation. FIG. 8C is a graph depicting the percent of GFP expression in the indicated sub-pools within the bulk CD34+ cell population, treated with CCR5-GFP AAV donor and CCCR5 ZFNs. FIG. 8D is a table showing the percentage of modifications at the CCR5 locus in CD34+ HSC treated with CCR5-GFP AAV donor and CCR5 ZFNs, either as disruption by NHEJ (% CCR5 disruption) or by the percent of loci comprising the targeted insertion of the transgene (HDR events) as determined by MiSeq analysis. Also shown are the % of cells that were GFP+ by FACS. These cells were used to transplant mice, and FIG. 8E depicts FACS analysis of the transgene GFP expression in the blood of 4 mice receiving these edited HSC 16 weeks post engraftment. FIG. 8F shows qPCR analysis of the bone marrow (BM) and spleen tissue in the same four engrafted mice and indicates that each comprises successful targeted insertion of the GFP transgene.

FIG. 9C shows a gel that depicts site-specific insertion of the exogenous GFP sequence at the CCR5 locus via homology-directed repair (HDR) as determined by qPCR in blood and bone marrow ("BM") from humanized mice 16 weeks after engraftment with HSCs, which HSCs were treated with the CCR5 ZFNs and CCR5-GFP AAV6 donors ("HDR"). A control qPCR is also shown ("ctrl").

FIGS. 11A through 11D depict efficient transduction of HSCs by AAV6. FIGS. 11A and 11B show results of mobilized blood CD34+ HSC transduced with increasing doses of GFP-expressing AAV vectors of the indicated serotypes and FIGS. 11C and 11D shows results of fetal liver CD34+ HSC transduction. GFP expression was determined at 2 days (fetal liver) or 3-5 days (mobilized blood) post-transduction by flow cytometry. The vector panel for each cell type were from independent manufacturing sources, and the doses used were $1\times10^3$, $3\times10^3$, $1\times10^4$, $3\times10^4$ and $1\times10^5$ vector genomes (vg)/cell for mobilized blood HSC, and $1\times10^2$, $5\times10^2$, $1\times10^3$, $5\times10^3$ and $1\times10^4$ vg/cell for fetal liver HSC. FIGS. 11A and 11C show data from representative experiments at doses of $1\times10^4$ vg/cell. FIGS. 11B and 11D show the mean data+/−SD from 2 (mobilized blood) and 3 (fetal liver) experiments using independent HSC donor sources.

FIG. 12A is a schematic showing use of an AAV vector as a donor template for homology directed repair (HDR) of a double-strand break (DSB), as induced by target-specific nucleases. FIG. 12B is a schematic depicting AAV vector genomes containing CCR5 homology donors. R and L refer to CCR5 genomic sequences, comprising 1431 and 473 base pairs respectively. FIG. 12C is a graph depicting the percent genome modification in mobilized blood CD34+ HSC transduced with AAV6 vectors carrying the CCR5-RFLP donor at indicated doses (vg/cell) for 16 hours, then electroporated with CCR5 ZFN mRNA (120 μm/ml). Cells were analyzed 3-5 days post-electroporation by deep sequencing to measure the efficiency of genome modification (% "indels" (insertions and/or deletions) and specific insertion of an Xho1 sequence "RFLP"). Results from a representative of 3 experiments using 3 different HSC donors are shown. FIG. 12D depicts RFLP assay confirmation of dose-dependent insertion of XhoI site at CCR5. FIG. 12E is a graph depicting GFP expression in mobilized blood HSC treated using CCR5-GFP donor AAV vectors, with and without CCR5 ZFN mRNA electroporation. Cells were collected 3-6 days post-transduction and analyzed by flow cytometry for % GFP+. Results were combined from 5 experiments using 4 different donors and show mean+/− SD. FIG. 12F shows flow cytometry plots from one representative experiment using 3,000 vg/cell CCR5-GFP donor, at 6 days post-electroporation, without (left) and with CCR5 ZFNs. FIG. 12G shows gel results confirming targeted integration of GFP expression cassette at the CCR5 locus by semi-quantitative PCR. The % HDR was estimated by comparison to standards. FIG. 12H is a graph depicting gene editing with AAV6 vectors and ZFN mRNA at the CCR5 locus in fetal liver CD34+ HSC. Fetal liver CD34+ HSC were transduced with AAV6-CCR5-GFP donor (1,000 vg/cell) for 24 hours then electroporated with CCR5 ZFN mRNA (grey boxes) or mock electroporated (white boxes). Cells were analyzed at days 1 and 10 post electroporation by flow cytometry. The graph shows the mean+/−SD for flow cytometry data from 4 independent experiments.****$p<0.0001$, one-way ANOVA, Newman-Keuls post-test to compare all columns.

FIG. 13A is a schematic showing the AAV vectors used. Only vector CCR5-GFP contained homology to the CCR5 locus. FIG. 13B shows flow cytometry plots of fetal liver HSC transduced with 1,000 vg/cell of the indicated AAV vectors for 24 hours, then electroporated with CCR5 ZFN mRNA. Cells were analyzed for GFP by flow cytometry at day 1 and day 10 post-electroporation. The numbers in the upper right of each plot indicate % GFP positive cells. Shown is data from one representative experiment. FIG. 13C confirms targeted integration of GFP at the CCR5 locus by semi-quantitative PCR, for one representative experiment. FIG. 13D is a graph depicting mean+/−SD GFP+ expression by flow cytometry at day 1 and day 10, from n=2 fetal liver tissues.

FIG. 14A is a graph showing results of colony formation (CFU) assays initiated 24 hours post-electroporation and evaluated 14 days later for the indicated colony types. The left-most bar shows mock transductions. The bar $2^{nd}$ from the left in each group shows cells administered CCR5-ZFNs only. The bar $2^{nd}$ from the right in each group showings cells administered CCR5-RFLP AAV donors and the right-most bar shows cells administered CCR5-RFLP donors and CCR5-ZFNs (CCR5-RFLP+ZFN). Mean+/−SD from duplicated samples are shown. No significant differences were detected among the 4 treatment conditions ($p>0.05$, one-way ANOVA). FIG. 14B shows results of genotyping CFUs by deep sequencing to detect rates of insertion of the XhoI site at CCR5. Between 23 and 88 validated individual colonies were picked for each colony type. Mean+/−SD from 2 combined experiments using different HSC donors are shown. No significant differences were detected ($p>0.05$, one-way ANOVA).

FIG. 15A shows representative FACS plots showing different subsets within the CD34+ population. This includes the most primitive long-term (LT) HSC population. FIG. 15B shows FACS plots at day 7 showing GFP expression in unsorted bulk CD34+ population and sorted sub-sets. FIG. 15C is a graph showing mean+/−SD GFP+ cells treated under the indicated conditions as detected by flow cytometry at day 7, for n=3 independent CD34+ sources.*$p<0.05$, unpaired t-test; $p>0.05$ between all ZFN treated groups, one-way ANOVA. FIG. 15D shows results of semi-quantitative PCR showing levels of GFP insertion at the CCR5 locus in indicated subsets. FIG. 15E shows representative FACS plots (at day 7) using the experimental approach described above but using AAVS1-GFP AAV vector donor and AAVS1 ZFN mRNA. FIG. 15F is a graph showing mean+/−SD GFP+ cells detected by flow cytometry at day 7, for n=3 independent CD34+ sources treated with AAVS1-GFP donor and AAVS1 ZFNs. $p>0.05$ between all groups, one-way ANOVA. FIG. 15G shows PCR results detecting GFP insertion at the AAVS1 locus in indicated subsets.

FIG. 16A depicts engraftment in neonatal NSG mice with fetal liver HSC, either mock treated or treated with AAV6 donors (CCR5-GFP or CCR5-RFLP) and CCR5 ZFN mRNAs. Peripheral blood was analyzed at weeks 8, 12, and 16 post-engraftment for frequency of human CD45+ cells, as well as bone marrow and spleen at 16 weeks. There was no significant difference between mock and treated samples for engraftment in the blood or tissues (two-way ANOVA). FIG. 16B shows gene modification in human cells as measured in mouse blood and tissue (bone marrow and spleen) samples by GFP+ flow cytometry (for CCR5-GFP donor samples) or deep sequencing for RFLP insertions (for CCR5-RFLP donor samples). (na, not available). Shown is combined data from 2 separate cohorts of mice engrafted from 2 separate treated donor sources of HSC. FIG. 16C is a graph showing the percent positive cells under the indicated conditions. Bone marrow was isolated at 16 weeks post-engraftment from 2 mice each from the CCR5-GFP or CCR5-RFLP cohorts and pooled, and the combined levels of human CD45+ cells and gene modification (GFP+ or RFLP, by FACS or deep sequencing, respectively) was measured in the pooled cell population. These pooled cell populations were used to engraft adult NSG mice and, 20 weeks later, bone marrow was isolated from the secondary transplant recipients and analyzed for human CD45+ content and levels of gene modification in the same way. FIG. 16D depicts that gene edited cells are present in different lineages. Neonatal NSG mice were engrafted with fetal liver HSC, treated with CCR5-GFP vectors and CCR5 ZFN mRNAs. Peripheral blood was analyzed by flow cytometry at 8, 12, and 16 weeks for GFP levels in each indicated human cell lineage. At the 16 week time point, bone marrow was similarly analyzed for GFP expression. No significant differences were noted in levels of % GFP+ cells between lineages except in the bone marrow, where levels of GFP+ cells in the CD4+ T cell fraction were significantly higher than other cell types ($p<0.05$, one-way ANOVA, Newman-Keuls posttest to compare all cell types). FIG. 16E shows combined data from 4 animals at each time point. FIG. 16E depicts representative plots of GFP+ cells in indicated lineages from blood of 2 different mice.

DETAILED DESCRIPTION

Figure 1:
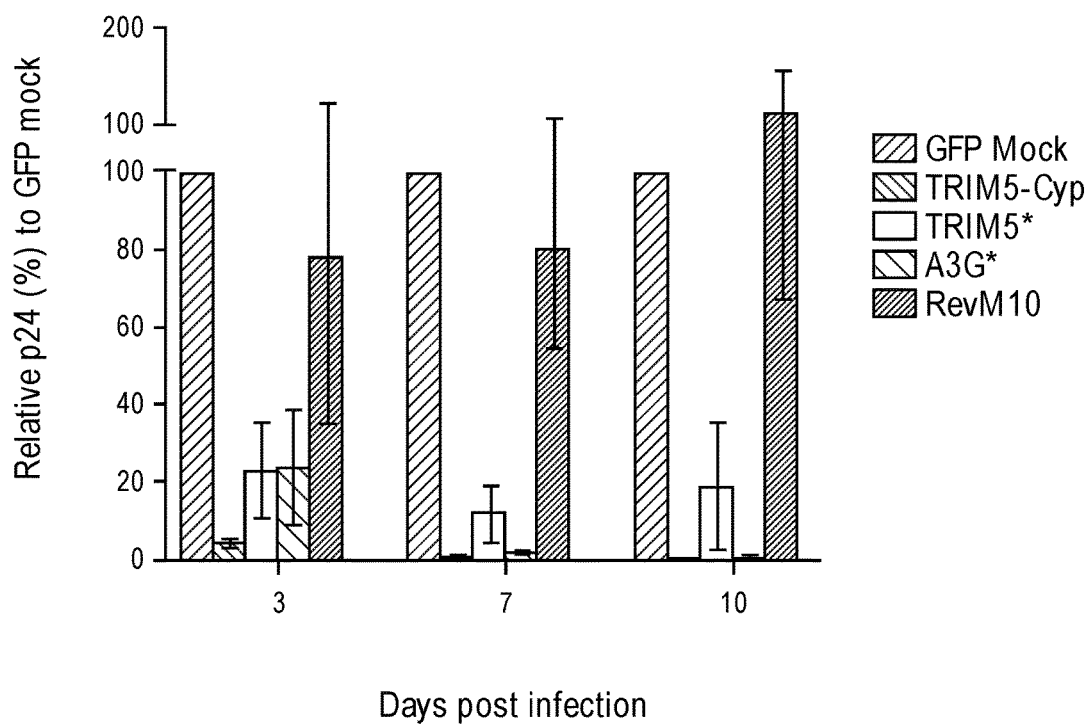
FIG. 1 is a graph showing relative production of HIV, measured as antigen p24 secreted from cells expressing the indicated genes following their introduction via lentivirus in Jurkat cells. Expression of p24 is normalized to the levels produced from the control population (GFP Mock, cells transduced with a lentivirus only expressing GFP). The left most bar of each panel shows relative p24 expression from GFP-mock transductions; the bar second from the left of each group shows p24 expression from cells expressing a TRIM5-Cyp fusion protein; the middle bar of each group shows p24 expression from cells expressing a TRIM5α protein with a point mutation (R332P); the bar second from the right in each group shows p24 expression from cells expressing a APOBEC3G (A3G) protein with a point mutation (D128K); and the right most bar of each group shows p24 expression in cells expressing a RevM10 protein. "*" indicates form of the protein comprising a point mutation introduced to confer anti-HIV-1 activity. Each lentiviral vector also expressed GFP and the transduced cell populations were FACS sorted to be 100% GFP+, and the cultures were challenged with HIV-1 (strain NL4-3). Virus levels (p24 antigen in supernatant) were measured at 3, 7 and 10 days later and shown relative to the Mock (GFP only lentiviral vector) population.

Disclosed herein are compositions and methods for genetic modification of cells (e.g., HSCs), including for the treatment and/or prevention of HIV. Described herein is the site-specific addition of donor molecules (e.g., donors comprising anti-HIV genes), for example into one or more safe-harbor genes, such as the CCR5 and/or AAVS1 loci. When targeting the CCR5 locus, this will provide a combinatorial anti-HIV therapy with extended activity against both R5 and X4-tropic viruses. Anti-HIV genes include, but are not limited to, (i) the entry inhibitor peptide C46, expressed as both cell surface anchored and secreted molecules, (ii) a humanized TRIM-Cyp fusion protein, which serves as potent intracellular restriction factors, and (iii) a dual-specificity soluble CD4/CCR5-mimetic peptide (eCD4-IgG) that inhibits a broad spectrum of HIV isolates. Constitutive, T cell restricted, interferon-inducible, HIV-inducible and CCR5-promoter expression strategies are compared. The anti-HIV transgenes may be delivered, for example, using AAV vectors (e.g., AAV6), integrase-defective lentiviral vectors (IDLVs), and/or nucleic acids including plasmids, minicircle plasmids and oligonucleotides. As described herein, AAV delivery of the DNA repair template (including a transgene) supports efficient homology-driven gene addition.

Also described herein, is precise in situ editing of human restriction factors, in order to create anti-HIV capabilities in human HSC and their progeny. Part of HIV's success as a human pathogen is due to the fact that it circumvents the action of components of the cell-autonomous innate immune system, including the restriction factors TRIM5α, APOBEC3G and BST-2. These intracellular proteins directly inhibit various stages of the viral life-cycle and, in the case of TRIM5α and BST-2, also trigger additional anti-viral responses. However, HIV-1 is generally susceptible to orthologs of these proteins in non-human primates, highlighting and allowing specific mutations to be mapped that can restore anti-HIV activity to the human factors. Nuclease-mediated introduction of such mutations in situ into the endogenous genes for these factors in human HSC confers HIV-resistance and/or sensing capabilities to the progeny of the edited cells. Additionally, specific knock out or mutation of HIV supportive genes (e.g. LEDGF/p75 (PSIP1), CPSF6, Nup358 and TNPO3) in situ into the endogenous genes in human HSC confers resistance to HIV infection in the progeny of the infected cells. The methods and compositions of the invention modify the HIV resistance of long term stem cells (LT-HSC): those stem cells that are often scarce (from 0.01 to 0.001% in a bulk CD34+ cell pool, depending on the source of the cells), and primitive yet give rise to the majority of the more mature cells. These LT-HSC are often resistant to genomic manipulation (see Genovese et al, (2014) *Nature* 510(7504):235-40 and U.S. Publication No. 20150174169), however the methods and compositions of the invention demonstrate efficient modification of these cells (see U.S. Publication No. 20160024474).

Cells and methods as described can be transplanted into animal models and/or human patients without significantly impacting HSC function and viability (e.g., as assessed by measuring absolute levels of cell engraftment in transplanted subjects). In addition, the cells maintain their ability to support hematopoiesis, persist in vivo, and can suppress HIV replication in the subject after transplantation.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

A "functional domain" is a domain of a polypeptide comprising a specific activity. Non-limiting examples of activities that a functional domain may possess are nuclease activity, transcriptional regulatory activity, viral capsid recognition activity and the like.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; 6,534,261 and 8,585,526; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; 8,586,526; WO 95/19431; WO 96/06166; WO 98/53057; WO 98/54311; WO 00/27878; WO 01/60970 WO 01/88197, WO 02/099084.

"TtAgo" is a prokaryotic Argonaute protein thought to be involved in gene silencing. TtAgo is derived from the bacteria *Thermus thermophilus*. See, e.g. Swarts et al, ibid, G. Sheng et al., (2013) *Proc. Natl. Acad. Sci. U.S.A.* 111, 652). A "TtAgo system" is all the components required including e.g. guide DNAs for cleavage by a TtAgo enzyme.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein cleave (e.g., create one or more single-stranded nicks and/or one or more double-stranded breaks (DSBs)) in the target sequence (e.g., cellular chromatin) at a predetermined site. The DSB may result in deletions and/or insertions by homology-directed repair or by non-homology-directed repair mechanisms. Deletions may include any number of base pairs. Similarly, insertions may include any number of base pairs including, for example, integration of a "donor" polynucleotide, optionally having homology to the nucleotide sequence in the region of the break. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins, TALENs, TtAgo or CRISPR/Cas systems can be used for additional double-stranded cleavage of additional target sites within the cell.

Any of the methods described herein can be used for insertion of a donor of any size and/or partial or complete inactivation of one or more target sequences in a cell by targeted integration of donor sequence that disrupts expression of the gene(s) of interest. Cell lines with partially or completely inactivated genes are also provided.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

"Genetically modified" refers to a modification made to a nucleic acid such that the sequence of the nucleic acid is altered in comparison to the nucleic acid prior to being modified. Genetically modifying a cell refers to modifying cellular nucleic acid within a cell, including genetic modifications to endogenous and/or exogenous nucleic acids within the cell. Genetic modifications can comprise deletions, insertions, integrations of exogenous DNA, gene correction and/or gene mutation.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528, 20080131962 and 20110201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 100,000,000 nucleotides in length (or any integer value therebetween or thereabove), preferably between about 100 and 100,000 nucleotides in length (or any integer therebetween), more preferably between about 2000 and 20,000 nucleotides in length (or any value therebetween) and even more preferable, between about 5 and 15 kb (or any value therebetween).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster. Methods for the introduction of exogenous molecules into plant cells are known to those of skill in the art and include, but are not limited to, protoplast transformation, silicon carbide (e.g., WHISKERS™), Agrobacterium-mediated transformation, lipid-mediated transfer (i.e., liposomes, including neutral and cationic lipids), electroporation, direct injection, cell fusion, particle bombardment (e.g., using a "gene gun"), calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP, TALE, TtAgo or CRISPR/Cas system as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells), including stem cells (pluripotent and multipotent).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP, TALE, TtAgo or Cas DNA-binding domain is fused to an activation domain, the ZFP, TALE, TtAgo or Cas DNA-binding domain and the activation domain are in operative linkage if, in the fusion polypeptide, the ZFP, TALE, TtAgo or Cas DNA-binding domain portion is able to bind its target site and/or its binding site, while the activation domain is able to upregulate gene expression. When a fusion polypeptide in which a ZFP, TALE, TtAgo or Cas DNA-binding domain is fused to a cleavage domain, the ZFP, TALE, TtAgo or Cas DNA-binding domain and the cleavage domain are in operative linkage if, in the fusion polypeptide, the ZFP, TALE, TtAgo or Cas DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the nucleases, donors and/or genetically modified cells of the invention can be administered. Subjects of the present invention include those with a disorder.

"Stemness" refers to the relative ability of any cell to act in a stem cell-like manner, i.e., the degree of toti-, pluri-, or oligopotentcy and expanded or indefinite self-renewal that any particular stem cell may have.

By "cells that do not sustain HIV infection" is meant a cell that exhibits increased resistance to HIV infection (as compared to cells without the modification) and/or cells that exhibit decreased replication of HIV.

The term "secondary" or "serial" transplantation is used in a convention sense to refer to administration of cells obtained from a subject that was previously administered cells, for instance, a subject that has undergone ex vivo administration of stem cells as described herein. Genetically modified stem cells (e.g., LT-HSCs) as described herein can be administered to a subject (e.g., ex vivo) and cells descended from these cells (including differentiated cells) within the subject also exhibit the genetic modification(s). Furthermore, stem cells isolated from this subject (e.g., bone marrow) also retain the desired genetic modifications, indicating that they are LT-HSCs which can be used for subsequent (serial or secondary) transplantations for the provision of the genetically modified cells to one or more different subjects.

Fusion Molecules

Described herein are compositions, for example nucleases, that are useful for cleavage of a selected target gene in a cell. In certain embodiments, one or more components of the fusion molecules (e.g., nucleases) are naturally occurring. In other embodiments, one or more of the components of the fusion molecules (e.g., nucleases) are non-naturally occurring, i.e., engineered in the DNA-binding domain(s) and/or cleavage domain(s). For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains).

A. DNA-Binding Domains

In certain embodiments, the composition and methods described herein employ a meganuclease (homing endonuclease) DNA-binding domain for binding to the donor molecule and/or binding to the region of interest in the genome of the cell. Naturally-occurring meganucleases recognize 15-40 base-pair cleavage sites and are commonly grouped into four families: the LAGLIDADG family ("LAGLIDADG" disclosed as SEQ ID NO: 27), the GIY-YIG family, the His-Cyst box family and the ANTI family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See, also, U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain of one or more of the nucleases used in the methods and compositions described herein comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like (TAL) effectors which mimic plant transcriptional activators and manipulate the plant transcriptome (see Kay et al (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et at (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et at (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Pat. No. 8,586,526, incorporated by reference in its entirety herein.

Specificity of these TAL effectors depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues (RVD) at positions 12 and 13 with the identity of the contiguous nucleotides in the TAL-effector's target sequence (see Moscou and Bogdanove, (2009) *Science* 326:1501 and Boch et at (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN). See, e.g., U.S. Pat. No. 8,586,526; Christian et at ((2010)<*Genetics* epub 10.1534/genetics. 110.120717). In certain embodiments, TALE domain comprises an N-cap and/or C-cap as described in U.S. Pat. No. 8,586,526.

In certain embodiments, the DNA binding domain of one or more of the nucleases used for in vivo cleavage and/or targeted cleavage of the genome of a cell comprises a zinc finger protein. Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In some aspects, the DNA-binding domain targets a CCR5 or AAVS1 gene.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In certain embodiments, the DNA-binding domain is part of a CRISPR/Cas nuclease system. See. e.g., U.S. Pat. No. 8,697,359 and U.S. Patent Publication No. 20150056705. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs functional domain (e.g., nuclease such as Cas) to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof such as derivative Cas proteins. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein. In some embodiments, the Cas protein is a small Cas9 ortholog for delivery via an AAV vector (Ran et at (2015) *Nature* 510, p. 186).

In some embodiments, the DNA binding domain is part of a TtAgo system (see Swarts et al, ibid; Sheng et al, ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan et al., (2005) *Mol. Cell* 19, 405; Olovnikov, et al. (2013) *Mol. Cell* 51, 594; Swarts et al., ibid). Exemplary prokaryotic Ago proteins include those from *Aquifex aeolicus, Rhodobacter sphaeroides*, and *Thermus thermophilus*.

One of the most well-characterized prokaryotic Ago protein is the one from *T. thermophilus* (TtAgo; Swarts et al. ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., ibid). Ago from *Rhodobacter sphaeroides* (RsAgo) has similar properties (Olivnikov et al. ibid).

Exogenous guide DNAs of arbitrary DNA sequence can be loaded onto the TtAgo protein (Swarts et al. ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37° C. Ago-RNA-mediated DNA cleavage could be used to affect a panopoly of outcomes including gene knock-out, targeted gene addition, gene correction, targeted gene deletion using techniques standard in the art for exploitation of DNA breaks.

Thus, the nuclease comprises a DNA-binding domain in that specifically binds to a target site in any gene into which it is desired to insert a donor (transgene).

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity, including for use in genome modification in a variety of organisms. See, for example, U.S. Patent Publications 20030232410; 20050208489; 20050026157; 20050064474; 20060188987; 20060063231; and International Publication WO 07/014275. Likewise, TALE DNA-binding domains have been fused to nuclease domains to create TALENs. See, e.g., U.S. Pat. No. 8,586,526.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. Additional enzymes which cleave DNA are known (e.g., S1 Nuclease; mung bean nuclease; pancreatic DNase I; micrococcal nuclease; yeast HO endonuclease. One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987; 20090305346 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

Cleavage domains with more than one mutation may be used, for example mutations at positions 490 (E→K) and 538 (I→K) in one cleavage half-domain to produce an engineered cleavage half-domain designated "E490K: I538K" and by mutating positions 486 (Q→E) and 499 (I→L) in another cleavage half-domain to produce an engineered cleavage half-domain designated "Q486E:I499L;" mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively); engineered cleavage half-domain comprising mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively); and/or engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). See, e.g., U.S. Pat. Nos. 7,914,796; 8,034,598 and 8,623,618, the disclosures of which are incorporated by reference in its entirety for all purposes. In other embodiments, the engineered cleavage half domain comprises the "Sharkey" and/or "Sharkey'" mutations (see Guo et al, (2010) *J. Mol. Biol.* 400(1):96-107).

Alternatively, nucleases may be assembled in vivo at the nucleic acid target site using so-called "split-enzyme" technology (see, e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in U.S. Pat. No. 8,563,314.

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al, (2013) *Sciencexpress* 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek ibid and Cong, ibid).

Target Sites

As described in detail above, DNA-binding domains can be engineered to bind to any sequence of choice. An engineered DNA-binding domain can have a novel binding specificity, compared to a naturally-occurring DNA-binding domain.

In certain embodiments, the nuclease targets a "safe harbor" loci such as the AAVS1, HPRT, ALB and CCR5 genes in human cells, and Rosa26 in murine cells (see, e.g., U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20060063231; 20080159996; 201000218264; 20120017290; 20110265198; 20130137104; 20130122591; 20130177983 and 20130177960) and the Zp15 locus in plants (see U.S. Pat. No. 8,329,986).

Part of HIV's success as a human pathogen is due to the fact that it circumvents the action of cellular restriction factors such as TRIM5α, APOBEC3G and BST-2. "Restriction factors", as used herein to refer to anti-HIV effectors including exemplary effectors that are part of the cell-autonomous innate immune system, whereby cells detect the presence of pathogens and respond by deploying both local and systemic defense measures (reviewed in Towers and Noursadeghi (2014), *Cell Host Microbe.* 16(1):10-18). During viral infections, these anti-viral effectors tend to be induced by interferon and contribute to the so-called 'anti-viral state' in neighboring cells. The prototype human restriction factors that act against HIV-1 are TRIM5α, APOBEC3G (A3G) and BST-2/tetherin, SAMHD1 and Mx2. (Towers and Noursadeghi, ibid). These intracellular proteins directly inhibit various stages of the viral life-cycle and, in the examples of TRIM5α and BST-2, they also play a role in sensing HIV and signaling, so that the consequences of expression of these factors is expected to go beyond just protecting an individual cell.

Restriction factor genes are under intense evolutionary pressure, exhibiting high rates of non-synonymous mutations, species adaptations and target virus specificity. However, today's successful human pathogens such as HIV-1 have, by definition, evolved ways to circumvent the current slate of human factors. Despite this fact, HIV-1 remains sensitive to the orthologous genes present in many non-human primates. This discrepancy has allowed the identification of point mutations or domain swaps that can be introduced into the human proteins to create forms that now inhibit HIV-1.

Thus, in certain embodiments, described herein are cells and methods for introducing mutations in situ into the endogenous genes for these factors in human HSC, thereby conferring HIV-resistance and/or sensing capabilities to the progeny of the edited cells, effectively 'speeding up evolution' to provide a gain-of-function to the human factors and thereby create HIV-resistant cells. In other embodiments, the target site for mutation (e.g., point mutation) in a gene that results in anti-HIV activity, for example, a component of the cell-autonomous innate immune system, including, by way of non-limiting example, a target site in one or more of the following genes: the restriction factors TRIM5α, APOBEC3G and/or BST-2. These intracellular proteins directly inhibit various stages of the viral life-cycle and, in the case of TRIM5α and BST-2, also trigger additional anti-viral responses. In contrast, HIV-1 is generally susceptible to orthologs of these proteins in non-human primates, allowing specific mutations to be mapped that can restore anti-HIV activity to the human factors. Accordingly, such mutations in situ in the endogenous genes for these factors in human HSCs confers HIV-resistance and/or sensing capabilities to the progeny of the edited cells.

In certain embodiments, the target site(s) is(are) in an intron of an endogenous gene. Non-limiting examples of suitable genomic intronic regions for targeting include, intron 6 or 7 of TRIM5α; intron 2 or 3 of APOBEC3G; and intron 1 of tetherin.

Donors

In certain embodiments, the present disclosure relates to nuclease-mediated targeted integration of an exogenous sequence into the genome of a cell. As noted above, insertion of an exogenous sequence (also called a "donor sequence" or "donor" or "transgene"), for example for deletion of a specified region and/or correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest or can be integrated via non-homology directed repair mechanisms. Additionally, donor sequences can comprise a vector molecule containing sequences that are not homologous to the region of interest in cellular chromatin. A donor molecule can contain several, discontinuous regions of homology to cellular DNA. Further, for targeted insertion of sequences not normally present in a region of interest, said sequences can be present in a donor nucleic acid molecule and flanked by regions of homology to sequence in the region of interest.

As with nucleases, the donors can be introduced into any form. In certain embodiments, the donors may be introduced using DNA and/or viral vectors by methods known in the art. See, e.g., U.S. Patent Publication Nos. 20100047805 and 20110207221. The donor may be introduced into the cell in double- or single-stranded form. The donor may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

In certain embodiments, the donor includes sequences (e.g., coding sequences, also referred to as transgenes) greater than 1 kb in length, for example between 2 and 200 kb, between 2 and 10 kb (or any value therebetween). The donor may also include at least one nuclease target site. In certain embodiments, the donor includes at least 2 target sites, for example for a pair of ZFNs, TALENs, TtAgo or CRISPR/Cas nucleases. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor can be inserted so that its expression is driven by the endogenous promoter at the integration site, namely the promoter that drives expression of the endogenous gene into which the donor is inserted. However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. In some embodiments, the transgene is integrated into a safe harbor gene, for example CCR5 such that CCR5 is inactivated. See, e.g., U.S. Pat. Nos. 7,951,925 and 8,524,221. In other embodiments, the donor is integrated into a TRIM5α gene such that the polypeptide encoded by the donor is expressed as a fusion protein with endogenous TRIM5α (e.g., a Cyp-encoding sequence is integrated into an endogenous TRIM5α gene such that a TRIM5α-Cyp fusion protein is expressed).

Furthermore, although not required for expression, exogenous sequences may also include transcriptional or translational regulatory or other sequences, for example, promoters, enhancers, insulators, internal ribosome entry sites, sequences encoding 2A peptides and/or polyadenylation signals. Additionally, splice acceptor sequences may be included. Exemplary splice acceptor site sequences are known to those of skill in the art and include, by way of example only, CTGACCTCTTCTCTTCCTCCCACAG, (SEQ ID NO: 10)(from the human HBB gene) and TTTCTCTCCACAG (SEQ ID NO: 11) (from the human Immunoglobulin-gamma gene)

The donor sequences (transgenes and/or repair templates) described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The donor polynucleotides described herein may include one or more non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In some embodiments, the donor further comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above. The coding sequences may be, for example, cDNAs.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

In certain embodiments, the donor may include, for example, wild-type genes to replace mutated endogenous sequences. For example, a wild-type (or other functional) gene sequence may be inserted into the genome of a stem cell in which the endogenous copy of the gene is mutated. In other embodiments, the donor may include, for example, a mutant gene to replace wild-type endogenous genes. For example, a mutant (or other alternative) gene sequence may be inserted into the genome of a stem cell to mutate the endogenous gene involved in HIV infection. The transgene may be inserted at the endogenous locus, or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences may also transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes).

Targeted insertion of non-coding nucleic acid sequence may also be achieved. Sequences encoding antisense RNAs, RNAi, shRNAs and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Cells

Thus, provided herein are genetically modified cells comprising an anti-HIV transgene, for example a transgene that expresses a functional anti-HIV transgene including by way of example only: (i) the entry inhibitor peptide C46, expressed as both cell surface anchored and secreted molecules, (ii) a humanized TRIM-Cyp fusion protein, which serves as potent intracellular restriction factors, and/or (iii) a dual-specificity soluble CD4/CCR5-mimetic peptide (eCD4-IgG) that inhibits a broad spectrum of HIV isolates. Also provided are genetically modified cells in which a factor involved in HIV infectivity and/or propagation is modified, including by way of example only: (i) TRIM5α, (ii) APOBEC3G and/or (iii) BST-2. In certain embodiments, the genetically modified cell comprises a cyclophilin A (CypA)-encoding transgene integrated in place of the HIV recognition domain in exon 8 of TRIM5α.

The donor is typically integrated in a targeted manner into the cell's genome using one or more nucleases. In certain embodiments, the donor is integrated into CCR5, for example for inactivation of the CCR5 receptor gene. In other embodiments, the donor is integrated into an endogenous gene associated with HIV, for instance a restriction factor such as TRIM5α, APOBEC3G and/or BST-2 (tetherin). In any of the cells described herein, integration may be into an exon and/or an intron (e.g., intron 6 or 7 of TRIM5α, intron 2 or 3 of APOBEC3G, or intron 1 of tetherin).

Unlike random integration, targeted integration ensures that the transgene is integrated into a specified gene. The donor may be integrated anywhere in the target gene. In certain embodiments, the donor is integrated at or near the nuclease cleavage site, for example, within 1-3000 (or any value therebetween) base pairs upstream or downstream of the site of cleavage, more preferably within 1-1000 base pairs (or any value therebetween) of either side of the cleavage site, or within 1 to 500 base pairs (or any value therebetween), or within 1 to 100 base pairs (or any value therebetween) of either side of the cleavage site. In certain embodiments, the integrated sequence comprising the donor transgene does not include any vector sequences (e.g., viral vector sequences).

Any cell type can be genetically modified as described herein to comprise a donor sequence, including but not limited to cells and cell lines. Other non-limiting examples of cells as described herein include T-cells (e.g., CD4+, CD3+, CD8+, etc.); T memory stem cells, dendritic cells; B-cells; autologous (e.g., patient-derived) or heterologous (allogenic) pluripotent, totipotent or multipotent stem cells (e.g., CD34+ cells, induced pluripotent stem cells (iPSCs), embryonic stem cells or the like). In certain embodiments, the cells as described herein are HSCs.

The cells as described herein are useful in treating and/or preventing HIV in a subject with the disorder, for example, by ex vivo therapies. The nuclease-modified cells can be expanded and then reintroduced into the patient using standard techniques. See, e.g., Tebas et at (2014) *New Eng J Med* 370(10):901. In the case of stem cells, after infusion into the subject, in vivo differentiation of these precursors into cells expressing the functional protein also occurs. Pharmaceutical compositions comprising the cells as described herein are also provided. In addition, the cells may be cryopreserved prior to administration to a patient.

The cells and ex vivo methods as described herein provide treatment and/or prevention of HIV in a subject and eliminate the need for continuous prophylactic pharmaceutical administration or risky therapies. As such, the invention described herein provides a safer, cost-effective and time efficient way of treating and/or preventing HIV.

Delivery

The nucleases, polynucleotides encoding these nucleases, donor polynucleotides and compositions comprising the proteins and/or polynucleotides described herein may be delivered by any suitable means. In certain embodiments, the nucleases and/or donors are delivered in vivo. In other embodiments, the nucleases and/or donors are delivered to isolated cells (e.g., autologous or heterologous stem cells) for the provision of modified cells useful in ex vivo delivery to HIV patients.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using any nucleic acid delivery mechanism, including naked DNA and/or RNA (e.g., mRNA) and vectors containing sequences encoding one or more of the components. Any vector systems may be used including, but not limited to, plasmid vectors, DNA minicircles, retroviral vectors, lentiviral vectors, adenovirus vectors, poxvirus vectors; herpesvirus vectors and adeno-associated virus vectors, etc., and combinations thereof. See, also, U.S. Pat. Nos. 6,534,261; 6,607,882; 6,824,978; 6,933,113; 6,979,539; 7,013,219; and 7,163,824, and U.S. Patent Publication No. 20140335063, incorporated by reference herein in their entireties. Furthermore, it will be apparent that any of these systems may comprise one or more of the sequences needed for treatment. Thus, when one or more nucleases and a donor construct are introduced into the cell, the nucleases and/or donor polynucleotide may be carried on the same delivery system or on different delivery mechanisms. When multiple systems are used, each delivery mechanism may comprise a sequence encoding one or multiple nucleases and/or donor constructs (e.g., mRNA encoding one or more nucleases and/or mRNA or AAV carrying one or more donor constructs).

Conventional viral and non-viral based gene transfer methods can be used to introduce nucleic acids encoding nucleases and donor constructs in cells (e.g., mammalian cells) and target tissues. Non-viral vector delivery systems include DNA plasmids, DNA minicircles, naked nucleic acid, and nucleic acid complexed with a delivery vehicle such as a liposome, lipid nanoparticle (LNP), poly-lactate-glycolic acid nanoparticles, poly-amine complexing agents, or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, naked RNA, capped RNA, artificial virions, and agent-enhanced uptake of DNA. Sonoporation using, e.g., the Sonitron 2000 system (RichMar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. In some aspects, the nucleases are delivered as mRNAs and the transgene is delivered via other modalities such as viral vectors, minicircle DNA, plasmid DNA, single-stranded DNA, linear DNA, liposomes, nanoparticles and the like.

The preparation of lipid:nucleic acid complexes, including targeted liposomes such as immunolipid complexes, is well known to one of skill in the art (see, e.g., Crystal, Science 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et at (2009) *Nature Biotechnology* 27(7):643).

The use of RNA or DNA viral based systems for the delivery of nucleic acids encoding engineered CRISPR/Cas systems take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to subjects (ex vivo). Conventional viral based systems for the delivery of CRISPR/Cas systems include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989). Any AAV serotype can be used, including AAV1, AAV3, AAV4, AAV5, AAV6 and AAV8, AAV 8.2, AAV9, and AAV rh10 and pseudotyped AAV such as AAV2/8, AAV2/5 and AAV2/6.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 base pair (bp) inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV8, AAV9 and AAVrh10, and all variants thereof including engineered mutants selected from libraries, can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual subject, typically by systemic administration (e.g., intravenous, intraperitoneal, intramuscular, subdermal, sublingual or intracranial infusion) topical application, as described below, or via pulmonary inhalation. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application, inhalation and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Viro.* 72:9873-9880; Follenzi et al. (2000) *Nature Genetics* 25:217-222; U.S. Patent Publication No 2009/054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

It will be apparent that the nuclease-encoding sequences and donor constructs can be delivered using the same or different systems. For example, a donor polynucleotide can be carried by an AAV, while the one or more nucleases can be carried by mRNA. Furthermore, the different systems can be administered by the same or different routes (intramuscular injection, tail vein injection, other intravenous injection, intraperitoneal administration and/or intramuscular injection. Multiple vectors can be delivered simultaneously or in any sequential order.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Applications

The methods and compositions disclosed herein are for providing cell-based therapies for HIV. The cell may be modified in vivo or may be modified ex vivo and subsequently administered to a subject. Furthermore, the genetically modified cells described herein have been shown to be suitable for serial (secondary) transplantations in that stem cells can be isolated from the subject and these cells retain the genetic modification and can be administered to one or more additional subjects. Thus, the methods and compositions provide for the treatment and/or prevention of HIV.

Targeted integration of an anti-HIV donor may be used to correct an aberrant gene, insert a wild type gene, create a gain-of-function mutation within an endogenous gene, or change the expression of an endogenous gene. For instance, a wild-type transgene encoding an anti-HIV transgene may be integrated into a cell to provide a cell that produces a functional protein. Targeted knock out of an HIV supportive gene, or modification by the methods described herein may provide a cell that is resistance to HIV infection. Genomic editing may also include correction or introduction of mutations (e.g., point mutations) in an endogenous gene, for example to modify endogenous gene expression. In addition, targeted integration of a mutated anti-HIV transgene may be done to treat or prevent HIV.

By way of non-limiting example, the methods and compositions described herein can be used for treatment and/or prevention of HIV.

The following Examples relate to exemplary embodiments of the present disclosure using ZFNs. It will be appreciated that that any nucleases can be used, for example, other zinc finger nucleases (ZFNs), TALENs, TtAgo, CRISPR/Cas systems, homing endonucleases (meganucleases) with engineered DNA-binding domains and/or fusions of naturally occurring of engineered homing endonucleases (meganucleases) DNA-binding domains and heterologous cleavage domains and/or fusions of meganucleases and TALE proteins.

EXAMPLES

Example 1: Anti-HIV Transgene Activity

To evaluate the anti-HIV activity of the candidate restriction factors, we generated lentiviral vectors expressing both GFP and rationally mutated forms of TRIM5α and A3G. The TRIM5α variant contained the mutation R322P (see, e.g., Li et al. (2006) *J. Virol.* 80(14):6738), which restores the ability of the human factor to recognize the HIV-1 capsid, while the modified A3G carried the mutation D128K (see, e.g., Schrofelbauer et al. (2004) *Proc. Nat'l. Acad. Sci.* 101(11):3927-32), which provides resistance to degradation by the HIV-1 Vif protein. In addition we generated lentiviral vectors expressing a "humanized" form of TRIM-Cyp, which mimics the restriction factors found in certain NW and OW primates, and which recognizes the HIV-1 capsid through a co-opted cyclophilin A domain (see, e.g., Neagu et al. (2009) *J. Clin. Invest.* 119:3035-3047). Also evaluated was the transdominant viral protein RevM10, which has previously been used in human gene therapy trials (Podsakoff et al. (2005) *Mol Ther.* 12(1):77-86).

We transduced each vector into Jurkat cells, selected for the GFP+ population by FACS, and then challenged these cells with HIV-1.

As shown in FIG. 1, all three of the modified restriction factors inhibited HIV-1 replication, and to a greater extent than RevM10, in this initial cell line analysis.

Example 2: Nuclease-Mediated Modification of TRIM5α, A3G and BST-2

Figure 2:
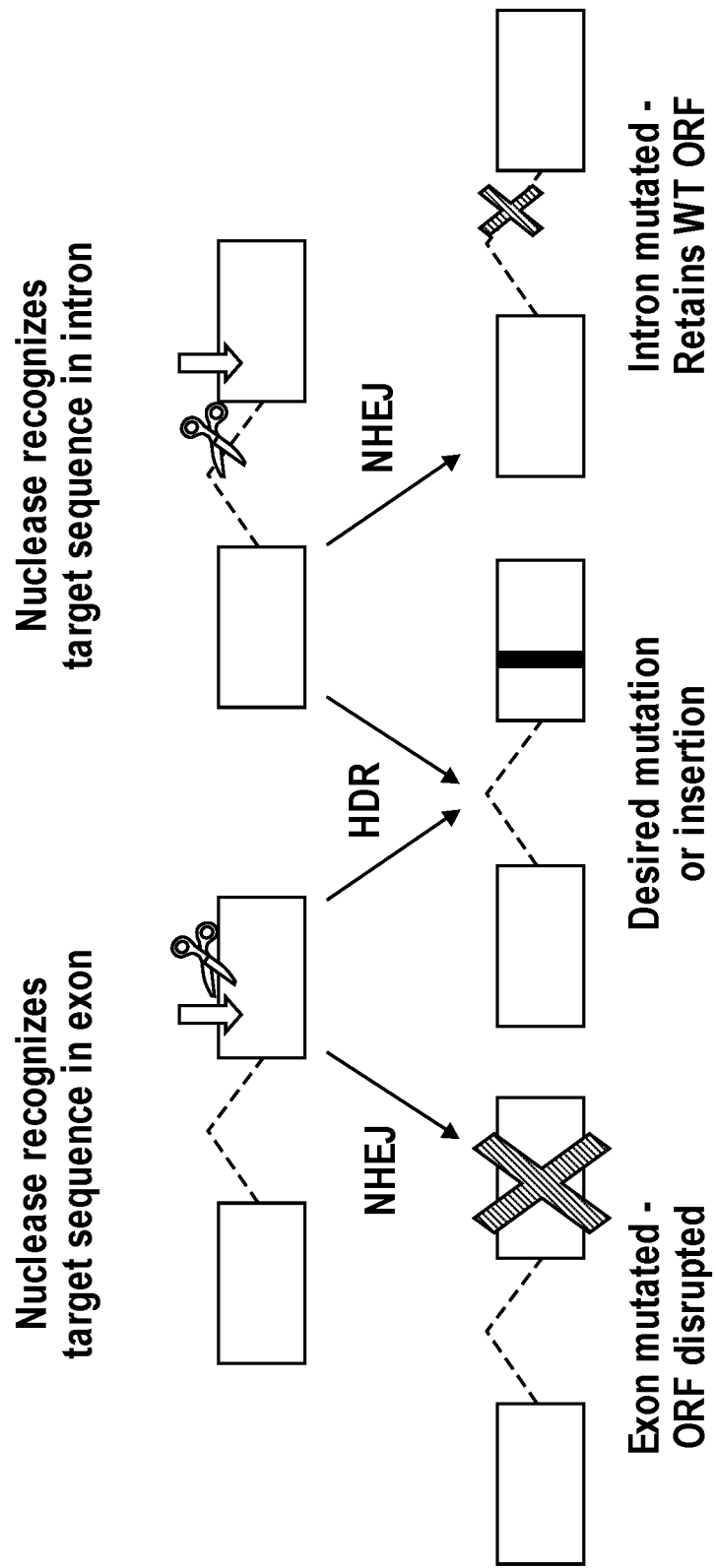
FIG. 2 is a schematic depicting nuclease-mediated genomic modification, including examples where nucleases target sequences in exons or introns. The arrows indicate the desired edit site in the exon, while the scissors indicate the recognition sites for the engineered nucleases, in either an exon (left) or intron (right). Possible outcomes are shown below if a homologous donor sequence is also introduced into the cell to allow homology directed repair (HDR) to edit the gene (desired mutation or insertion). Also shown are the results of NHEJ mediated repair which could create gene disruption if the nuclease(s) is(are) targeted to the exon.

Mutations, such as point mutations are introduced into endogenous human restriction factors to provide a gain-of-function to these factors. Since these genes likely have other pathogen targets and cellular functions, it is desirable to leave their ORFs intact. One way to do this is to only modify one allele in a cell. Another way is to design nucleases to introduce DSBs in introns adjacent to the proposed gene editing sites in order to minimize loss of function subsequent to any NHEJ repair of the DSBs. (FIG. 2). Nucleases are designed to avoid splice donor and acceptor sites and predicted regulatory sequences in the introns. These nucleases support high levels of HDR following the introduction of a donor sequence, and direct no or very low rates of on-target gene-disruption events subsequent to NHEJ repair (e.g., to ensure that no critical intron sequences have been inadvertently disrupted), as evaluated by both genomic sequence analysis and functional expression assays for the endogenous gene.

A. Genomic Editing of TRIM5α

Figure 3:
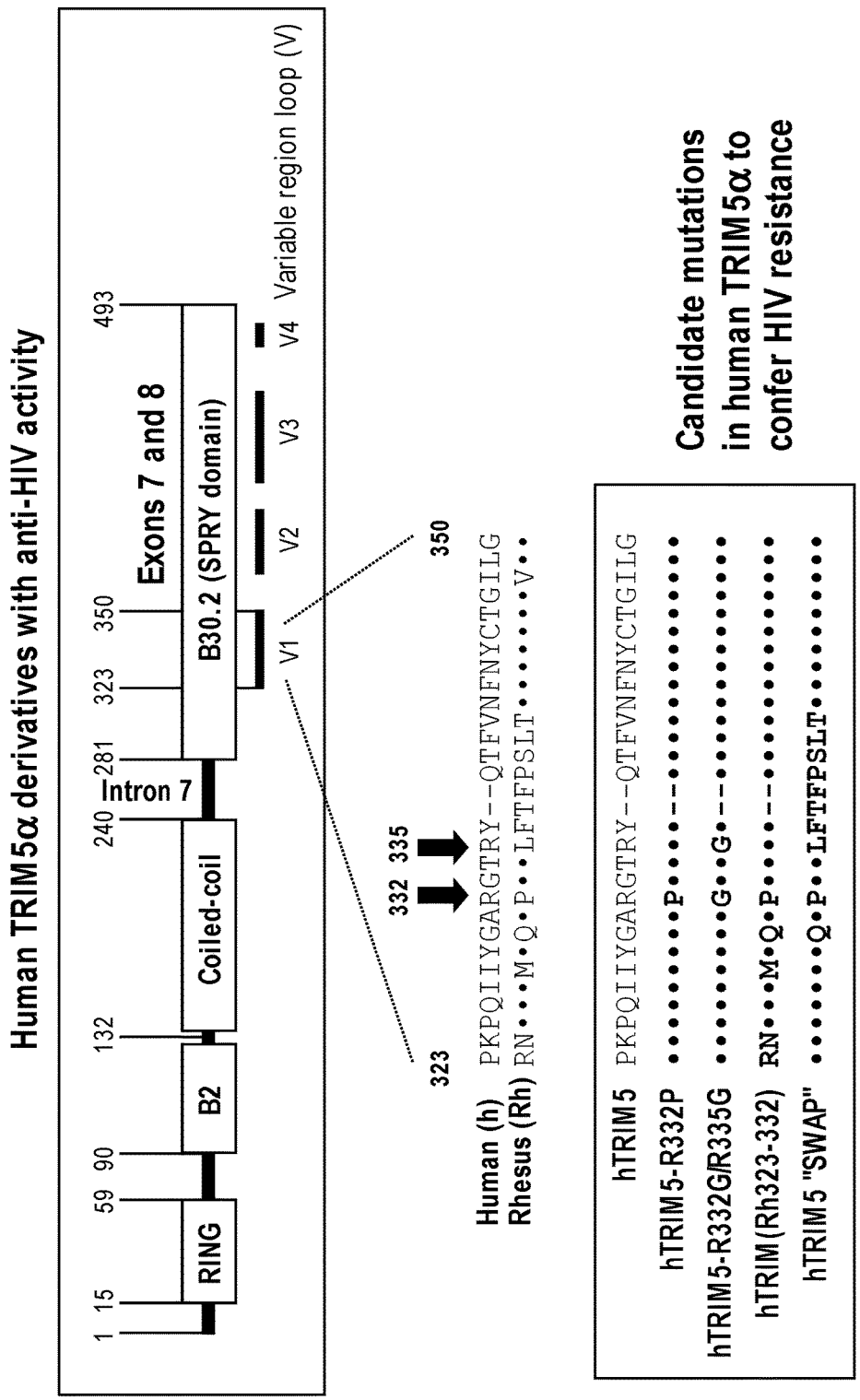
FIG. 3 depicts the organization of human TRIM5α and shows a partial alignment between human (SEQ ID NO: 1) and rhesus macaque (SEQ ID NO: 2) (bolded) protein sequences of TRIM5α proteins, and exemplary human TRIM5α variants with mutations that confer anti-HIV activity (SEQ ID NO:1 and 3-6, respectively, in order of appearance).

TRIm5α is a cytoplasmic body component and a member of the ~100 member TRIM family. The rhesus form of TRIM5α retains activity against HIV-1, and although its mode of restriction is incompletely understood, it seems to inhibit early stages of the life-cycle and is based on recognition of the retroviral capsid by the C-terminal SPRY domain. See, e.g., FIG. 3. Importantly, TRIM5α also acts as a pattern recognition receptor for the HIV capsid, triggering the TAK1/NF-kB pathway and leading to other antiviral responses. The rhesus form of TRIM5α retains activity against HIV-1 and substitutions in the sequences that vary between the human and primate forms have identified changes at for example residues 332 and/or 335 that are capable of transferring this anti-HIV activity to the human protein. See, e.g., Li et al. (2006) *J. Virol.* 80(14):6738 (R332P) and Pham et al. (2010) *Gene Therapy* 17(7):859-71(R332G/R335G): Other mutations are also possible including a complete swap of exon 8.

These mutations of the endogenous human gene are made to confer anti-HIV activity. Importantly, such proteins will be gain-of-function and act as trans-dominants, so that only a single allele needs to be altered. In the most conservative approach, this may even be a preferred outcome, minimizing any unanticipated consequences of the complete loss of the native allele.

Figure 4:
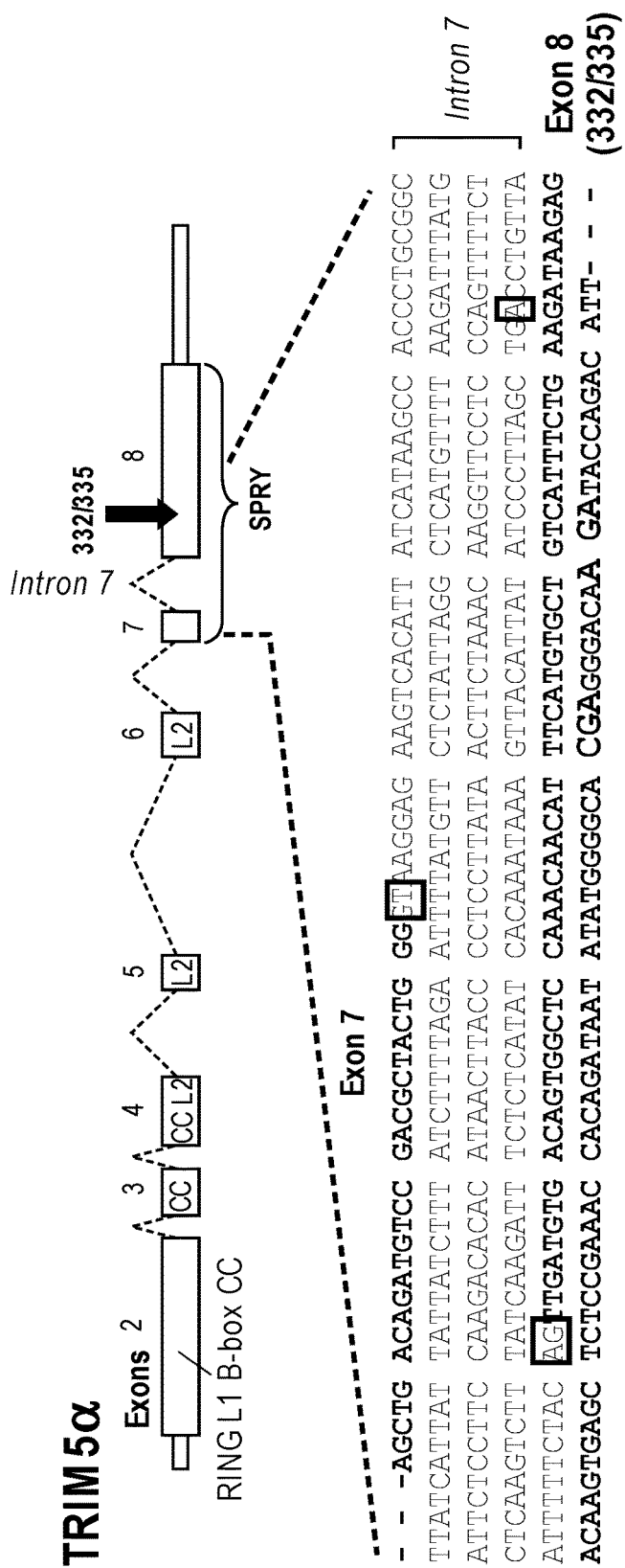
FIG. 4 depicts the genomic organization of human TRIM5α showing the HIV-recognizing SPRY domain in exons 7 and 8 and the approximate site of one example of proposed mutations at residues 332/335 in exon 8. Also shown is the sequence of intron 7 (italicized) and partial sequences of the flanking regions from exons 7 and 8 are shown (bold) (SEQ ID NO:7). The codons for residues 332 and 335 are indicated in larger font. Examples of essential elements to be avoided in intron 7 as nuclease target sites are identified by underlining and boxes, including the splice donor and acceptor sites (boxed), and a putative branch site (boxed) and poly-pyrimidine tracts that may be regulatory elements.

Residues 332 and 335 in the SPRY domain are located in exon 8 of the human gene. Nucleases are generated that target, for example, within upstream intron 7, avoiding the elements that are predicted to be likely consensus splicing sites and regulatory sequences. See, e.g., FIG. 4. Notably, intron 7 has no obvious homology in the human genome. Alternatively, nucleases are generated that target near the SPRY domain in exon 8.

B. Genomic Editing of Human APOBEC3G (A3G)

A3G inhibits HIV-1 replication by hypermutation of the viral genome, through a cytidine deaminase activity that acts on ssDNA, and through other mechanisms that are independent of this activity (See Guo et al (2006) *Journal of Virology* 80 (23): 11710-22). A3G is incorporated into virions by interacting with both the viral RNA genome and NC protein. In response, HIV-1 has evolved the Vif protein to recognize A3G in host cells, and target it for proteosomal degradation. Point mutations of A3G such as D128K, informed by the Vif-resistant African green monkey homologue, confer Vif resistance. See, e.g., Schrofelbauer et al. (2004) *Proc. Nat'l. Acad. Sci.* 101(11):3927-32; Xu et al. (2004) *Proc. Nat'l. Acad. Sci. USA* 101(15):5652-7.

As shown in FIG. 5, residue D128 is located in exon 3 of human A3G. Using a strategy identical to the one described above for TRIM5α, nucleases are designed to target a nearby intron. Both introns 2 and 3 can be targeted. In certain embodiments, the nuclease(s) target(s) downstream intron 3, since the likelihood of impacting essential intronic elements is reduced beyond the immediate vicinity of the GT splice donor. The minimal window between the residue 128 target site and the start of the intron is 80 bp. Database searches support the choice of either intron, which have no homology in the rest of the human genome.

C. Genomic Editing of Human BST-2

BST-2/Tetherin is recognized to have a variety of antiviral functions, including its name-sake activity of preventing the release/tethering virions at the surface of an infected cell. It also regulates IFN production from pDCs, plays roles in facilitating ADCC, and has recently been shown to trigger NFkB-dependent pro-inflammatory responses as a consequence of sensing tethered virions at the cell surface. Like TRIM5α, this role in pathogen recognition may actually prove to be its most important function, and the reason that it is targeted for destruction by all primate lentiviruses. In the case of HIV-1, tetherin is degraded by the Vpu protein. The interactions between these two proteins have been mapped and substitutions at these residues confer Vpu-resistance, including substitutions at residues 41 and 45. See, e.g., Gupta et al. (2009) *PLoS Pathog.* 5(5):e1000443 and Kobayashi et al (2011) *J. Virol* 85(2):932-45

Figure 6:
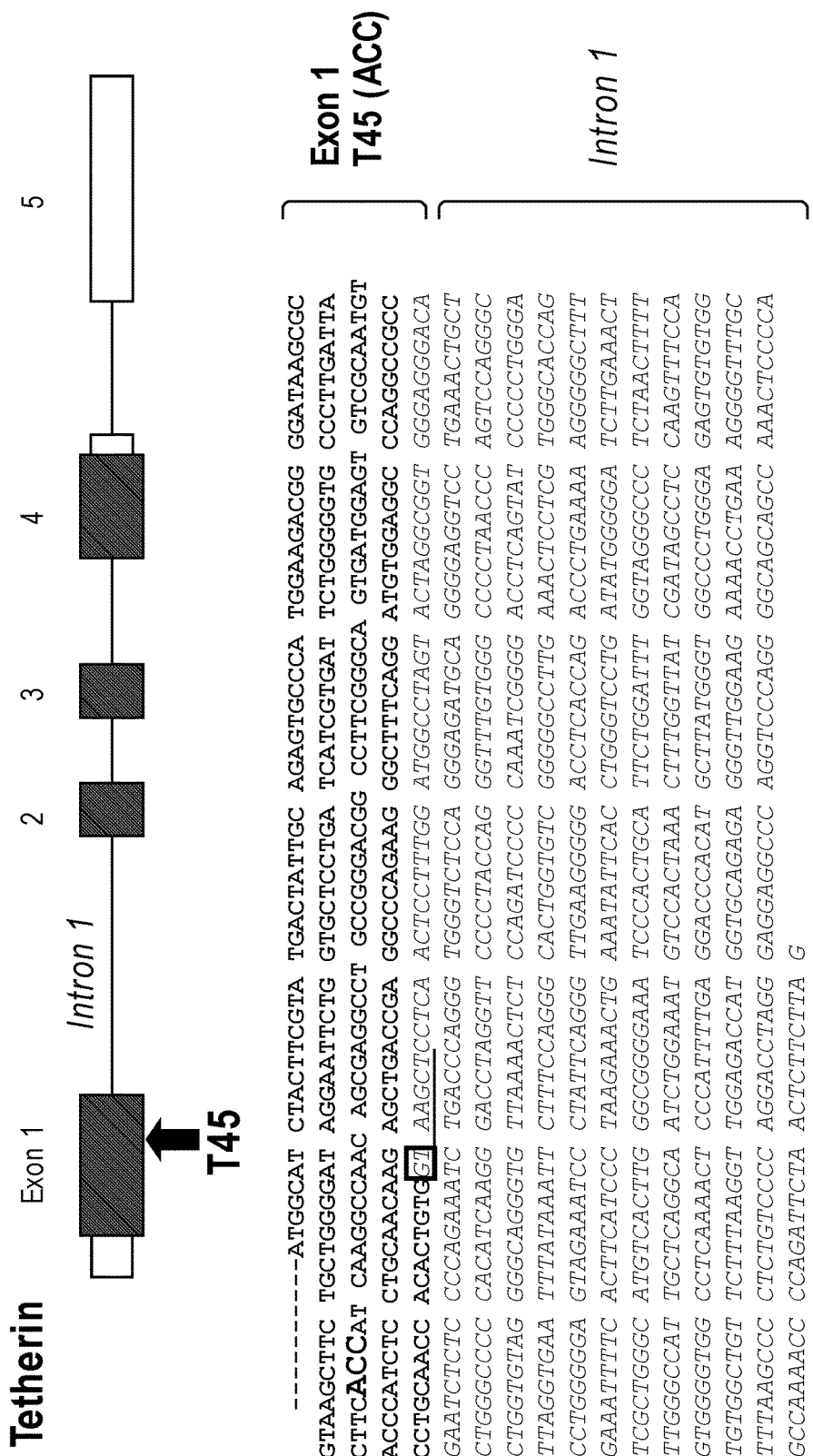
FIG. 6 shows the organization and partial genomic sequence (SEQ ID NO: 9) of BST-2/Tetherin (Tetherin). Intron 1 is shown in italics, part of exon 1 is shown in bold, starting at the ATG start codon, and the location of residue T-45 is in larger font. Nucleases could be targeted upstream of the start codon or to sequences in intron 1. Illustrative examples of nucleotides in intron 1 that may be splicing regulatory sequences and are to be avoided as target sites for nucleases are underlined, and include the splice donor site (boxed).
Figure 7:
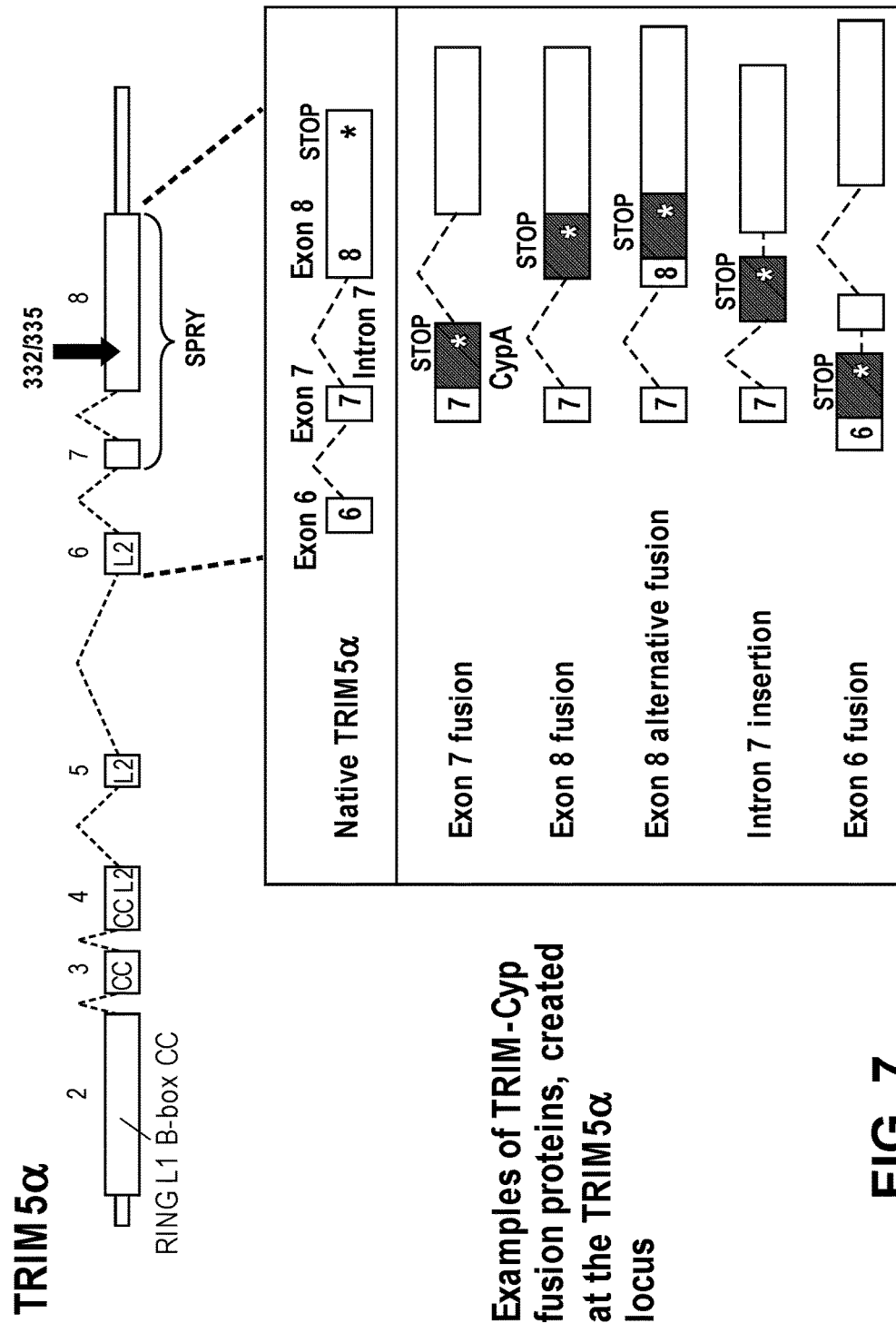
FIG. 7 shows exemplary genomic mutations to the TRIM5α genomic sequence whereby the cyclophilin A (CypA) gene could be inserted to create a TRIM5α-CypA fusion. The coding exons in TRIM5α are shown as grey boxes, introns are dashed lines, the CypA sequence is shown as a black box, with a stop codon indicated by the symbol "*". Non-coding sequences created following the insertion of CypA into TRIM5α are shown as white boxes.

As shown in FIG. 6, these residues are located in exon 1, and the available downstream intron 1 is located about 150 base pairs away. As with A3G, the availability of a downstream intron for nuclease targeting is considered an advantage in terms of the ease of avoiding important intronic elements. However upstream sequence could also be targeted in the 5'UTR (untranslated region). Database searches reveal no homology with the rest of the human genome.

Figure 10B:
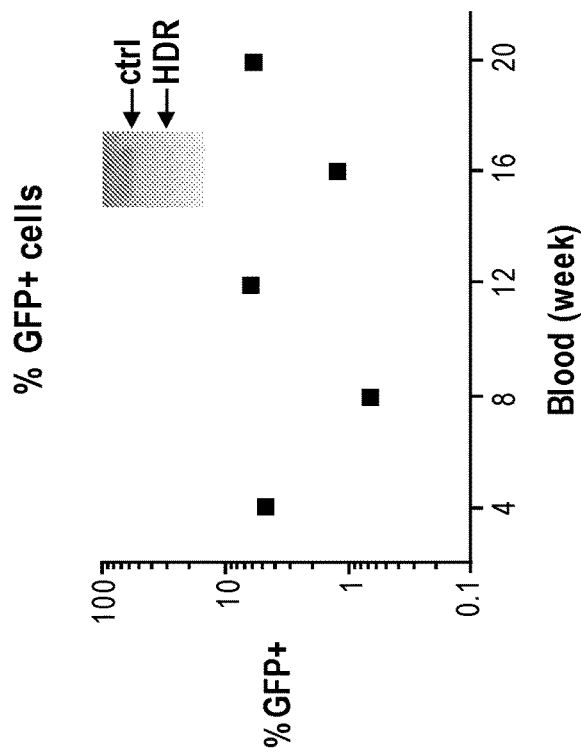
FIGS. 10A and 10B are graphs showing the percentage of human CD45+ cells (FIG. 10A) and the percentage of GFP+ cells (FIG. 10B) in blood of a secondary host mouse following transplantation with cells harvested from bone marrow of mice previously transplanted with human HSCs treated with CCR5 ZFNs and CCR5-GFP AAV6 vectors. The insert shows a gel from a qPCR experiment indicating site-specific insertion of the GFP transgene at the CCR5 locus ('HDR'). Also shown is a control (Ctrl) qPCR.
Figure 10A:
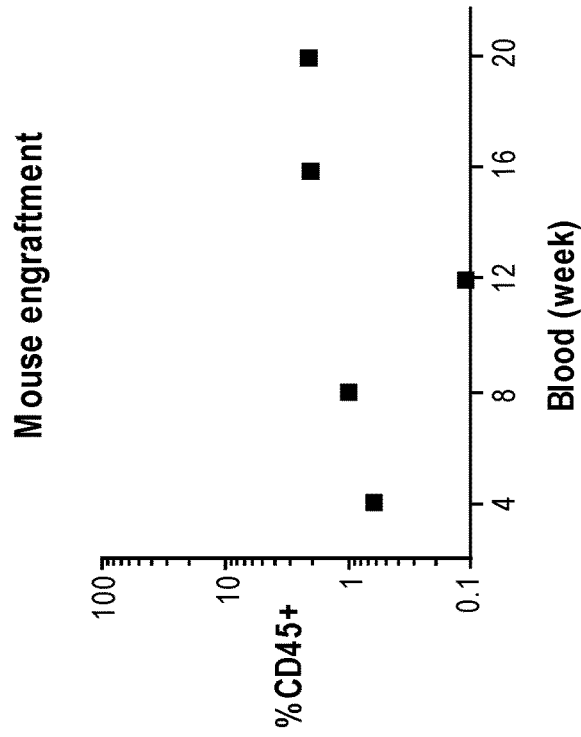

D. Genomic Editing of Human TRIM by Site-Specific Addition of the Human Cyclophilin A (CypA) cDNA into the humanTRIM5α Locus It is possible to mimic events that have occurred at least twice in primate evolution, where retrotransposition of the CypA gene into the TRIM5 locus has led to the replacement of the SPRY domain with the capsid recognizing capability of CypA. Indeed, since CypA is also a positive factor for lentiviral replication, influencing early events such as capsid uncoating and transport to the nuclease, such a strategy is particularly difficult for a lentivirus to evolve resistance against it.

Accordingly, HDR-mediated site-specific addition of the CypA cDNA is employed. The anti-HIV activity of human TRIM-Cyp has already been validated in the construct we tested as described in Example 1. See, also, Neagu et al. (2009) *J. Clin. Invest.* 119:3035-3047).

As shown in FIG. 7, several alternate donor sequence designs are used to create the desired fusion protein(s). These include a direct fusion of CypA to exon 7, or the insertion of the CypA cDNA into exon 8, to thereby retain the authentic intron 7 splicing information. In addition, a cassette that links CypA with a new upstream splice acceptor and 5' regulatory sequences is also generated and designed to be inserted within intron 7. In other designs, CypA is inserted downstream of exon 6 to replace both exon 7 and 8. Some examples of functional junctions of chimeric TRIM-Cyp proteins that could be generated by appropriate donor sequence design are described in Neagu et al. (2009) *J. Clin. Invest.* 119:3035-3047).

In other designs, a minimal HIV capsid-recognizing domain of CypA or other HIV recognizing protein is used as the fusion partner.

Example 3: AAV6 Donor Promotes High Levels of Site-Specific Gene Addition in Human HSC that are Maintained Following Transplantation into Humanized Mice We have found that AAV6 vectors comprising transgene donors are highly tropic for CD34+ HSC (FIG. 11) (see U.S. Patent Publication No. 20150110762 and 62/033,424). Thus, AAV6 vectors comprising a PGK-GFP transgene cassette were designed for integration into either the CCR5 or AAVS1 safe harbor loci into HSC ex vivo. The mechanism whereby homologous sequences on the AAV genome are used in HDR and thereby lead to the site-specific insertion of transgenes or editing of endogenous genes is depicted in FIG. 12A. HSC were incubated with the AAV6 transgene containing vectors where the transgenes were flanked by homology regions with homology to either the region surrounding the CCR5 target (FIG. 12B, 13A) or the region surrounding the AAVS1 target (FIG. 13A) or had no flanking homologous regions and only contained the GFP transgene (FIG. 13A). After 24 hours, the cells were electroporated with either a mock solution (no ZFN) or in vitro transcribed mRNAs encoding the corresponding CCR5-specific or AAVS1-specific ZFNs. For the CCR5-specific AAV6 donor, a control electroporation was also done where the mismatched ZFN (specific for AAVS1) was done. Ten days later all samples were assayed for stable GFP expression as measured by FACS analysis.

As shown in FIGS. 8A, 12E, 12F, 13B and 13D, the results of the GFP FACS analysis confirmed the specificity of HDR-mediated transgene targeted integration.

The day 10 HSC cultures were also subject to a semi-quantitative specific PCR assay that detects HDR-mediated site-specific integration to confirm the FACs analysis. As shown in FIGS. 8B, 12G, 12H and 13C, the analysis demonstrated the presence of a band corresponding to the expected size following targeted integration via HDR in the samples comprising the matched ZFN/donor combinations. In addition, similar experiments were performed using CCR5 specific ZFNs and a CCR5-RFLP AAV6 donor (FIG. 12B) which contains an XhoI restriction site with flanking CCR5 homology sequences and whose insertion by HDR can be detected by an RFLP analysis. Site-specific insertion of the Xho1 site at the CCR5 locus was confirmed by deep sequencing (FIG. 12C) and RFLP analysis (FIG. 12D).

Bulk CD34+ HSC cultures were sorted into different groups depending on the expression of CD133 and CD90 to identify the subpopulations of the HSC (FIG. 15A). The groups were labeled as 'committed' or 'multipotent progenitors, MPP' (CD133-CD90-), 'early' or 'short-term (ST) HSC' (CD133+CD90-,'CD90 low') and 'primitive' or 'long-term (LT) HSC' (CD133+CD90+, 'CD90 high') depending on their CD133 and CD90 expression status.

As shown in FIGS. 8C, 15B, 15C, 15E, and 15F, GFP expression was analyzed and found in all samples, and demonstrated that even the most primitive LT-HSC cells were modified by this approach. Similarly, qPCR was used to show that site-specific integration of the GFP transgene had occurred at the CCR5 locus (FIG. 15D) and the AAVS1 locus (FIG. 15G) in all subsets including the LT-HSC.

HSC were treated with CCR5-specific ZFN encoding mRNAs and the AAV6 virus comprising the GFP transgene flanked by CCR5 homology arms. MiSeq analysis was done (Illumina) of the Day 10 cultures and provided the rates of gene modification in the population, including the percent of CCR5 gene disruption due to NHEJ related events, and the percent of GFP targeted integration (see FIG. 8D). These numbers were compared to the percent GFP positive cells obtained by FACS analysis, and showed that the FACS data underestimated the amount of HDR modification due to variations in the amount of GFP expression and because if the two CCR5 alleles in a cell are modified, the cell will only be scored as a single event in the FACS.

The same population of HSC was engrafted into 4 neonatal NSG mice to create humanized mice. 16 weeks later, levels of GFP expression were analyzed in the blood (see FIG. 8E), bone marrow and spleen (FIG. 8F) and expression was calculated either by FACS or PCR. Control mice receiving only AAV6 donors or mismatched combinations of AAV6 donors and ZFN resulted in background levels in these assays.

FIG. 9 shows further results of HSC engraftment into humanized mice, including the percentage of human CD45+ cells in blood and bone marrow following engraftment of ZFN and AAV6-treated or untreated HSCs (FIG. 9A), the percentage of GFP+ cells in blood and bone marrow following engraftment of ZFN-treated HSCs (FIG. 9B). Similarly, FIG. 16A shows the percentage of human CD45+ cells in blood and bone marrow and spleen of mice following engraftment of HSCs treated with ZFNs and AAV6 donors containing either a GFP or XhoI (RFLP) cassette, or untreated (Mock). FIG. 16B depicts an analysis of the same blood and tissue samples as in FIG. 16A, to determine either the percentage of GFP+ cells for mice receiving HSC treated with ZFNs plus CCR5-GFP donor, or the percentage of modified alleles determined by deep sequencing for mice receiving HSC treated with CCR5 specific ZFNs plus CCR5-RFLP donor, In addition, secondary host transplantation was also evaluated by harvesting bone marrow from the mice receiving ZFN-treated HSC as described above (primary hosts) and administering that bone marrow from the primary hosts to secondary hosts. See, e.g., Ceredig (2012) *Stem Cell Res Ther.* 3(1):1-2. As shown in FIG. 10 and FIG. 16 D ZFN-modified HSC support secondary transplantation and the progeny of the transplanted cells maintain the RFLP or GFP addition at the CCR5 locus.

Example 4: Evaluation of Edited and Expanded CD34+ HSC in Non-Human Primate Models of HIV A non-human primate (NHP) model is used to evaluate the anti-viral activity of the edited HSC. A pigtail macaque (*Macaque nemestrina*, Mn) model is used with chimeric simian immunodeficiency viruses that contain an HIV envelope to model HIV infection in humans. For example, studies have shown that the CCR5-tropic env-SHIR-157ipd3N4 virus is ideally suited for pathogenic replication in pigtail macaque (see Ho et al (2009) *Retrovirology* 6:65).

Small molecules and other methodologies that expand HSCs while preserving multipotency have the potential to increase the cell dose available for transplantation, thus improving the clinical outcome in patients transplanted with gene-modified autologous or allogenic HSCs, especially when cell dose is a limiting factor. Thus, the small molecules UM171 and UM729 (Pabst et al (2014) *Nat Meth* 11: 436-442 and) are analyzed for engraftment efficiency of cord blood, steady state and bone marrow mobilized Mn CD34+ cells.

First the cells are evaluated for engraftment in NSG mice following treatment with cytokine+/−SR1, UM729 or UM171. Cells are transplanted into NSG mice after 12 days of culture and show a higher level of engraftment as compared to untreated cells (see Fares et at (2013) 55$^{th}$ ASH Abstract)

To evaluate engraftment potential in the macaque model, Mn mobilized CD34+ cells are transduced/expanded with the combination of SR1/UM171 and a GFP-containing lentivirus or AAV. The original CD34+ Mn donor is pre-conditioned with myeloablative irradiation (1020cGy) and then is infused with the UM171/SR1-GFP treated cell tractions (see Ho et al, ibid). In vivo gene analysis reveals GFP+ granulocytes and lymphocytes. These results demonstrate that UM171 enhances HSC expansion and availability for engraftment.

The use of the vascular niche expansion platform (E4ECs, see Butler et at (2012) *Blood* 120:1344-1347) is also evaluated. Marrow is harvested from Mn and transduced with lentivirus or AAV vector overnight expressing GFP. Donor animals receive total body irradiation (1020cGy) and are infused with the expanded CD34+ cells and gene marking is observed. Engraftment of GFP+ cells is multi-lineage with GFP+ granulocytes and GFP+ lymphocytes detected in the peripheral blood.

Example 5: Evaluation of Anti-HIV Edited HSC in NHP

AAV vectors comprising a PGK-GFP or anti-HIV transgene cassettes are designed for integration into either the CCR5 or AAVS1 safe harbor loci into NHP CD34+ cells ex vivo as described above in Example 3. CD34+ cells are incubated with the AAV or lentiviral transgene containing donor vectors where the transgenes are flanked by homology regions with homology to either the region surrounding the CCR5 target or the region surrounding the AAVS1 target. 24 hours later, the cells are electroporated with either a mock solution (no ZFN) or in vitro transcribed mRNAs encoding the corresponding CCR5-specific or AAVS1 specific ZFN. Edited cells are engrafted into Mn and then levels of GFP or anti-HIV transgene expression are analyzed in the blood, bone marrow and spleen, and expression is calculated either by FACS or PCR. The results show good transgene expression in ZFN-and-donor transduced CD34+ engrafted monkeys, while control monkeys, receiving only donors or mismatched combinations of donors and ZFN, result in background levels in these assays.

Example 6: Materials and Methods

Isolation of human CD34+ HSC.

Leukopaks containing G-CSF mobilized peripheral blood CD34+ HSPC were purchased (Apheresis Care Group, Inc. San Francisco, Calif.) and CD34+ HSC purified by magnetic bead selection using a CliniMACS cell selection device (Miltenyi Biotec, Auburn, Calif.). The enriched CD34+ HSPC were resuspended in media (X-Vivo 10; Lonza, Basel, Switzerland) supplemented with 2 mM L-glutamine, 1% penicillin/streptomycin/amphotericin B (PSA) (Sigma Aldrich, St Louis, Mo.), and 100 ng/mL each of stem cell factor (SCF), fms-like tyrosine kinase 3 (flt-3) ligand and thrombopoietin (TPO) (PeproTech, Rocky Hill, N.J.).

Fetal liver samples between 15 and 24 gestational weeks were obtained from Advanced Bioscience Resources (Alameda, Calif.) or Novogenix Laboratories (Los Angeles, Calif.), as anonymous waste samples, with approval of the University of Southern California's Institutional Review Board. Human CD34+ HSC were isolated from the tissues following physical disruption and incubation in collagenase, with CD34+ cells isolated from the resulting single cell suspension by magnetic-activated cell sorting (MACS) (Miltenyi Biotec). In brief, Immunomagnetic column separation was used to enrich for CD34+ cells by incubating the MNCs with anti-CD34 microbeads (Miltenyi Biotec Inc.) at 4° C. for 30 min. Cells were then sent through the magnetic column and CD34+ cells collected and placed in cryovials with freezing medium (10% Dimethyl sulfoxide (Sigma Aldrich), 90% FBS) and cryopreserved in liquid nitrogen. Fetal liver derived HSC were cultured in maintenance media consisting of X-Vivo 15 (Lonza) supplemented with 50 ng/ml each of FCS, Flt3 ligand and TPO (R&D systems, Minneapolis, Minn.), plus 1% PSA.

ZFN Reagents.

ZFNs targeting the CCR5 and AAVS1 loci have been described previously. See, e.g., U.S. Pat. Nos. 7,951,925 and 8,110,379. The following FokI variants were used to construct obligate heterodimeric versions of ZFNs: EL:KK (CCR5, experiments with mobilized blood CD34+ cells), ELD:KKR (CCR5, experiments with fetal liver CD34+ cells; AAVS1). See, e.g., U.S. Pat. No. 8,623,618. An optimized pair of the AAVS1-targeting ZFNs were used in this study. See, U.S. Publication No. 20150110762. The ZFN coding sequences were cloned into a modified version of plasmid pGEM4Z (Promega, Madison, Wis.) containing a sequence of 64 alanines 3' of the inserted gene sequence, which was linearized by SpeI digestion to generate templates for mRNA synthesis. mRNA was prepared using the mMESSAGE mMACHINE® T7 ULTRA Kit (Life Technologies, Carlsbad, Calif.) or by TriLink Biotechnologies (San Diego, Calif.).

AAV Vectors.

All AAV vectors were produced at Sangamo BioSciences as described below, except for CMV-GFP reporter vectors of different serotypes, used to transduce fetal liver CD34+ cells, which were purchased from the University of Pennsylvania Vector Core (Philadelphia, Pa.). CCR5 and AAVS1 homologous donor templates (see Lombardo et al. (2011) Nat Meth 8:861-869; Lombardo et al. (2007) Nat Biotech 25:1298-1306; Wang et al. (2012) Genome Research 22:1316-1326) were cloned into a customized plasmid pRS165 derived from pAAV-MCS (Agilent Technologies, Santa Clara, Calif.), containing AAV2 inverted terminal repeats (ITRs), to enable packaging as AAV vectors using the triple-transfection method (Xiao et at (1998), J Virol 72:2224-2232). Briefly, HEK 293 cells were plated in 10-layer CellSTACK chambers (Corning, Acton, Mass.), grown for 3 days to a density of 80%, then transfected using the calcium phosphate method with an AAV helper plasmid expressing AAV2 Rep and serotype specific Cap genes, an adenovirus helper plasmid, and an ITR-containing AAV vector genome plasmid. After 3 days the cells were lysed by 3 rounds of freeze/thaw, and cell debris removed by centrifugation. AAV vectors were precipitated from the lysates using polyethylene glycol, and purified by ultracentrifugation overnight on a cesium chloride gradient. Vectors were formulated by dialysis and filter sterilized.

Gene Editing of HSC.

CD34+ HSC were stimulated for 16-24 hours, transduced with AAV vectors at the indicated vector genome (vg) copy per cell in maintenance media for 16-24 hours or the indicated time. The HSC were washed 2-3 times with PBS then diluted in BTXpress high performance electroporation solution (Harvard Apparatus, Holliston, Mass.) to a final density of $2-10\times10^6$ cells/ml for mobilized CD34+ HSC or $10^7$ cells/ml for fetal liver CD34+ HSC. This cell suspension was mixed with 40 μg/ml, or the indicated amount, of in vitro transcribed ZFN mRNA and electroporated in a BTX ECM830 Square Wave electroporator (Harvard Apparatus) in a 2 mm cuvette using a single pulse of 250V for 5 ms.

Analysis of Gene Modification.

For experiments using GFP donors, cells were collected at different time points post-treatment and analyzed for GFP expression using either a BD FACS Canto II (BD Biosciences, San Jose, Calif.), or Guava EasyCyte 6-2L or EasyCyte 5HT (EMD Millipore, Billerica, Mass.). Data acquired was analyzed using FlowJo software version 9.5.3 or version X (Treestar, Ashland, Oreg.), or InCyte version 2.5 (EMD Millipore). In addition, a semi-quantitative PCR was used to measure GFP integration at the CCR5 locus. Briefly, a primer present in the polyA region of the GFP cassette and a primer located 3' (outside) of the end of the right CCR5 homology arm region such that one primer bound only within the donor and the other bound to genomic DNA outside of the donor (In-Out primer set), were used to generate a PCR product. This was compared to the product resulting from a control primer set recognizing sequences in the CCR5 locus located 5' to the left homology donor, control primer set (CCR5 control primers), which only binds genomic DNA and was therefore used to normalize DNA input. The concentration of the In-Out primer set was 2 times that of the control primer set, to increase detection sensitivity. The relative intensities of each band were compared to a previously quantitated standard set generated from a pool of gDNA isolated from a K562 cell line with a constant level of GFP integration at the CCR5 locus as quantitated by Southern blot. A similar PCR reaction was used to detect integration at AAVS1 using specific primers (AAVS1 In-Out primers), but the reaction at this locus was not quantitative.

For experiments using RFLP donors, restriction fragment length polymorphism (RFLP) assays and Illumina deep sequencing were used to quantify the frequency of genome modification. The RFLP assay has been previously described (Lombardo 2007 ibid). For Illumina deep sequencing, gel-purified PCR products were amplified with a target-specific Miseq adaptor primer pair and sequence barcodes were added in the subsequent PCR reaction using the barcode primer pairs. Alternatively, 1/5000 of the PCR products amplified using primer pair out-out1 were re-amplified with primer pair according to standard methods, then 1/5000 of the second PCR products were amplified using the Miseq adaptor primers. The final PCR products were cleaned and sequenced in an Illumina Miseq sequencer, essentially as described by the manufacturer (Illumina, San Diego, Calif.). For analysis of gene modification levels, a custom-written computer script was used to merge paired-end 150 bp sequences, and adapter trimmed via SeqPrep. Reads were aligned to the wild-type template sequence. Merged reads were filtered using the following criteria: the 5' and 3' ends (23 bp) must match the expected amplicon exactly, the read must not map to a different locus in the target genome as determined by Bowtie 2 (Langmead & Salzberg, (2012) Nat Meth 9:357-359) with default settings, and deletions must be <70% of the amplicon size or <70 bp long. Indel events in aligned sequences were defined as described previously (Gabriel et al (2011) Nat Biotech 29:816-823), with the exceptions that indels of 1 bp in length were also considered true indels to avoid undercounting real events, and true indels must include deletions occurring within the sequence spanning between the penultimate bases (adjacent to the gap) of the binding site for each partner ZFN. Events with expected RFLP modification were defined based on perfect alignment with the DNA sequence containing the novel restriction site (CCR5 RFLP: AGTTTGTCTCGAGGTGATGA (SEQ ID NO: 12); AAVS1 RFLP: AGTGGGGCAAGCTTTACTAGGG (SEQ ID NO: 13) of the expected sequences.

Colony Forming Unit and Cell Growth Assays.

Cells were cultured in the X-Vivo 10 media with 100 ng/mL each of SCF, Flt3 ligand, and TPO, and 10 ng/ml interleukin (IL)-6. To monitor cell growth, cells were collected at indicated time points for cell counting by flow cytometry (Guava EasyCyte 5HT) after addition of 5 μg/ml propidium iodide (PI), to exclude dead cells, and flow count beads (Beckman Coulter) for reference.

For colony formation assays, cells were plated as a single-cell suspension at a density of 200-800 cells/mL in semi-solid methylcellulose-based medium containing 50 ng/mL SCF, 20 ng/mL GM-CSF, 20 ng/mL IL-3, 20 ng/mL IL-6, 20 ng/mL G-CSF, and 3 units/mL erythropoietin (EPO) (StemCell Technologies Inc., Vancouver, BC, Canada), at 24 hours post-electroporation (Li et al. (2013) Mol Ther 21:1259-1269). After 2 weeks of incubation, CFUs were classified and enumerated by trained operators on the basis of size and morphological characterization under a light microscope. Individual CFUs were then picked into 50 μl QuickExtract DNA extraction solution (Epicentre Biotechnologies, Madison, Wis.). DNA was extracted from colonies and subjected to deep sequencing analysis as described above. Colonies with 2 or more sequences comprising >10% of reads were treated as mixed clones and excluded from final genotyping analysis. Unique sequences comprising <10% of total sequence reads for a given sample were considered to be the result of processing errors and/or sample contamination and were also excluded from the analysis. Individual CFUs were identified as wt/wt (CFU count: a), wt/indel (b), wt/RFLP (c), indel/RFLP (d), indel/indel (e), and RFLP/RFLP (f). Frequency of RFLP modification in the population was then calculated using the following: % RFLP=(c+d+2f)/(2a+2b+2c+2d+2e+2f)* 100%.

HSC Subset Analysis.

Fetal liver derived CD34+ HSC were treated with AAV6 vectors and ZFN mRNA as described above. One day post-mRNA electroporation, cells were washed, blocked in FCS (Denville), and stained with the following fluorophore conjugated antibodies: CD34-PE (581) (BD Biosciences), CD90-BV510 (5E10) (BD Biosciences), and CD133/2-APC (293C3) (Miltenyi Biotec). Cell sorting into subsets based on expression of these markers was performed using a BD FACS Aria II (BD Biosciences), with all compensations performed using Diva software (BD Biosciences). Subsets were defined as long-term (LT) HSC (CD34+CD133+ CD90+), short-term (ST) HSC (CD34+CD133+CD90−), and multipotent progenitors (MPP) (CD34+CD133− CD90−) (Doulatov et al (2012) Cell Stem Cell 10:120-136). Subsets were cultured in maintenance media. GFP expression was determined 7 days later for each sorted subset by flow cytometry or specific PCR.

Mouse Engraftment and Human Cell Analysis.

HSC engraftment of 1 to 2 day old NOD.Cg-Prkcd$^{scid}$ Il2rg$^{tm1Wjl}$/SzJ (NSG) neonatal mice was performed as previously described (Holt et al. (2010) Nat Biotech 28:839-847). No preference was given to any animal property at the time of engraftment and mice were randomly assigned to each engraftment group. Two separate litters of mice were engrafted with HSC from each fetal liver donor to limit possible litter effects on results. Peripheral blood (70 µl) was sampled every 4 weeks from 8 weeks of age, and spleen and bone marrow were isolated at necropsy, as described (Holt, ibid). Whole blood and tissue samples were blocked in FCS (Denville) and stained with the following antibody-fluorophore conjugates: CD4-V450 (RPA-T4), CD3-PE (UCHT1), CD19-APC (HIB19), and CD45-PerCP (TUI16) (BD Biosciences) for 15 minutes at room temperature. Red blood cells were lysed after staining by incubation in BD Pharm Lyse buffer (BD Biosciences), lysis was halted by the addition of PBS, and cells were analyzed by flow cytometry using a BD FACS Canto II (BD Biosciences). Compensation samples were created with BD CompBeads (BD Biosciences). Analysis of flow cytometry data was performed using FlowJo software version 9.5.3 or version X (Treestar, Ashland, Oreg.). Compensation for stain overlap was performed post-acquisition using the tools included in FlowJo software. Initial gating was performed as forward scatter height versus forward scatter area to obtain the single cell population; the resulting population was plotted on a side scatter area versus forward scatter area grid to gate for live lymphocyte populations. Subsequent gates were set using full minus one controls such that less than 0.1% of cells not receiving a specific stain were considered positive for that stain. There was no operator blinding in the analyses.

Secondary transplantations were performed using 10$^7$ mouse bone marrow cells harvested from the upper and lower limbs of two separate mice for each condition (CCR5-RFLP/ZFN and CCR5-GFP/ZFN). Each pooled bone marrow sample contained 10% human CD45+CD34+ cells, and was transplanted into 8 week old female NSG mice, as described (Holt ibid).

Statistical Analysis.

All statistical analyses were performed within the software suite GraphPad Prism 5 (GraphPad Software Inc., La Jolla, Calif.) or the Excel Analysis ToolPak.

Example 7: Human HSC are Efficiently Transduced by AAV Serotype 6 Vectors

In order to evaluate AAV vectors as homologous donors for genome editing in HSC, we compared the ability of different AAV capsid serotypes to transduce these cells. We used GFP reporter vectors and CD34+ HSC isolated from both mobilized blood and fetal liver.

As shown in FIG. 11, for both HSC sources, we found that AAV serotype 6 gave the highest rates of transduction across a range of vector doses.

Figure 12A:
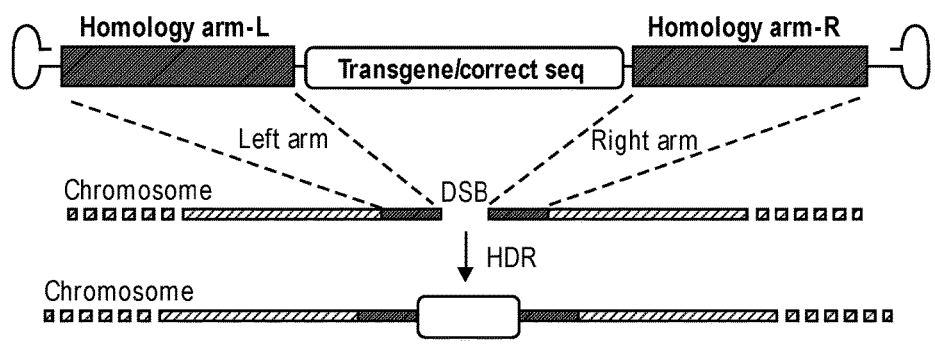
FIGS. 12A through 12H depict combinations of ZFN mRNA and AAV6 vectors that promote high levels of site-specific gene editing at the CCR5 locus.
Figure 12B:
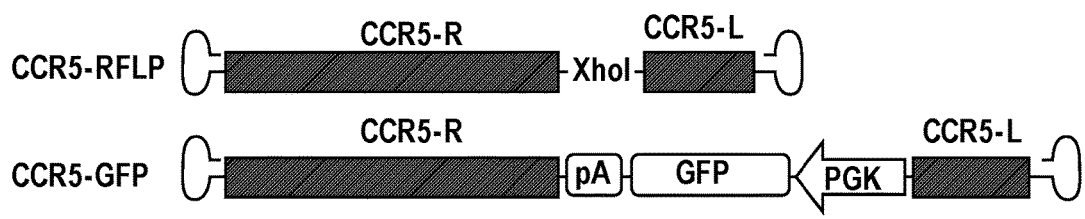

Example 8: AAV6 Homology Donors and ZFN mRNA Electroporation Promotes High Levels of Gene Editing in HSC We examined the ability of AAV6 vectors to promote HDR-mediated genome editing in mobilized blood CD34+ HSC. Sixteen to twenty-four hours after transduction of the cells with AAV6 vectors, a site-specific double-stranded DNA break (DSB) was introduced at the CCR5 locus by a previously characterized CCR5 ZFN pair (U.S. Pat. No. 7,651,925), in order to stimulate HDR (FIG. 12A). Two different homologous donor templates were evaluated as AAV6 vectors, representing both minor gene editing events (restriction site insertion) or the more significant insertion of a larger gene cassette. In each case, the AAV6 vectors contained the same homologous CCR5 sequences, flanking, either an XhoI restriction site (CCR5-RFLP) or a GFP expression cassette (CCR5-GFP) (FIG. 12b). Successful gene editing events were determined by population deep sequencing and RFLP analysis to detect XhoI insertion, or by flow cytometry and semi-quantitative PCR for site-specific GFP addition.

Figure 12C:
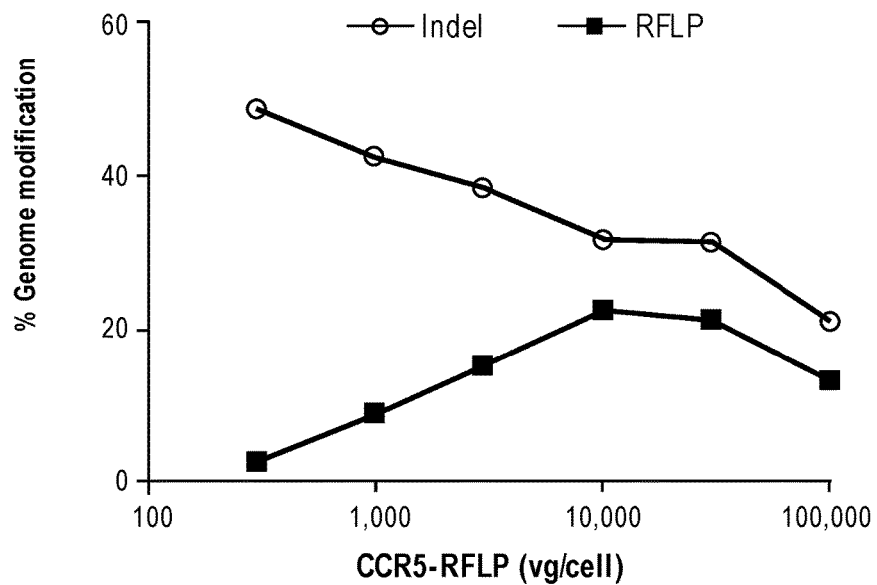
Figure 12D:
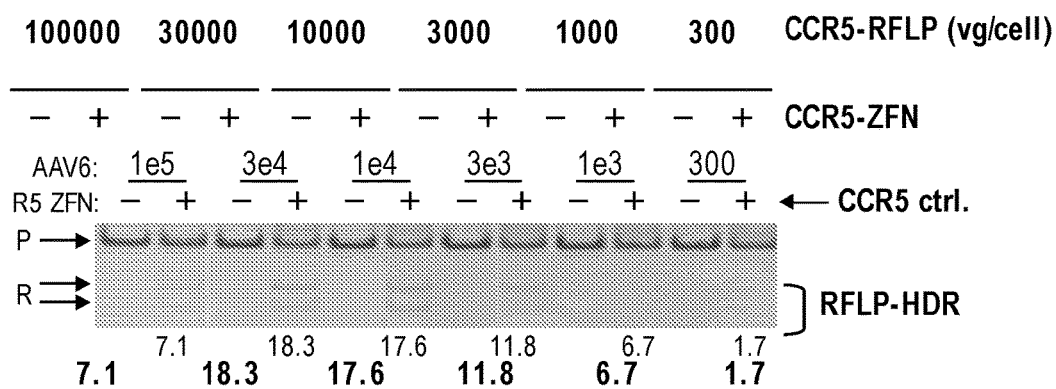
Figure 12F:
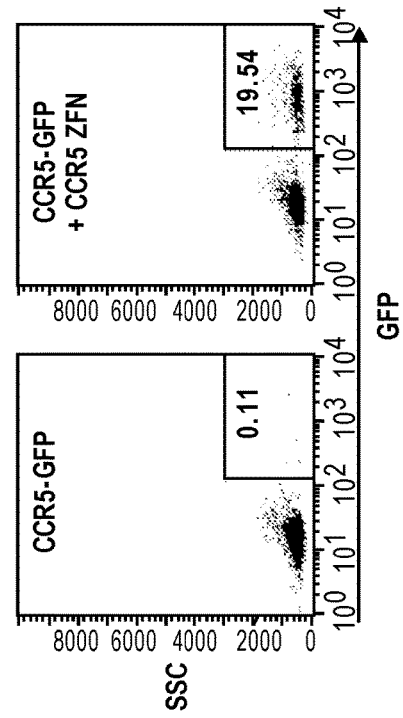
Figure 12H:
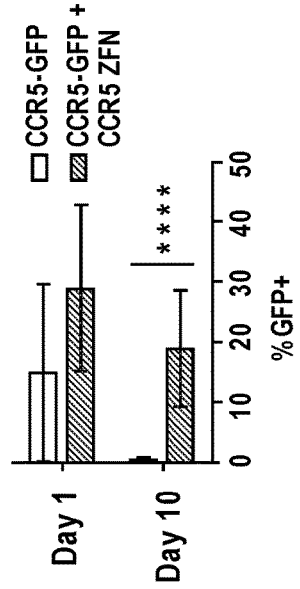
Figure 12E:
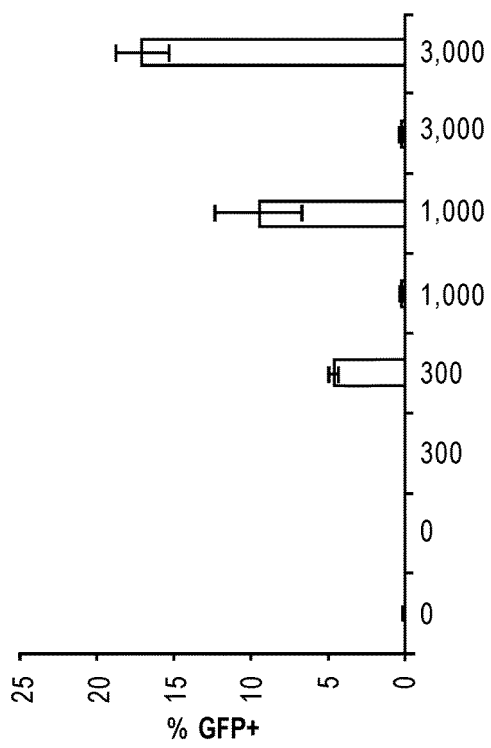
Figure 12G:
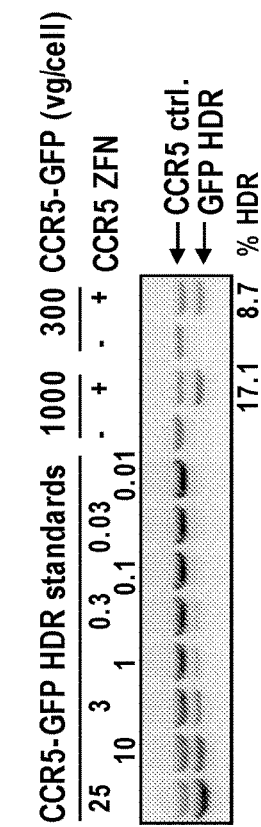

NHEJ and HDR repair are competitive events, and, as shown in FIG. 12C, we found that increasing the dose of the CCR5-RFLP vector led to an increase in the rate of XhoI insertion at the CCR5 locus, in the presence of CCR5 ZFNs, resulting in greater than 20% of alleles being modified. Furthermore, as shown in FIGS. 12C and 12D, this was accompanied by a corresponding decrease in the extent of the characteristic NHEJ-mediated indels. Similarly, increasing levels of stable GFP expression were observed following transduction by increasing doses of the CCR5-GFP vector, but only when the ZFN mRNA was also delivered. See, FIGS. 12E through 12G. The optimal time for AAV6 transduction relative to ZFN mRNA electroporation was found to be between 24 hours pre- and 1 hour post-electroporation, indicating that the treatment schedule is relatively flexible. As show in FIG. 12H, transduction of fetal liver derived CD34+ HSC with the CCR5-GFP vector and ZFN mRNA also resulted in high levels of stable and site-specific GFP addition.

Efficient site-specific gene editing was also observed when using reagents specific for the AAVS1 'safe harbor' locus. See, e.g., U.S. Pat. No. 8,110,379. In mobilized blood HSPC, insertion of a HindIII restriction site occurred, on average, at 28% of the AAVS1 alleles, while GFP addition was observed at an average rate of 26% of the cells. Similar high rates of gene editing at AAVS1 were achieved in fetal liver HSPC, with stable GFP addition detected in more than 40% of the cells.

Taken together these results demonstrate that AAV6 vectors are an effective vehicle for delivering homologous donor DNA templates to CD34+ HSC, and that when combined with ZFN mRNA electroporation, the protocol supports both minor in situ genome editing events and larger gene additions.

Example 9: AAV6 Vectors Use Homology Directed Repair to Genetically Modify HSC

Figure 13A:
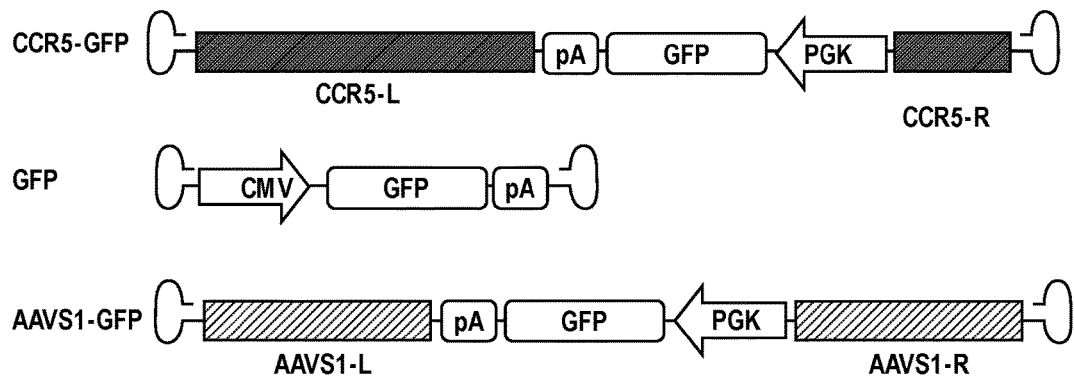
FIGS. 13A through 13D depicts site-specific gene editing by AAV6 vectors using homology directed repair.

In addition to engaging the cell's homology-directed repair pathways, AAV vectors can also be inserted at the site of a DSB through NHEJ-mediated end capture events. To examine whether any stable gene insertion was due to this alternative pathway, we combined CCR5 ZFN mRNA treatment of HSC with AAV6 vectors containing GFP expression cassettes but lacking sequences homologous to CCR5. These included a vector genome with no flanking genomic regions, and one with mismatched arms, homologous to the AAVS1 locus. See, FIG. 13A.

Figure 13B:
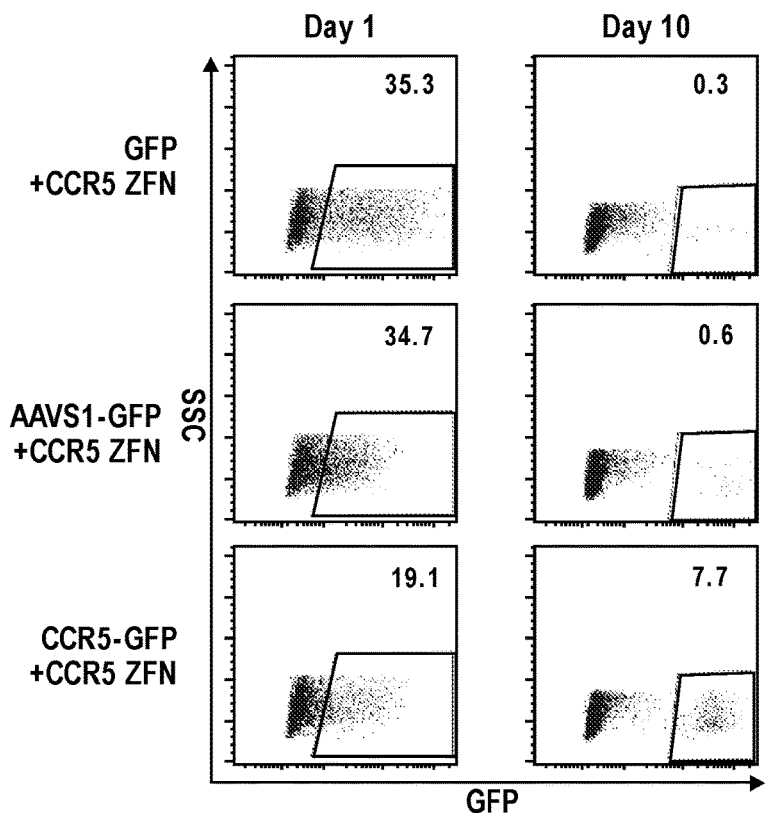
Figure 13C:
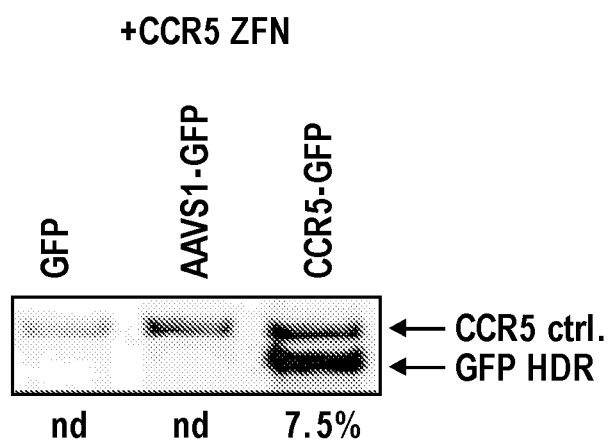
Figure 13D:
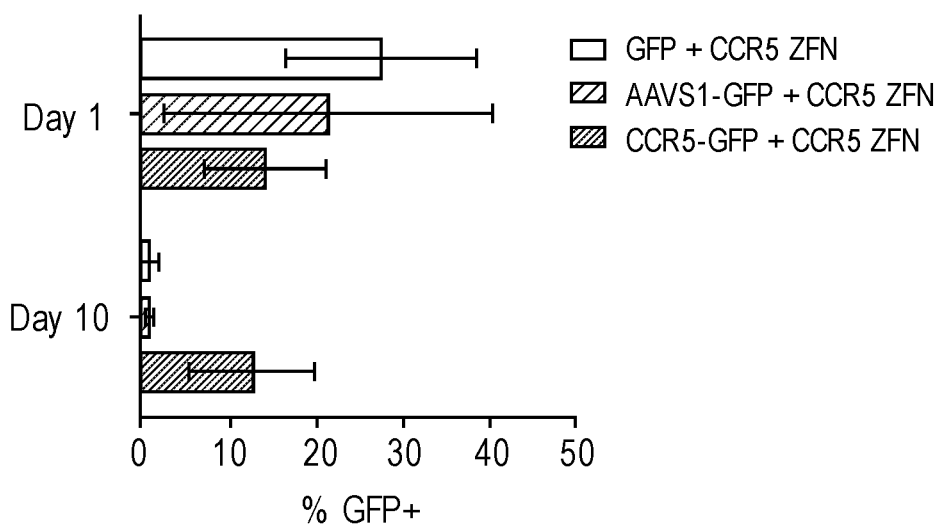

The vectors were introduced into the cells and followed one day later by CCR5 ZFN mRNA electroporation. All three vectors resulted in initial high levels of GFP expression at one day post electroporation, reflecting equivalent rates of introduction of the AAV vector genomes into HSC. However, as shown in FIGS. 13B and 13D, by day 10, only the cells receiving the AAV6 vector with CCR5 homology arms had persistent levels of GFP expression. GFP expression was also considerably less variable than day 1 levels, as expected for a site-specific integration event. As shown in FIG. 13C, semi-quantitative PCR assay further confirmed that GFP expression resulted from insertion of the GFP cassette into the CCR5 locus. The requirement for matched homologous sequences to support gene addition at the CCR5 locus identifies homology-directed repair pathways as the mechanism of stable gene editing.

Example 10: Analysis of AAV6 and ZFN Treated HSPC

We examined the ability of mobilized blood HSPC treated with the CCR5-RFLP vector plus ZFN mRNA to proliferate in culture and to differentiate into hematopoietic lineages. Although we observed an initial decrease of 23% in the absolute number of the treated cells that grew in bulk culture at one day post-electroporation, by two days post-electroporation the rate of growth of these cells was indistinguishable from a mock treated population. This indicates that although some of the cells in the bulk CD34+ population were sensitive to the treatment, the proliferative potential of the surviving cells was not impacted, suggesting that any such effects could be compensated for by using higher numbers of cells.

Figure 14A:
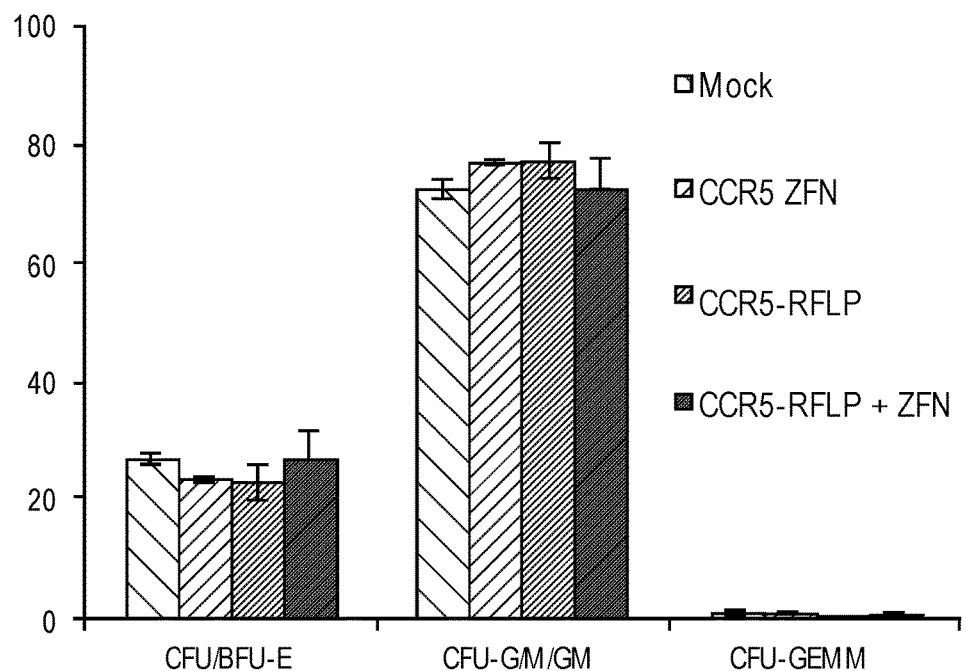
FIGS. 14A and 14B show genome modification in erythroid and myeloid lineages. Mobilized blood CD34+ HSC were transduced with 1,000 vg/cell CCR5-RFLP donor (CCR5-RFLP), and/or electroporated 16 hours later with 40 ug/ml of CCR5 ZFN mRNA (CCR5-RFLP+ZFN). Mock treated HSC were cultured as a control.
Figure 14B:
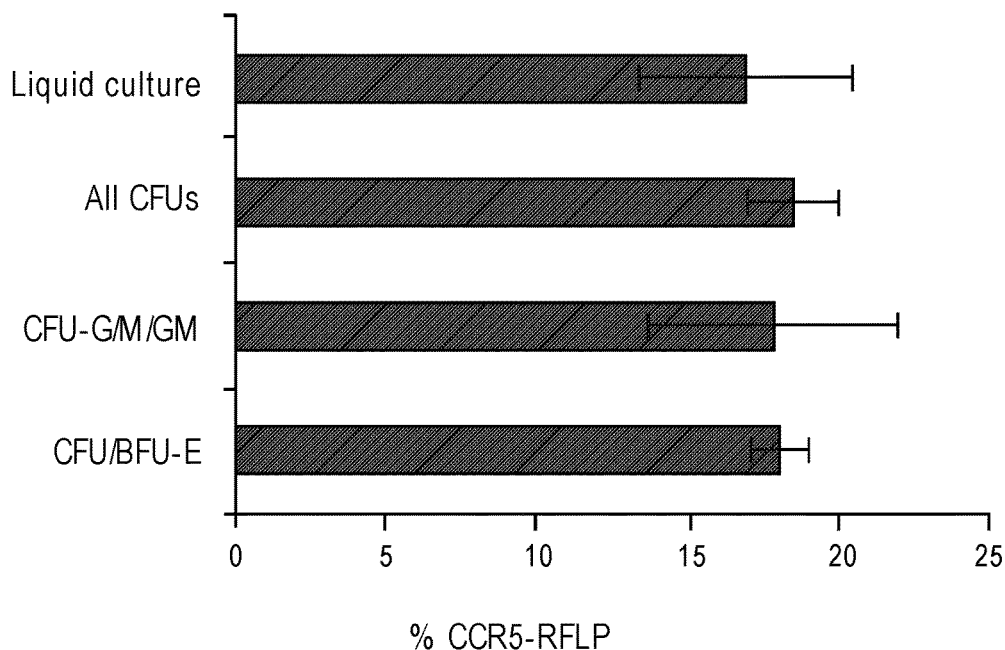

We also plated AAV6 and ZFN treated cells in methylcellulose and analyzed the colonies that formed. Here, as shown in FIG. 14A, we found no difference in the relative percentages of the different colony subtypes that developed in the various treatment arms of the experiment. In addition, as shown in FIG. 14B, by picking colonies from the methylcellulose cultures and analyzing their genotype, we confirmed that the levels of genome editing in the myeloid (CFU-G/M/GM) and erythroid (CFU/BFU-E) colonies were indistinguishable from the levels in the bulk liquid culture. Finally, in a similar experiment using the CCR5-GFP vector, we observed GFP+ cells in all colony types.

Taken together, these data indicate that the combined AAV6 transduction/ZFN mRNA treatment does not adversely impact the growth and differentiation potential of HSC, and genome modified cells can be found in multiple lineages Example 11: Efficient Gene Editing Occurs in the Most Primitive Subsets of CD34+ HSC CD34+ cells comprise a mixed population of primitive and more differentiated cells that can be further divided into sub-populations based on expression of markers such as CD90 and CD133 (FIG. 15A). These markers distinguish the most primitive long-term (LT) repopulating cells from more differentiated short-term (ST) repopulating cells, and more committed multipotent progenitors (MPP) (Reitsma et at (2002) in Hematopoietic Stem Cell Protocols, Vol. 63. (eds. C. Klug & C. Jordan) 59-77 (Humana Press,); Takahashi et al. (2014) *Leukemia* 28, 1308-1315). The CD34+ CD133+ CD90+ LT-HSC population is especially clinically relevant as these cells have the potential to persist and contribute to hematopoiesis long-term. However this population has proven to be the most difficult to edit when targeted nucleases have been combined with donor templates delivered by IDLVs (Genovese et al. (2014) *Nature* 510:235-240; Hoban et al. (2015) *Blood* 125:2597-2604).

To evaluate the ability of AAV6 donors to promote HDR-mediated gene editing in LT-HSC, we treated the bulk CD34+ population with AAV6 vectors and ZFN mRNA, then sorted into different subsets based on expression of CD34, CD133 and CD90. We cultured each population for a further 7 days, then measured the levels of stable GFP expression in the different populations by flow cytometry.

Figure 15B:
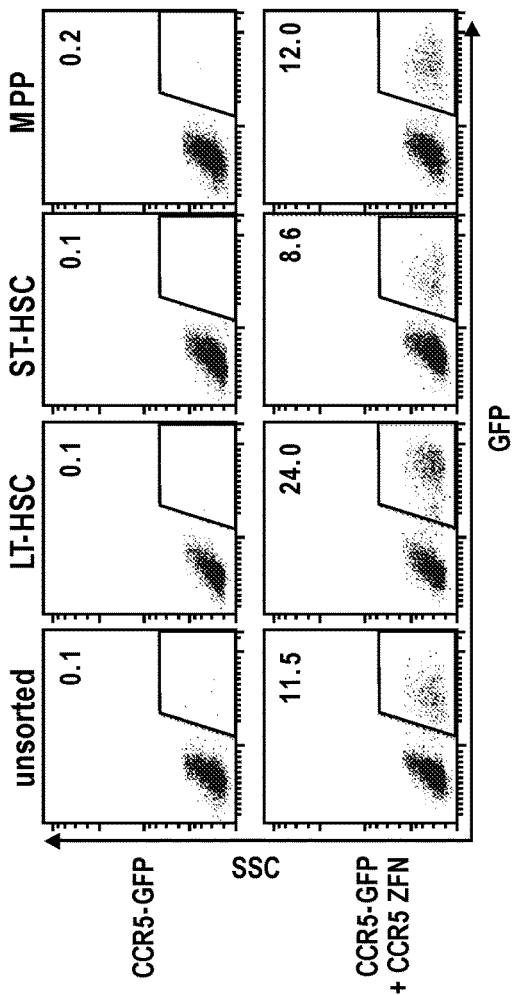
FIGS. 15A through 15G shows gene editing in different subsets derived from CD34+ HSC populations. Fetal liver CD34+ cells were treated with 1,000 vg/cell CCR5-GFP AAV vectors and electroporated with CCR5 ZFN mRNA, then sorted based on expression of CD133 and CD90. Control cells received only CCR5-GFP.
Figure 15A:
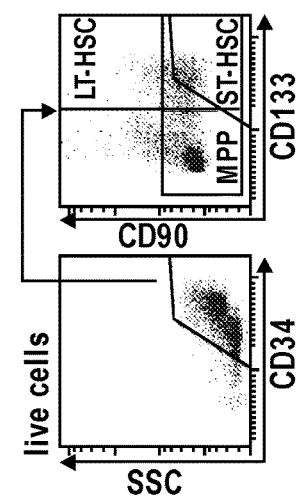
Figure 15C:
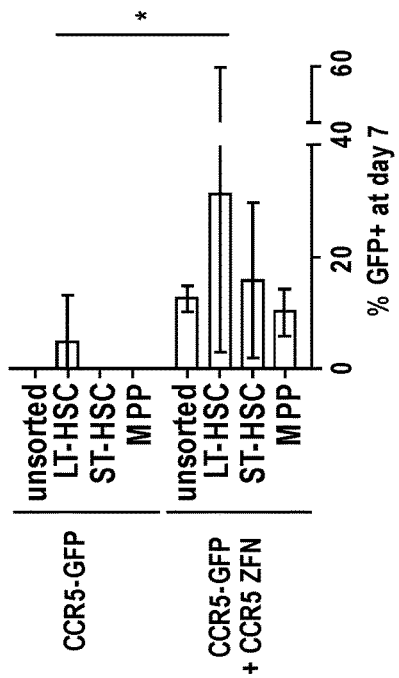
Figure 15D:
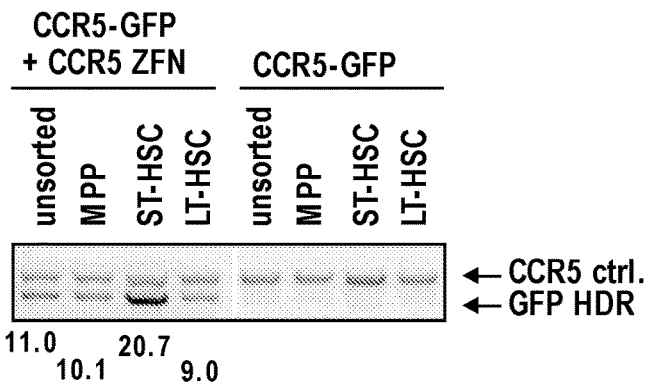
Figure 15E:
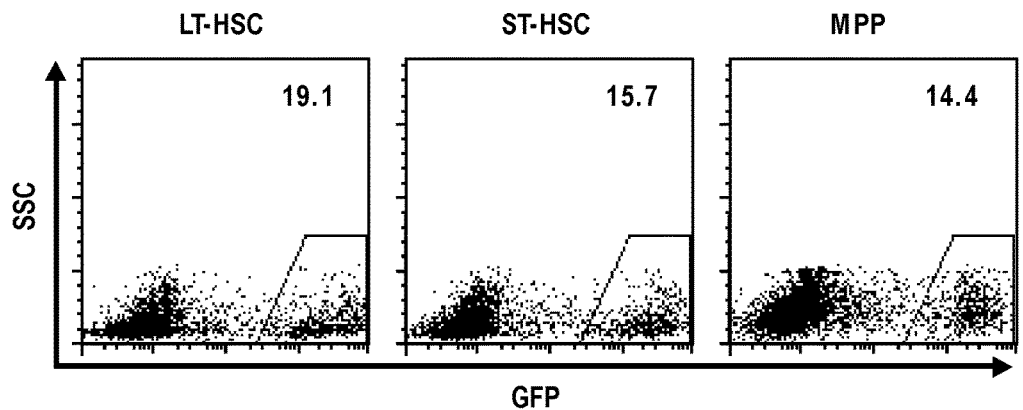
Figure 15F:
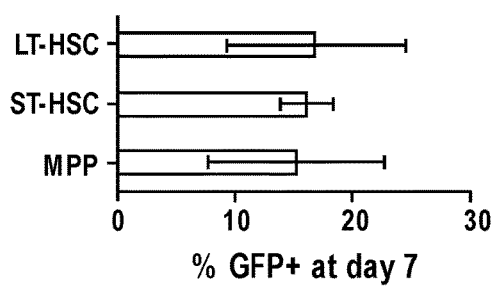
Figure 15G:
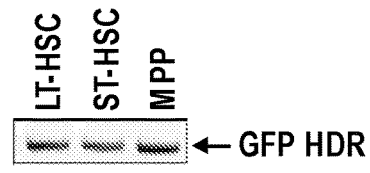

As shown in FIGS. 15B and 15C, we found that each of the subsets expressed stable GFP and there were no statistically significant differences between the populations, including for the LT-HSC. These observations were further validated by performing site-specific PCR to detect insertion of GFP at the CCR5 locus, which confirmed similar levels of insertion in the different subsets (FIG. 15E). Finally, we repeated these analyses using AAVS1 specific reagents, which also demonstrated equivalent HDR-mediated gene addition at the AAVS1 locus in the LT-HSC population (FIGS. 15F through 15H).

Figure 16A:
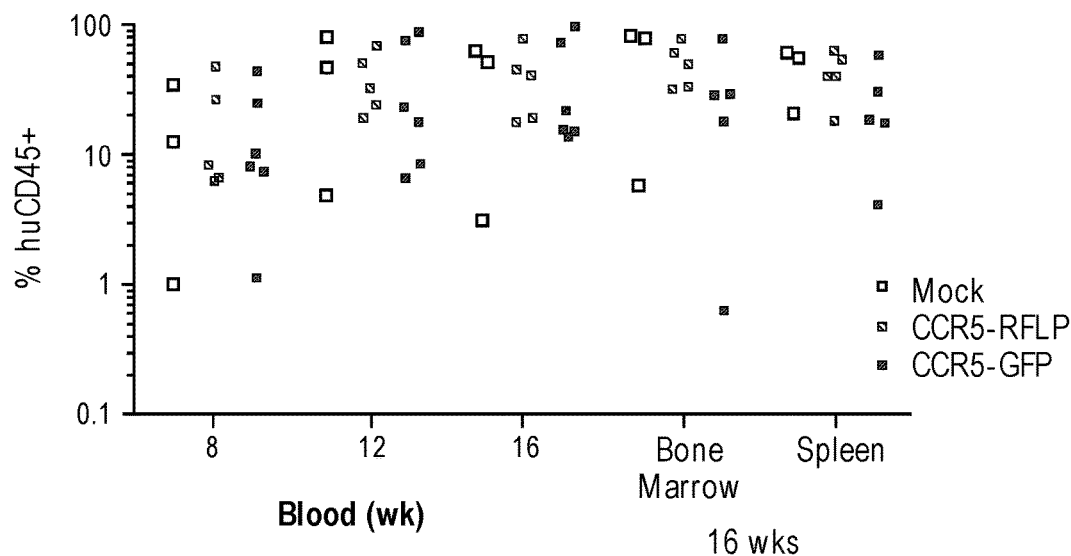
FIGS. 16A through 16E show engraftment of NSG mice with gene edited human HSC.
Figure 16B:
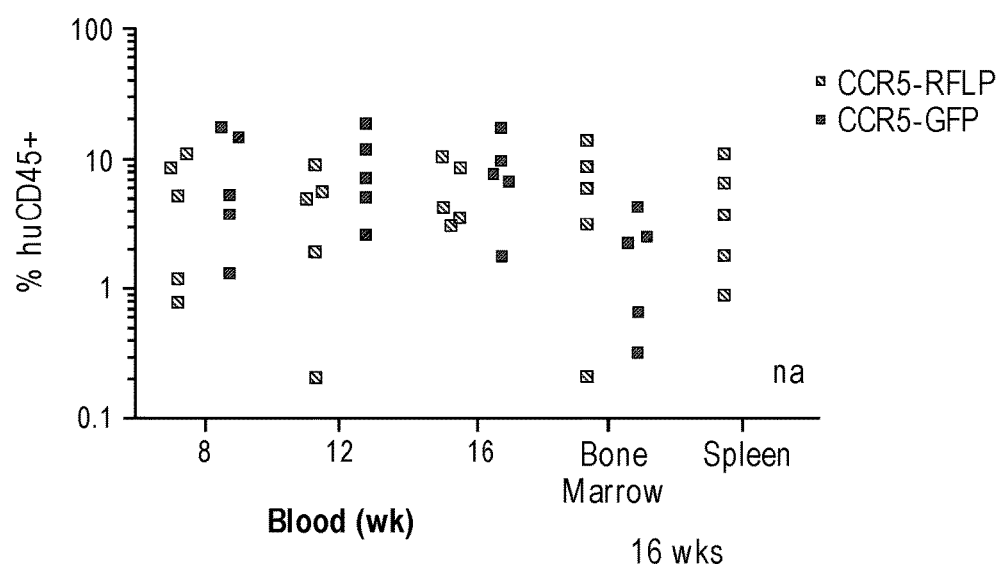
Figure 16C:
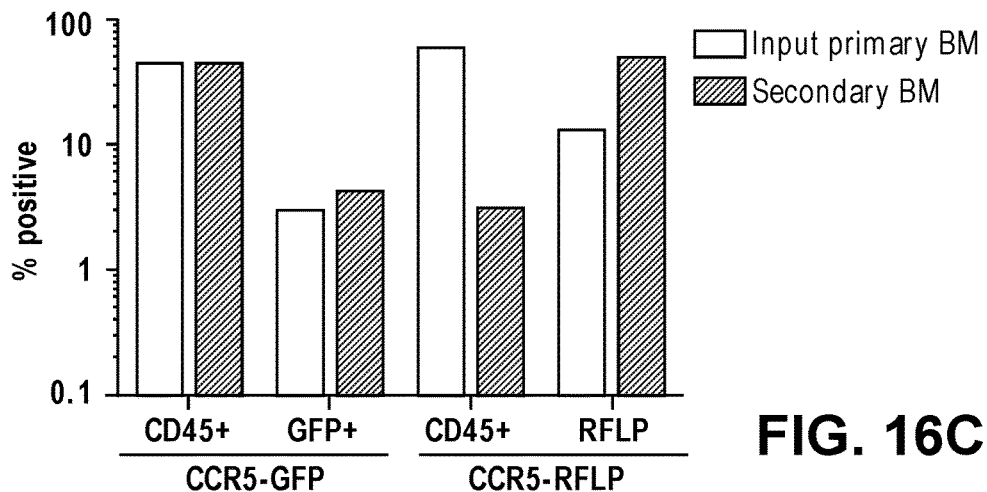
Figure 16D:
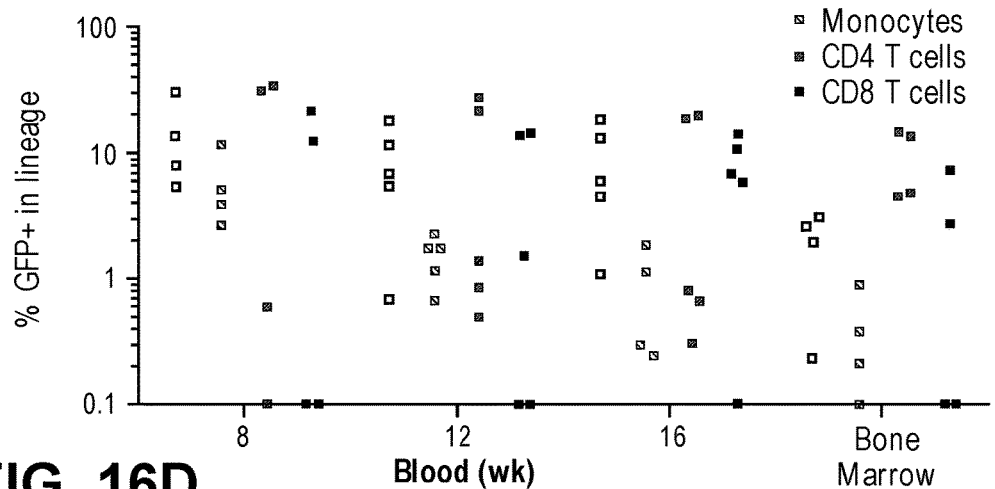

Example 12: Gene Edited HSC Engraft and Differentiate in NSG Mice, and Support Secondary Transplantation A stringent test of human HSPC potential is to evaluate the ability of the cells to engraft and differentiate in immune-deficient mice, and to further persist during secondary transplantations (Holt, ibid). Fetal liver CD34+ HSC, treated with CCR5-GFP or CCR5-RFLP vectors and electroporated with CCR5 ZFN mRNA, were engrafted into neonatal NSG mice and monitored over 16 weeks. As shown in FIG. 16A, analysis of peripheral blood at weeks 8, 12 and 16 post-transplantation, and the bone marrow and spleen at 16 weeks, revealed development of human CD45+ leucocytes at levels that were indistinguishable from mice receiving untreated control HSC. At each time point, the human cells were further stained for lineage specific markers and analyzed for the presence of B cells (CD19+), monocytes (CD3-CD4+), CD4 T cells (CD4+CD3+) and CD8 T cells (CD4-CD3+). This revealed that the treated HSC were capable of differentiating into each lineage at rates similar to untreated cells, confirming no difference in hematopoietic potential and agreeing with the observations from the in vitro CFU analyses (see, FIG. 14).

Figure 8A:
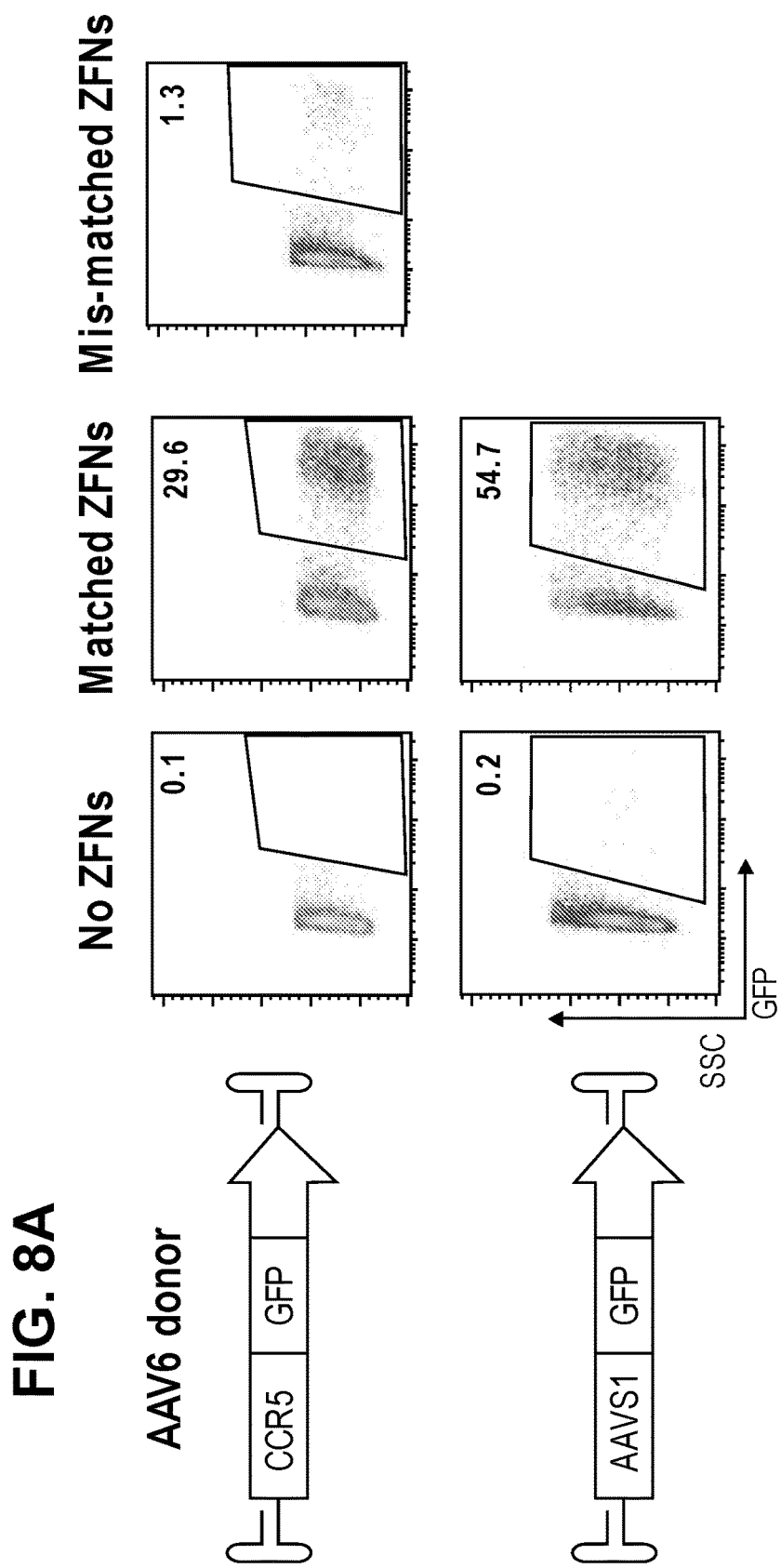
FIGS. 8A through 8F show targeted integration of GFP into safe harbors in a mouse model.
Figure 8B:
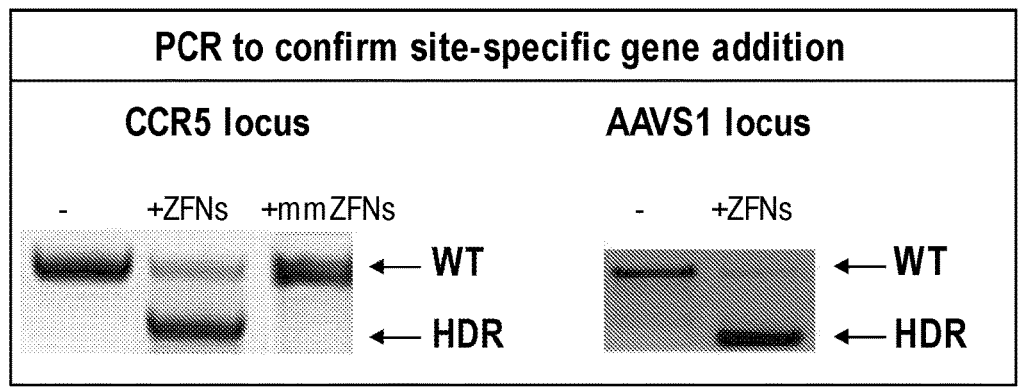
Figure 8C:
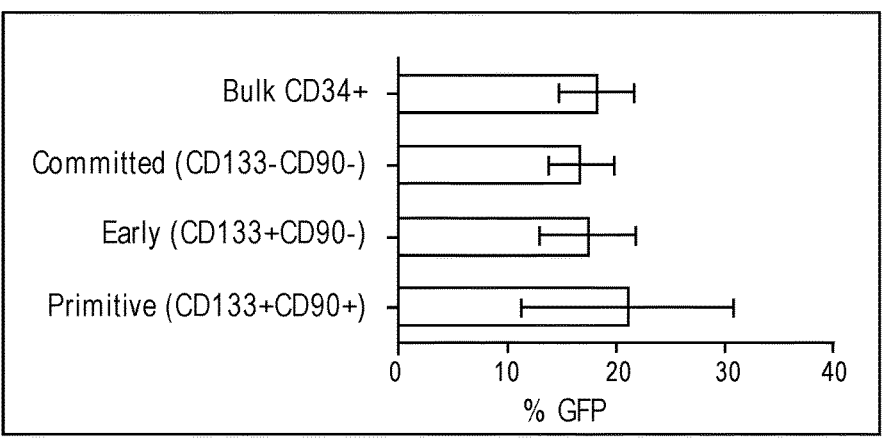
Figure 8D:
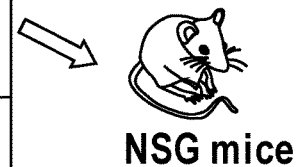
Figure 8E:
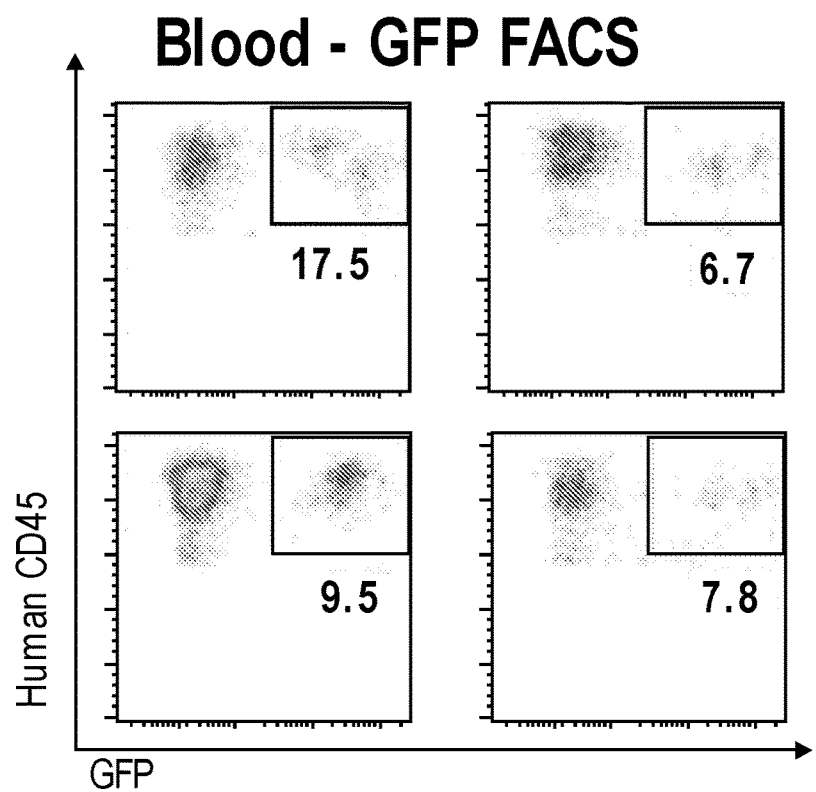
Figure 8F:
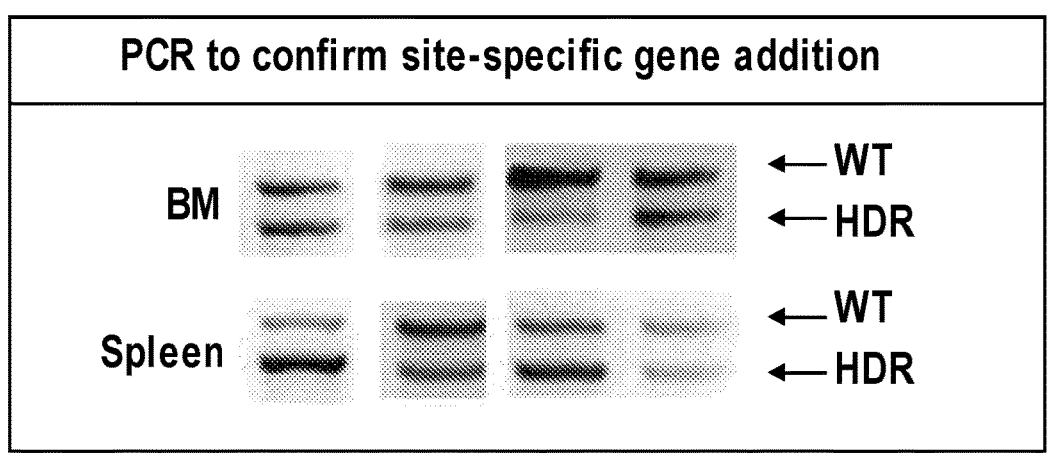
Figure 9B:
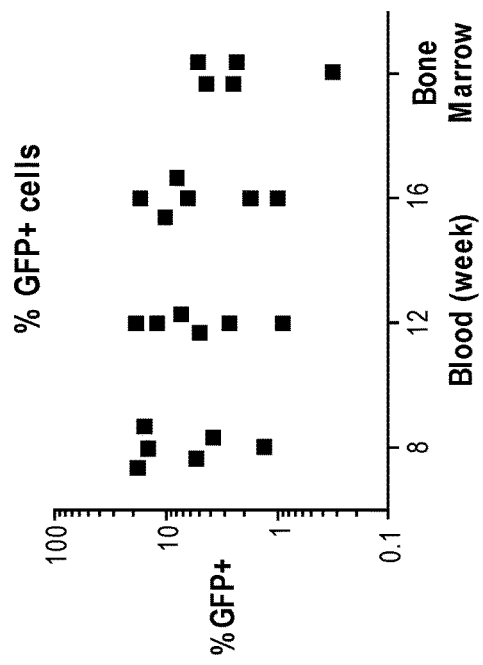
FIGS. 9A through 9C show the percentage of CD45+ cells (FIG. 9A) and the percentage of GFP+ cells (FIG. 9B) in blood and bone marrow following engraftment of HSCs (treated with CCR5 ZFNs plus CCR5-GFP AAV6 vectors containing a GFP cassette and CCR5 homology sequences (white boxes in FIG. 9A), or untreated, grey boxes in FIG. 9A) into humanized mice.
Figure 9C:
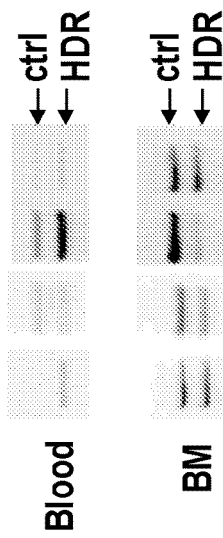
Figure 9A:
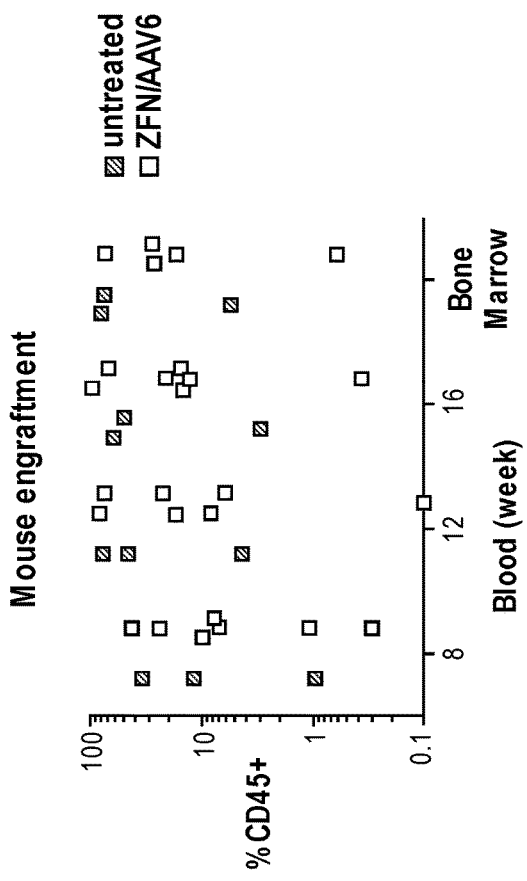
Figure 16E:
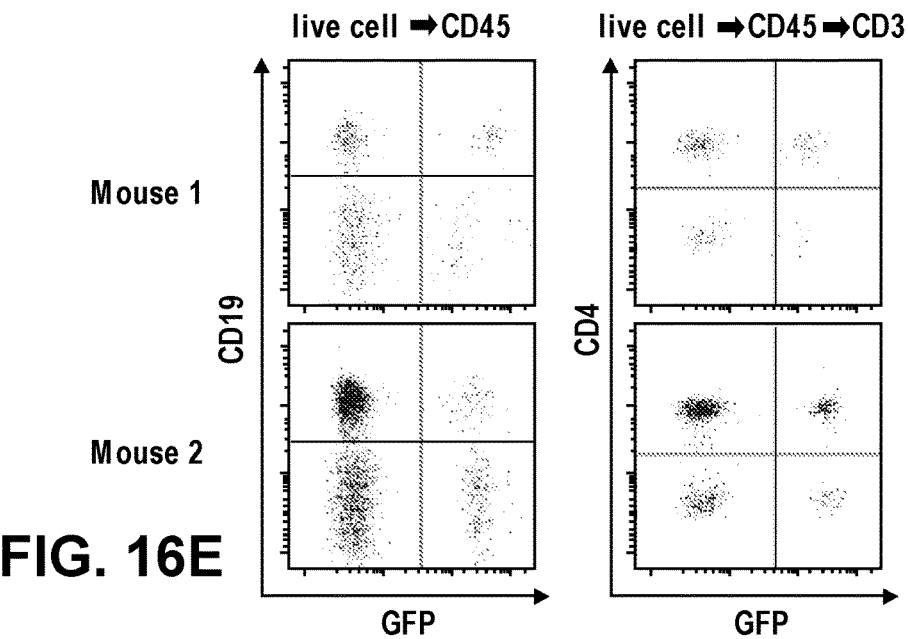
Figure 17:
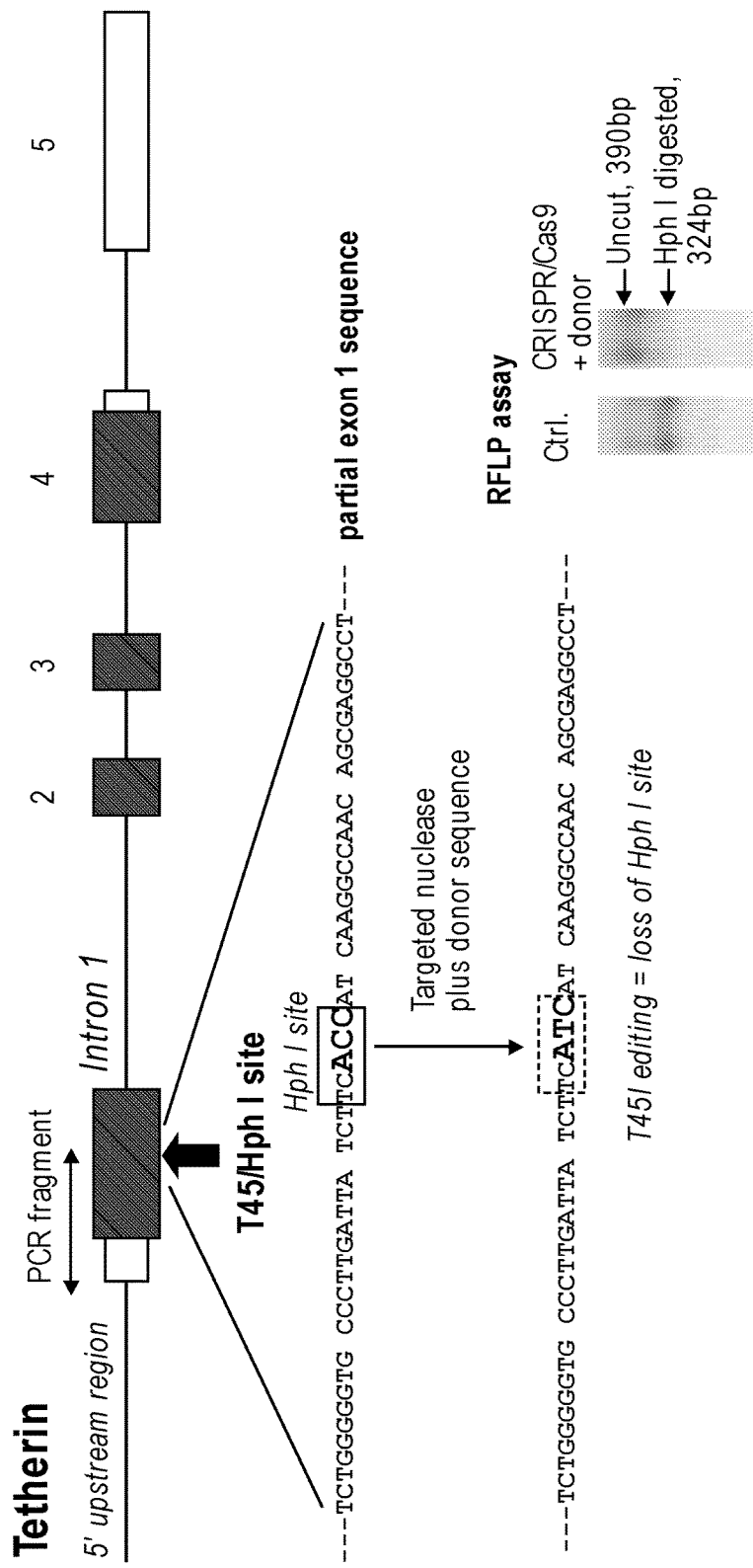
FIG. 17 (SEQ ID NO: 14 and SEQ ID NO: 15) are schematics showing the tetherin genomic locus, including the position of residue threonine 45 in exon 1, and the overlapping Hph I restriction enzyme site. Editing of threonine 45 to isoleucine (T45I) following introduction of CRISPR/Cas9 and a donor sequence containing the ACC→ATC single base change results in loss of the Hph I site. This can be detected by an RFLP assay (bottom right) comprising PCR across exon 1 to amplify a 390 bp fragment, followed by Hph I digestion which releases a 324 base pair fragment. Loss of the Hph I site by editing prevents release of the 324 base pair fragment. "Control" refers to cells treated with donor sequence only.

We next examined the levels of gene editing in the human cells that developed in the mice, by flow cytometry (CCR5-GFP) or deep sequencing (CCR5-RFLP), and readily observed such edited cells in the circulation and tissues, in both the bulk CD45+ population (see, FIG. 16B) and individually sorted lineages (see, FIG. 16E). Evidence of site-specific GFP insertion at the CCR5 locus by the CCR5-GFP vector was also confirmed in the blood and tissues of individual mice by semi-quantitative PCR (see, FIGS. 8F, 9C).

Together, these results demonstrate that modified cells are capable of engrafting mice and differentiating into multiple different lineages.

Finally, we examined the ability of the edited human cells to persist through secondary transplantations. Bone marrow harvested from two mice from each of the separate CCR5-GFP and CCR5-RFLP cohorts was pooled and used to transplant one additional adult NSG mouse for each group, with these mice then analyzed 20 weeks later. Levels of human CD45+ cells were measured in both the input bone marrow and the tissue from the secondary transplant recipients, together with GFP expression by flow cytometry or XhoI site insertion by deep sequencing, as appropriate. We observed similar levels of genome editing in the input and secondary bone marrow for both groups of mice (see, FIG. 16C). Since these edited cells had persisted for a total of 36 weeks in mice and following secondary transplantation, these data strongly support the modification of LT-HSC in the initial population of treated CD34+ HSC.

In sum, donor templates provided as AAV6 vectors supported efficient levels of nuclease-mediated genome editing in LT-HSC in vitro that were indistinguishable from the bulk CD34+ population, and the edited HSPC supported long-term engraftment in humanized mice, including during secondary transplantations.

Example 13: Nuclease-Mediated Modification of Restriction Factor Genes

Single guide RNAs as shown in Table 1 were designed to restriction factor genes and used in CRISPR/Cas nuclease systems essentially as described in U.S. Pat. No. 8,697,359. In particular, sequences in TRIM5α, APOBEC3G ("A3G") and tetherin genes were targeted by CRISPR/Cas9 to create a DNA break.

CRISPR/Cas9 reagents were introduced into 293 cells by transfection and 48 hours later, the frequency of indels were measured by Cel-1 assay. Results are shown in Table 1. All sequences shown are for *S. aureus* Cas9 except the one indicated by "*", which is a guide RNA sequence for the *S. pyogenes* "mini" Cas9 (Ran et al, ibid). The relative efficiency of DNA break induction for each reagent was measured by calculating the frequency of insertions/deletions (indels) created by NHEJ repair when the CRISPR/Cas9 was introduced into a cell in the absence of a homologous donor repair template.

TABLE 1

Exemplary CRISPR guide RNA target sequences in both introns and exons of indicated genes used to introduce a DNA break

| Target location | Genomic sequence targeted by guide RNA (5' - 3') | Cutting efficiency, Cel-1 (%) | Distance from site to be mutated |
|---|---|---|---|
| TRIM5a - intron 7 | CTCCTTATAACTTCTAAACA (SEQ ID NO: 16) | 22 | 202 |
| TRIM5a - exon 8 | GAAACCACAGATAATATATG (SEQ ID NO: 17) | 42 | 9 |
| A3G - intron 1 | GACTGCTTAAGTGTCTGTGA (SEQ ID NO: 18) | 40 | 134 |
| A3G - intron 1 | GTCCTTCCCACACATACCTG (SEQ ID NO: 19) | 38 | 157 |
| A3G - intron 2 | TGTGGGAACTGCACCTTTGT (SEQ ID NO: 20) | 29 | 461 |
| Tetherin - intron 1 | CCTTTGGATGGCCTAGTACT (SEQ ID NO: 21) | 43 | 184 |
| Tetherin - intron 1 | GAGGTCCTGAAACTGCTCCT (SEQ ID NO: 22) | 46 | 274 |
| Tetherin - intron 1 | GCTCCTGGGCCCCCACATCA (SEQ ID NO: 23) | 47 | 288 |
| Tetherin - exon 1 | TCAAGGCCAACAGCGAGGCC (SEQ ID NO: 24) | 26 | 4 |
| Tetherin - exon 1 | TGATTATCTTCACCATCAAG (SEQ ID NO: 25) | 28 | 8 |
| Tetherin - exon 1* | GGGGTGCCCTTGATTATCTTC (SEQ ID NO: 26) | 40 | 18 |

Thus, endogenous cellular genes involved in HIV infection (e.g., restriction factors) can be modified by nucleases.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

---

What is claimed is:

1. An isolated genetically modified cell that will not sustain HIV infection, wherein the genetic modifications comprise:
   (i) modification of an endogenous Trim5α gene to increase its activity against HIV;
   (ii) modification of an endogenous viral host factor gene by mutations, which mutations decrease its ability to support HIV infection; and
   (iii) insertion of an exogenous transgene encoding a Trim5α-cyclophilin A peptide (Trim5α-Cyp) fusion protein into an endogenous safe harbor locus wherein the genetically modified cell will not sustain HIV infection.

2. The cell of claim 1, wherein the cell is stem cell.

3. The stem cell of claim 2, wherein the stem cell is a hematopoietic stem cell (HSC).

4. An isolated genetically modified cell descended from the cell of claim 1.

5. A composition comprising the cell of claim 4.

6. A method of generating the cell according to claim 1, the method comprising genetically modifying the cell such that:
   (i) an endogenous Trim5α gene is modified to increase its activity against HIV;
   (ii) an endogenous viral host factor gene is modified by mutations, which mutations decrease its ability to support HIV infection; and
   (iii) an exogenous transgene encoding a Trim5α-Cyp fusion protein is inserted into an endogenous safe harbor locus wherein the cell will not sustain HIV infection.

7. The method of claim 6, wherein the modification of the endogenous Trim5α comprises introduction of one or more point mutations in the endogenous gene sequence to alter the amino acid sequence of the encoded Trim5α or introduction of a sequence encoding a functional domain such that the sequence encoding the functional domain is operably linked to the endogenous sequence encoding the Trim5α.

8. The method of claim 7, wherein the amino acids modified are R332 and R335 in TRIM5α.

9. The method of claim 6, wherein the Cyp peptide comprises a cyclophilin A (CypA) peptide.

10. The method of claim 6, wherein in the modification of an endogenous viral host factor comprises introduction of mutations that knock out the expression of the endogenous viral host factor.

11. The method of claim 10, wherein the endogenous viral host factor is selected from the group of LEDGF/p75 (PSIP1), FPSF6, Nup358 and TNP03.

12. The method of claim 6, wherein the safe harbor locus is selected from the group of CCR5, AAVS1, or HPRT.

13. The method of claim 6, wherein modification is made using a nuclease.

14. The method of claim 13, wherein the nuclease comprises a zinc finger nuclease (ZFN), a TALE-effector domain nuclease (TALEN), CRIPSR/Cas system or TtAgo system.

* * * * *